(12) United States Patent
Fielding et al.

(10) Patent No.: US 6,261,760 B1
(45) Date of Patent: Jul. 17, 2001

(54) REGULATION OF THE CELL CYCLE BY STEROLS

(75) Inventors: Christopher J. Fielding; Phoebe E. Fielding, both of Mill Valley, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 09/264,693

(22) Filed: Mar. 8, 1999

Related U.S. Application Data

(60) Provisional application No. 60/077,351, filed on Mar. 9, 1998.

(51) Int. Cl.[7] .............................. C12Q 1/00; G01N 33/53; G01N 33/567; G01N 33/574; G01N 33/48
(52) U.S. Cl. .............................. 435/4; 435/7.1; 435/7.2; 435/7.23; 436/64; 536/23.5; 536/24.1
(58) Field of Search .......................... 435/7.1, 7.2, 7.23, 435/4; 436/64; 536/23.5, 24.1

(56) References Cited

PUBLICATIONS

Field et al., Cholesterol metabolism in regenerating liver of the rat, American Journal of Physiology, vol. 249, pp. G679–684, 1985.*
Gal et al., Low–density lipoprotein as a potential vehicle for chemotheraputic agents and radionucleotides in the management of gynecologic neoplasms, Am. J. Obstet. Gynecol., vol. 139, No. 8, pp. 877–888, 1981.*
Bist et al. (1997) *Proc. Natl. Acad. Sci. USA*, 94(20):10693–10698.
Bretscher & Munro (1993) *Science*, 261:1280–1281.
Castro & Fielding (1988) *Biochemistry*, 27:25–29.
Chege & Pfeffer (1990) *J. Cell Biol.*, 111:893–899.
Conrad et al. (1995) *J. Cell Biol.*, 131:1421–1433.
Coxey et al. (1993) *J. Lipid Res.*, 34:1165–1176.
Cullis & Hope (1991) In *Biochemistry of Lipids, Lipoproteins and Membranes* (Vance, D.E. & Vance, J., Eds.) pp. 1–41, Elsevier Press, Amsterdam.
Cupers et al. (1994) *J. Cell Biol.*, 127:725–735.
Dupree et al. (1993) *EMBO J.*, 12:1597–1605.
Emmelot et al. (1964) *Biochim. Biophys. Acta.*, 90:126–145.
Engelman et al. (1997) *J. Biol. Chem.*, 272(26):16374–16381.
Engelman et al. (1999) *FEBS Letters*, 448:221–230.
Feron et al. (1999) *J. Clin. Invest.*, 103(6):897–905.
Fielding et al. (1981) *Proc. Natl. Acad. Sci. USA*, 78:3911–3914.
Fielding et al. (1984) *Proc. Natl. Acad. Sci. USA*, 81:2512–2516.
Fielding & Fielding (1986) *J. Biol. Chem.*, 261:5233–5236.
Fielding et al. (1991) *Biochemistry*, 30:8551–8557.
Fielding (1992) *FASEB J.*, 6:3162–3168.
Fong et al. (1989) *Biochim. Piophys. Acta.*, 1004(1):53–60.
Francone et al. (1990) *J. Lipid Res.*, 31:2195–2200.
Furuchi et al., (1993) *J. Biol. Chem.*, 268:27345–27348.
Goldstein & Brown (1974) *The Journal of Biological Chemistry*, 249:5153–5162.
Goldstein et al. (1978) *Proc. Natl. Acad. Sci. USA*, 75:1877–1881.

(List continued on next page.)

*Primary Examiner*—Anthony C. Caputa
*Assistant Examiner*—Jennifer Hunt
(74) *Attorney, Agent, or Firm*—The Law Offices of Jonathan Alan Quine; Tom Hunter

(57) ABSTRACT

This invention provides a novel intracellular recycling free cholesterol pathway whose activity is required for cell division. The pathway provides the cholesterol needed for cell division prior to separation of daughter cells (mitosis). The new pathway offers several targets from pharmaceutical intervention, either via small molecules (such as sterol analogs) or by molecular engineering (preventing the cell from accumulating cholesterol by promoting free cholesterol efflux by transfection of caveolin cDNA).

9 Claims, 21 Drawing Sheets

OTHER PUBLICATIONS

Goldstein et al. (1985) *Ann. Rev. Cell Biol.*, 1:1–39.
Gottlieb et al. (1993) *J. Cell Biol.*, 120:695–710.
Hansen et al. (1993) *J. Cell Biol.*, 121:61–72.
Havel et al., (1954) *J. Clin. Invest.*, 34:1345–1353.
Heider & Boyett (1978) *J. Lipid Res.*, 19:514–518.
Hokland et al. (1993) *J. Biol. Chem.*, 268:25343–25349.
Huang et al. (1993) *Arterioscler. Thromb.*, 13:445–458.
Johnson et al. (1991) *Biochim. Biophys. Acta.*, 1085:273–298.
Kawano et al. (1993) *Biochemistry*, 32:5025–5028.
Klein et al. (1978) *Biochim. Biophys. Acta.*, 506(1):42–53.
Ktistakis et al. (1992) *Nature*, 356:344–346.
Lange (1994) *J. Biol. Chem.*, 269:3411–3414.
Larkin et al. (1983) *Cell*, 33:273–285.
McCloskey et al. (1987) *Biochim. Biophys. Acta.*, 921:320–332.
Miida et al. (1990) *Biochemistry*, 29:10469–10474.
Montesano et al. (1982) *Nature*, 296:651–653.
Murakami et al. (1990) *J. Neurosurgery*, 73(5):760–767.
Oram et al. (1991) *Arterioscler. Thromb.*, 11:403–414.
Pearse (1976) *Proc. Natl. Acad. Sci.* USA, 73:1255–1259.
Pearse & Robinson (1990) *Ann. Rev. Cell. Biol.*, 6:151–171.
Pedersen & Carafoli (1987) *Trends Biochem. Sci.*, 12:146–150.
Pfeffer (1991) *Cell Biophys.*, 19:131–140.
Ranganathan et al., (1989) *Biochemistry and Cell Biology*, 67(10):719–723.
Reaven et al. (1986) *J. Clin. Invest.*, 77:1971–1984.
Rothberg (1995) *Meth. Enzymol.*, 250:669–679.
Rothman & Schmit (1986) *Cell*, 46:5–9.
Shechter et al. (1981) *J. Lipid Res.*, 22:63–71.
Sola et al. (1993) *Arterioscler. Thromb.*, 13(7):958–966.
Steck et al. (1988) *J. Biol. Chem.*, 263:13023–13031.
Steinman et al. (1976) *J. Cell Biol.* 68:665–687.
Suckling & Stange (1985) *J. Lipid. Res.*, 26:647–671.
Tagaya et al. (1993) *J. Biol. Chem.* 268:2662–2666.
Thyberg & Moskalewski (1992) *J. Cell. Sci.* 103:1167–1175.
Voyno–Yasenetskaya et al. (1993) *Proc Natl. Acad. Sci. USA*, 90L4256–4260.
Woodman & Warren (1991) *J. Cell. Biol.*, 112:1133–1141.
PCT International Search Report, PCT/US99/05146, Jun. 3, 1999.

\* cited by examiner

```
                                      ATAATTCTACAATTATAAACATTTTGTGTATTTTGCAAAATATGGCTA
ACCTGTTGGCTAAAATTCCATTGTTCCAGAAAATATCGGTAATAAATTATAGAAAAGTTAAAGATCTTCATTTCTTATTCGAAGCG
TTTGGAGACATTTCAGAACGGATGGAAATTCTGCCTGCTTAAGTTCCATCCACACCGACTAGATGTAAACGAG
TGTCACCAAAAGTACACCACCAGGCACCCACAGATTCCTTCCATAAGGATCCACAAAGTTTAGATGTAAATGTACCTAAAGTTCCT
AGCCGTCTTTCATCCCTCCCTCTGTGAAACAGGGAACACATGTGTTTAAGGCAGAGATGGAACTTGGGCATGGGAGGGGTGGGGAG
GTGGAAGGGACGGCTTAGGACAGGGCAGGATTGTGATTGTTCTCGCCGGCATCTCTGCAGGCGCGTC
GGCTCCCTCCACCCCTGCTGAGATGATGCACTGCGAAAACATTCGCTCTCCCGGGACGCCTCTCGGTGCTTCGCTGCGCCTCCCCCCCT
GTTGCCTCAGGTAAAATAATCTGCCCAAGCACCCCAGGGGCCAACGGCAGACAAACCTTTGCGGGCGGC
CTGCTGCCAGAACCTTGGGATGTGCCTAGACCCCCCCCAGCGCTCCCCCCATACAATACAAGATCTTCCTCCTCAGTTCCCTTAA
CAGGAGGGCTCCCTCCCAGCCCACACCCCCAGCCCCACAGTTTCATCCACCAGCATGTCTGGGGCAAATACGTAGACTCGGAGGTAGGCAT
AGCACAGCCCAGGAAACCTCCTCACAGTTTCATCCACCAGCATGTCTGGGGCAAATACGTAGACTCGGAGGTAGGCAT
CCGTGGGGGCGCCGGGCGCCGGGGTCGGGGCGTGCCGGGG
```

FIG. 14A.

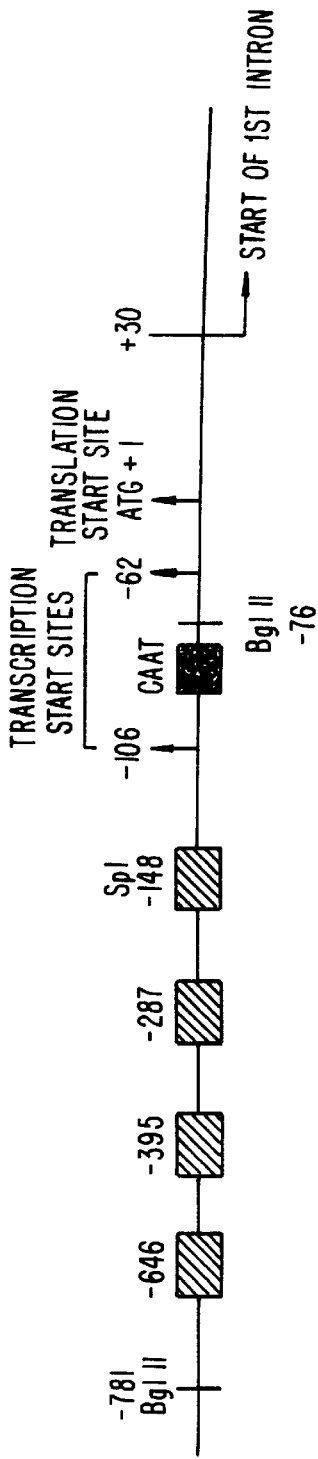

FIG. 14B.

REGULATION OF THE CELL CYCLE BY STEROLS

CROSS-REFERENCE TO RELATED APPLICATIONS

This application claims benefit under 35 U.S.C. §119(e) of provisional application U.S. Ser. No. 60/077,351, filed on Mar. 9, 1998, which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. HL 14237 and Grant No. HL 57976 awarded by the National Institutes of Health. The Government of the United States of America may have certain rights in this invention.

FIELD OF THE INVENTION

This invention relates the discovery that an increase in cellular free cholesterol is a requirement for cell division. The cellular free cholesterol concentration is regulated by ATPase-mediated selective uptake from low density lipoproteins (LDLs) and by caveolin-mediated efflux. These two processes thus provide good targets for screening of compounds that exert anti-mitotic activity through modulation of cellular free cholesterol.

BACKGROUND OF THE INVENTION

The cell division cycle is one of the most fundamental processes in biology which, in multicellular organisms, ensures the controlled generation of cells with specialized functions. Under normal growth conditions, cell proliferation is tightly regulated in response to diverse intra- and extracellular signals. This is achieved by a complex network of proto-oncogenes and tumor-suppressor genes that are components of various signal transduction pathways.

Numerous diseases are characterized by abnormal cell mitosis. For example, uncontrolled cell mitosis is a hallmark of cancer. In this instance, activation of a proto-oncogene(s) and/or a loss of a minor suppressor gene(s) can lead to the unregulated activity of the cell cycle machinery. This leads to unregulated cell proliferation and to the accumulation of genetic errors which ultimately will result in the development of cancer (Pardee (1989) *Science* 246: 603–608).

Many cancers are also classified as angiogenesis dependent diseases ((i.e., those diseases which require or induce vascular growth). In addition to unregulated growth of the tumor body itself, cancers are typically characterized by the ingrowth of vasculature which provide various factors that permit continued tumor growth. Thus, both the vascular tissue as well as the cancer itself have proven to be attractive targets for anti-mitotic agents in the treatments of various neoplasias.

In addition, unregulated cell mitosis is a hallmark of a number of other pathological conditions. For example, cell mitosis is important for the normal development of the embryo, formation of the corpus luteum, wound healing, inflammatory and immune responses, and, as indicated above, angiogenesis and angiogenesis related diseases.

Consequently the use of anti-mitotic compounds to regulate cell proliferation and thereby introduce control over disease states characterized by unregulated mitotic activity has sparked considerable interest.

Cell mitosis is a multi-step process that includes cell division and replication (Alberts, et al. (1989) *In The Cell*, pp. 652–661; Stryer (1988) *Biochemistry*). Mitosis is characterized by the intracellular movement and segregation of organelles, including mitotic spindles and chromosomes. Microtubule formation is important for cell mitosis, cell locomotion, and the movement of highly specialized cell structures such as cilia and flagella.

As microtubules and microtubule-related structures are intimately involved in the mitotic process, they have provided a convenient target for putative anti-mitotic compounds. Indeed, microtubules have proven to be extremely labile structures that are sensitive to a variety of chemically unrelated anti-mitotic drugs. For example, colchicine and nocadazole are anti-mitotic drugs that bind tubulin and inhibit tubulin polymerization (Stryer (1988) *Biochemistry*). When used alone or in combination with other therapeutic drugs, colchicine has been used to treat cancer (WO9303729; J03240726-A), alter neuromuscular function, change blood pressure, increase sensitivity to compounds affecting sympathetic neuron function, depress respiration, and relieve gout (*Physician's Desk Reference*, (1993) 47: 1487).

Estradiol and estradiol metabolites such as 2-methoxyestradiol have also been reported to inhibit cell division and in particular, tubulin polymerization (Seegers et al. (1989) *J. Steroid Biochem.* 32: 797–809; Lottering et al. (1992) *Cancer Res.* 52: 5926–5923; Spicer et al. (1989) *Mol. and Cell. Endo.* 64: 119–126; Rao et al. (1967) *J. Exp. Cell Res.* 48: 71–81). However, the activity is variable and depends on a number of in vitro conditions. For example, estradiol inhibits cell division and tubulin polymerization in some in vitro settings (Spicer et al. (1989) *Mol. and Cell. Endo.* 64: 119–126; Ravindra (1983) *J. Indian Sci.* 64(c)), but not in others (Lottering et al. (1983) *Cancer Res.* 52: 5926–5923; Ravindra, (1983) *J. Indian Sci.* 64(c)).

Of most widespread and recent interest, however, are compounds with paclitaxel-like activity. These include, but are not limited to paclitaxel and paclitaxel derivatives and analogues (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506). Paclitaxel and its derivatives are compounds that inhibit eukaryotic cell replication by enhancing polymerization of tubulin moieties into stabilized microtubule bundles that are unable to reorganize into the proper structures for mitosis (Id.). Paclitaxel and paclitaxel-like compounds have shown significant efficacy.

While the above-identified and other anti-mitotic agents have proven useful in a variety of clinical settings, these agents operate through essentially a single modality; interference with the formation or operation of the mitotic apparatus (e.g., mitotic spindle). One would expect, however, that such compounds may show increased efficacy when coupled with anti-mitotic compounds that act through one or more different modalities.

SUMMARY OF THE INVENTION

This invention provides new methods of inhibiting the growth and/or proliferation of cells, more particularly the growth and proliferation of cancer cells, other transformed cells, or cells at other sites, such as in aortic transplant subject to restenosis. The methods of this invention are premised, in part, on the discovery that for cell division (mitosis) to proceed beyond S-phase, a doubling of cell cholesterol content must be initiated and completed. It was a discovery of this invention that this increase is dependent upon both upregulation of ATPase-dependent uptake of free cholesterol (FC) from low density lipoprotein (selective FC uptake) and the down-regulation of caveolin expression associated with a decrease in efflux. These steps represent the two termini of a novel free cholesterol (FC) recycling pathway described herein.

It was a discovery of this invention that cell division can be inhibited when free cholesterol accumulation is prevented. This can be achieved either by inhibiting free cholesterol uptake with inhibitors of cell surface $H^+$-ATPase or by promoting free cholesterol (FC) efflux via caveolin overexpression. This pathway described herein thus offers two novel sites to regulate cell proliferation.

Thus, in one embodiment, this invention provides methods of identifying an anti-mitotic agent. The methods involve contacting a cell with an agent to be tested for anti-mitotic activity, and detecting the efflux of free cholesterol from said cell. An increase in efflux of free cholesterol by from the cell when contacted by said agent as compared to the efflux from the cell under the same conditions lacking the agent (e.g., a statistically significant increase, preferably at least a 10% increase, more preferably at least a 25% increase, and most preferably at least a 50%, 100% or even at least a 200% increase) indicates that the agent is has antimitotic activity (or that the agent is likely to have antimitotic activity and thus is a good candidate for further evaluation (i.e., is a good lead candidate). The assay can involve detecting the efflux of labeled (e.g., [$^3$H]-labeled) free cholesterol. In addition to, and/or in alternative to this method, the detection can involve detection of the expression of a reporter gene operably linked (under the control of) a caveolin promoter. Virtually any reporter gene is suitable, however, in a preferred embodiment, the reporter gene is selected from the group consisting of a glucuronidase, bacterial chloramphenicol acetyl transferase (CAT), beta-galactosidase (β-gal), a firefly luciferase gene FFlux, and green fluorescent protein. Alternatively, the detection can involve detection of the transcription level of a caveolin mRNA (e.g., in a Northern blot, by PCR, etc.) and/or the amplification of a caveolin DNA.

The assay can optionally be performed in the presence of a low density lipoprotein (LDL). Virtually any cell is suitable, however preferred cells are mammalian and most preferred cells include a cell selected from the group consisting of a fibroblast, a vascular smooth muscle cell, a vascular endothelial cell, a macrophage, a hematopoietic cell, a liver cell, a kidney cell, and an intestinal mucosal cell.

In another embodiment, this invention provides methods of identifying an anti-mitotic agent that acts through the cholesterol uptake aspects of the LDL-FC pathway. The methods involve contacting a cell with an agent to be tested for anti-mitotic activity in the presence of a low density lipoprotein; and detecting the internalization of free cholesterol by the cell. A decrease (e.g., a statistically significant decrease, preferably at least a 10% decrease, more preferably at least a 25% decrease, and most preferably at least a 50% decrease) in internalization of free cholesterol by the cell when contacted by the agent as compared to the internalization of free said the cell under the same conditions lacking said agent indicates antimitotic activity of said agent. In one embodiment, the low density lipoprotein (LDL) comprises a labeled (e.g., a [$^3$H]-labeled) cholesterol. The detecting can involve detecting the presence, absence, or amount of the labeled cholesterol in the cell. One method of such detection involves quantifying the amount of a cholesterol transport vesicle produced by the cell. Preferred cells for this assay are selected from the group consisting of a fibroblast, a vascular smooth muscle cell, a vascular endothelial cell, a macrophage, a hematopoietic cell, a liver cell, a kidney cell, and an intestinal mucosal cell.

In another embodiment, this invention provides an isolated caveolin promoter. The promoter comprises at least two SRE-like 10 base sites having at least 50% sequence identity with the 10 base steroid receptor element (SRE) (ATCACCCCAC) of the LDL receptor protein. In addition, the promoter upregulates transcription of a downstream (operably linked) gene in the presence of free cholesterol. The promoter can further include an Sp1 consensus sequence (CCGCCC). In a preferred promoter, a transcriptional start site is at −62 bp and at −106 bp when the translational start site is designated as +1. The first SRE-like sequence is preferably located at about −646 bp preferably and a second SRE-like promoter is at about −395 bp. The promoter can comprise an SpI consensus sequence (CCGCCC) at about −148 bp. The promoter can also comprise a CAAT sequence at −84 bp. The caveolin promoter can also comprising a nucleotide sequence that hybridizes with the sequence of FIG. 14a and has a SPE-like sequence at about −646 bp and at about −395 bp. One particularly preferred caveolin promoter has the sequence of FIG. 14a, wherein the SPE-like sequence at −287 bp is optionally excised. It will be appreciated that the positions specified in base pairs can be routinely varied without significant effect. Thus, the term "about" in this context refers to an approximate location (e.g, ±5 bp, preferably ±10 bp, more preferably ±20 bp, and most preferably ±30, ±40, or even ±50 bp).

In another embodiment, this invention provides a cell useful for screening for antimitotic activity of a test agent. The cell comprises reporter gene under the control of any of the caveolin promoters described herein. In one embodiment, the reporter gene is selected from the group consisting of a glucuronidase, bacterial chloramphenicol acetyl transferase (CAT), beta-galactosidase (β-gal), a firefly luciferase gene FFlux, and green fluorescent protein. The cell can be a cell selected from the group consisting of a fibroblast, a vascular smooth muscle cell, a vascular endothelial cell, a macrophage, a hematopoietic cell, a liver cell, a kidney cell, and an intestinal mucosal cell.

In still another embodiment, this invention provides a vector comprising any of the caveolin promoters described herein and a restriction site downstream from said promoter such that a gene or cDNA inserted into the restriction site is operably linked to the promoter. The gene or cDNA can be a reporter gene or cDNA (e.g., a gene or cDNA selected from the group consisting of a glucuronidase, bacterial chloramphenicol acetyl transferase (CAT), beta-galactosidase (β-gal), a firefly luciferase gene FFlux, and green fluorescent protein).

This invention also provides a reporter construct comprising a reporter gene or cDNA operably linked to any one of the caveolin promoters described herein. In one preferred embodiment, the reporter gene or cDNA is selected from the group consisting of a glucuronidase, bacterial chloramphenicol acetyl transferase (CAT), beta-galactosidase (β-gal), a firefly luciferase gene FFlux, and green fluorescent protein.

This invention also provides methods of inhibiting cell division. In one embodiment, the methods involve inhibiting an increase in free cholesterol in a cell. The inhibiting can involve inhibiting the uptake of free cholesterol from a low density lipoprotein (LDL). In one embodiment, this may be by contacting the cell with a compound that binds vesicular ATPase at an ATP binding region. A preferred ATP binding region is selected form the group consisting of LLYGP-PGCGKTLLAR (SEQ ID NO: 1) and LFYGPPGCGKTL-LAK (SEQ ID NO: 2). The method can comprise contacting said cell with N-ethylmaleimide.

In another preferred embodiment, the methods involve increasing the expression level of a caveolin gene.. In a particularly preferred embodiment, the increased expression of a caveolin gene (or introduction of exogenous caveolin or recombinant expression of heterologous caveolin gene or cDNA) is sufficient to prevent an increase of free cholesterol in the cell during mitosis. The method can involve upregulating the expression of an endogenous caveolin gene, and/or transfecting the cell with a construct (e.g. expression cassette) encoding a caveolin gene, and/or introducing exogenous caveolin. Preferred nucleic acids encoding caveolin include, but are not limited to nucleic acids encoding a human caveolin gene or cDNA. In a particularly preferred embodiment the caveolin gene or cDNA is under the control of a caveolin promoter.

In another embodiment, this invention provides methods of diminishing cellular free cholesterol. The methods involve increasing the expression level of a caveolin gene. The increase can be by upregulating the expression of an endogenous caveolin gene. Alternatively, the increase can be by transfecting the cell with a construct encoding a caveolin gene, preferably with a human caveolin gene. The caveolin gene is preferably under the control of a caveolin promoter.

Definitions

The following abbreviations are used herein: LDL, low-density lipoprotein; HDL, high-density lipoprotein; FC, free cholesterol; EC, esterified cholesterol; NEM, N-ethylmaleimide; SRE, sterol receptor element.

Free cholesterol (FC) is cholesterol that not esterified to a fatty acid chain, but rather exists as the free alcohol. In contrast, esterified cholesterol (EC) is cholesterol that is joined (esterified) to a fatty acid.

"Substantial inhibition" of the LDL-FC pathway, or of cholesterol transport vesicle formation, by a particular agent, refers to a significant decrease in the influx of free cholesterol or in the formation of cholesterol transport vesicles by a cell contacted with that agent as compared to the same type of cell under the same conditions, but in the absence of the agent. Substantial inhibition is at least about 50% decrease, preferably at least about a 60% decrease, more preferably at least about a 70% a decrease and most preferably at least about an 80% decrease in free cholesterol influx (e.g. as measured by the transport of labeled FC from LDLs) or in the rate of formation or the amount of cholesterol transport vesicles.

Lipoproteins are complexes or compounds containing lipid and protein. Lipoproteins are found in plasma and have been historically characterized by their flotation constants (densities) with low density lipoproteins (LDLs), ranging from about 1.019 g/ml to about 1.063 g/ml, and high density lipoproteins (HDLs), ranging from about 1.063 g/ml to about 1.21 g/ml. However, more recently it has been recognized that, particularly in various pathological conditions the lipid composition may vary and LDLs and HDLs can deviate from these ranges. Thus, LDLs and HDLs are also characterized in terms of the principle protein. LDLs typically contain apolipoprotein B as the only, or as the principle (greater than 50% of the protein content of the lipoprotein) protein of the LDL. In contrast, HDLs contain apolipoprotein A-I as the only, or principle protein, of the lipoprotein.

The term "internalization" when used in reference to free cholesterol, refers to the transport of free cholesterol from the external plasma membrane of the cell into the cytoplasm. Typically internalization involves invagination of the plasma membrane and subsequent formation of a vesicle. The cholesterol thus internalized may be in the form of free cholesterol (FC) or it may be esterified (EC).

The term "cholesterol transport vesicle", as used herein, refers to a vesicle whose production is mediated by the LDL-FC cholesterol transport pathway. The formation of cholesterol transport vesicles is inhibited by vesicular ATPase inhibitors such as N-ethylmaleimide (NEM) and nitrate ion (e.g., $KNO_3$), but not by forskolin, isobutyl methylxanthine, progesterone, azide, or vanadate. The formation of cholesterol transport vesicles of this invention is also inhibited by hyperosmotic media, reduction or elimination of $K^+$, cytochalasin, monensin, or bafilomycin, but not by brefeldin A, vinblastine, nocodazole, or taxol (e.g., at up to 60 mM concentration). The cholesterol transport vesicles may store cholesterol either as free cholesterol (FC) or as esterified cholesterol (EC). Because the cholesterol transport vesicles are enriched for cholesterol, as compared to other intracellular membranes, the transport vesicles have a reduced density ranging from about 1.05 g/ml to about 1.12 g/ml, more preferably from about 1.06 g/ml to about 1.10 g/ml and most preferably from about 1.07 to about 1.09 g/ml. Cholesterol transport vesicles can be readily identified by placing cells in media containing labeled LDL free cholesterol and then detecting the presence of the label in the vesicles as described herein.

A vesicle is said to be "enriched" for free cholesterol when the concentration of free cholesterol of the vesicle is greater than that of other types of vesicles found in the cell or is greater than that of the region of the plasma membrane from which the vesicle originates. In the instant case, cholesterol transport vesicles originate from coated pits; areas of the plasma membrane that contain virtually little free cholesterol and yet the transport vesicles contain more cholesterol than other vesicle types found within the cell. Vesicles so enriched can be distinguished from other vesicles and intracellular membranes by the fact that, due to the higher cholesterol content, the enriched vesicles have a lower density and therefore float at a higher point in a density gradient than other intracellular membranes.

The term "cholesterol uptake" as used herein refers to the net accumulation of cholesterol by a cell. As explained herein, cells acquire cholesterol from low-density lipoproteins and lose cholesterol to high-density lipoproteins. In addition, cells sequester cholesterol in an intracellular compartment (e.g., the cholesterol transport vesicle) via the LDL-FC pathway of this invention. As the cholesterol content of the plasma membrane is tightly regulated, an increase in cholesterol internalization leads to an increase in total cellular cholesterol (an increase in cholesterol uptake), while, conversely, a decrease in cholesterol internalization leads to a decrease in total cellular cholesterol (a decrease in cholesterol uptake).

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. The promoter also optionally includes distal enhancer or repressor elements which can be located as much as several thousand base pairs from the start site of transcription. A "constitutive" promoter is a promoter which is active under most environmental conditions and states of development or cell differentiation. An "inducible" promoter responds to an extracellular stimulus. The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "caveolin promoter" as used herein refers to a promoter that, in its native state, regulates the expression of a caveolin gene, more preferably expression of a caveolin 1 gene. The term caveolin promoter, however, is intended to include modified or non-native caveolin promoters characterized by the fact that they upregulate expression of a gene under their control in the presence of increased free cholesterol.

The term "caveolin" refers to a member of the caveolin gene family. The caveolin gene family is characterized by caveolin 1, the largest and first identified product of the caveolin gene family, contains 178 amino acids and is coded by a 2.2 kb mRNA (Glenney (1992) *FEBS Lett.*, 314: 45–48, Scherer et al. (1995) *J. Biol. Chem.*, 270: 16395–16401).

"Caveolae" are invaginated cell-surface microdomains (60–80 nm diameter) expressed in many quiescent peripheral cells (Parton et al. (1995) *Science*, 269: 1398–1399). Caveolae are clathrin-free surface invaginations shown in intact cells by electron microscopy to be rich in free cholesterol, sphingolipids and GPI-anchored proteins. Caveolar free cholesterol is uniquely accessible to cholesterol oxidase in unfixed cells. Caveolin, a lipid binding protein, has been shown to be associated with caveolae in several cell lines, including fibroblasts, and in caveolar membrane fractions purified from these cells.

The terms "isolated" "purified" or "biologically pure" refer to material which is substantially or essentially free from components which normally accompany it as found in its native state.

The terms "identical" or percent "identity," or percent "homology" in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "detectable label" is used herein to refer to any composition detectable by spectroscopic, photochemical, biochemical, immunochemical, electrical, optical or chemical means. Such labels include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Preferred detectable labels, for use in this invention, do not alter the cellular processing of the compound to which they are bound. Thus, preferred free cholesterol labels do not alter transport of free cholesterol by the LDL-FC pathway of this invention. Similarly, preferred labels do not substantially alter the gross physical properties of the labeled component. In particular, preferred labels do not substantially alter the density of the: lipid to which they are joined. Thus, radioactive labels (e.g., $^3H$, $^{125}I$, $^{35}S$, $^{14}C$, or $^{32}P$) are most preferred for use in the present invention.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The following abbreviations are used herein: FC, free cholesterol; CE, cholesteryl ester; LDL, low density lipoprotein; HDL, high density lipoprotein; GAPD, glyceraldehyde 3-phosphate dehydrogenase.

BRIEF DESCRIPTION OF THE DRAWINGS

FIGS. 14a and 14b illustrate the caveolin promoter. FIG. 14a shows the 5'-flanking region, exon 1, and part of intron 1 of the human caveolin gene sequence. FIG. 14b shows the promoter structure of the caveolin gene. Three potential SREs (labeled 1, 2 and 3) are in bold face. The Sp1 consensus site is in bold face underlined. The translational ATG start site is shown double underlined. Transcriptional start sites, determined by RACE, are shown by arrows.

FIG. 20A shows FC mass following release from aphidicolin-mediated cytostasis in sham-transfected cells (closed circles) and caveolin cDNA-tnansfected cells (open circles). FIG. 20B shows the proportion of total cell FC accessible to cholesterol oxidase under the same conditions in sham-transfected cells (closed circles) and caveolin cDNA-transfected cells (open circles). FIG. 20C shows cell number 32 h following removal of aphidicolin. Initial cell number (zero time) was 3.4×10$^5$ cells. Con, sham-transfected cells; +cDNA, cells transfected with caveolin cDNA.

DETAILED DESCRIPTION

Figure 1:
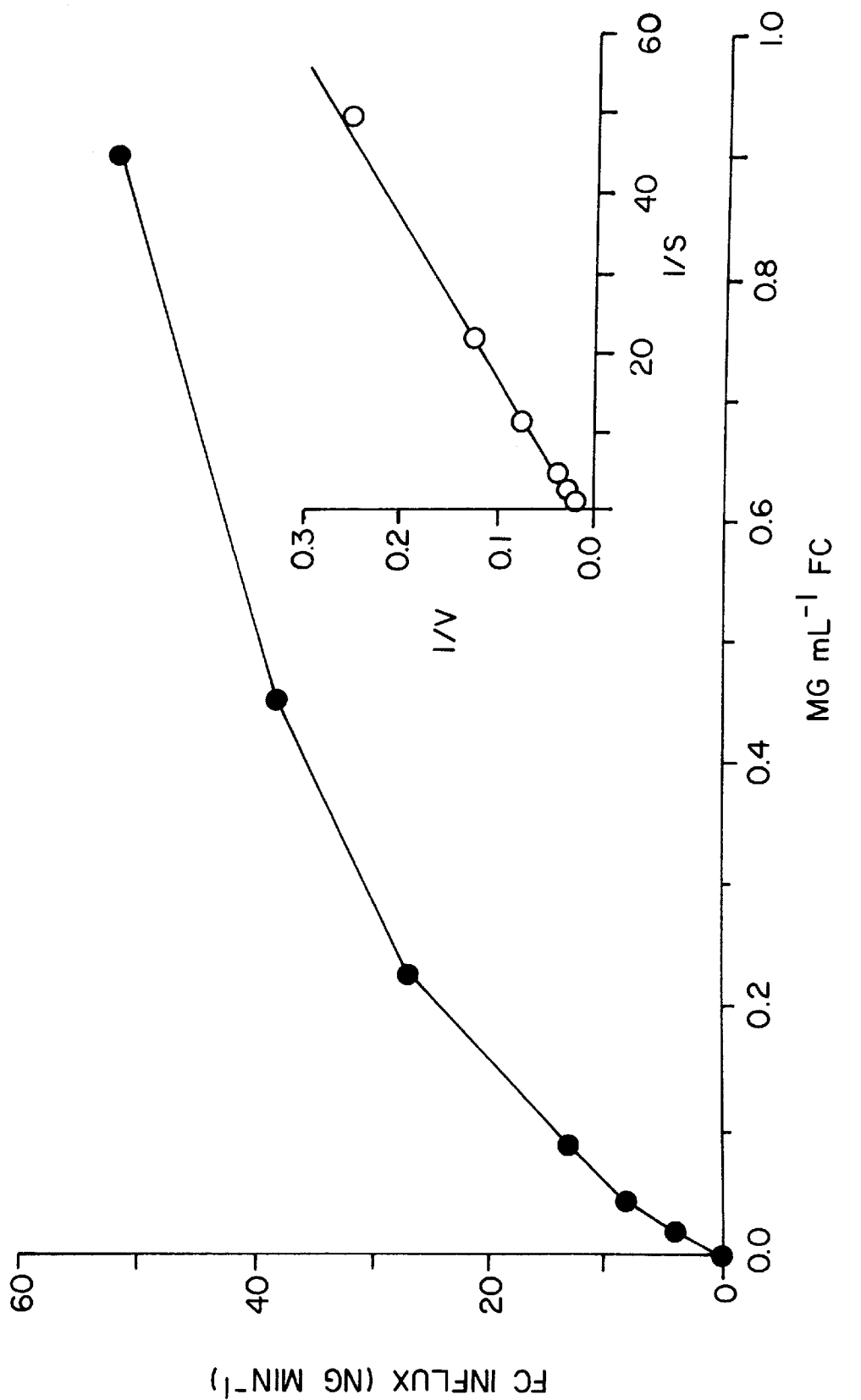
FIG. 1 illustrates the concentration dependence of LDL $^3H$-FC uptake by fibroblast monolayers. Unlabeled monolayers equilibrated with 7% plasma-DMEM were washed with PBS (×4), incubated (10 min, 37° C.) with LDL at the indicated concentration, then washed with PBS-albumin (4 mg ml$^{-1}$), then with PBS (×4). The washed monolayers were then extracted as described herein and cell-associated label determined. Each data point represents the mean of triplicate dishes. Insert: double reciprocal plot of the experimental data.

This invention provides new methods of inhibiting the growth and/or proliferation of cells, more particularly the growth and proliferation of cancer cells, other transformed cells, or at other sites, such as in aortic transplant subject to restenosis. The methods of this invention are premised, in part, on the discovery that for cell division (mitosis) to proceed beyond S-phase, an increase (i.e., doubling) of cell cholesterol content must be initiated and completed. It was a discovery of this invention that this increase is dependent on a cholesterol pathway characterized at the "input" by upregulation of ATPase-dependent uptake of free cholesterol (FC) from low density lipoprotein (selective FC uptake) and at the "output" by the down-regulation of caveolin expression associated with a decrease in efflux. These steps thus represent the two termini of a novel free cholesterol (FC) recycling pathway described herein.

It was a discovery of this invention that cell division can be inhibited when free cholesterol accumulation is prevented. This can be achieved by inhibiting either endpoint of the free cholesterol pathway described above. For example, this can be achieved either by inhibiting free cholesterol uptake with inhibitors of cell surface H$^+$-ATPase or by promoting free cholesterol (FC) efflux via caveolin overexpression. This pathway, mediating the ATPase-dependent uptake of free cholesterol low density lipoprotein and its ultimate efflux from coated pits, thus offers two novel sites to regulate cell proliferation.

These sites offer convenient means to assay for agents that act to interfere with the accumulation of free cholesterol by a cell during mitosis. In one embodiment, assays are provided to identify agents that inhibit (e.g, downregulate or eliminate) mitosis by inhibiting ATPase-mediated free cholesterol influx from low density lipoprotein. In another embodiment assay are provided to identify agents that inhibit mitosis by increasing cholesterol efflux (e.g, through upregulation of caveolin expression and the resulting increase in coated pit formation.

With respect to cholesterol regulation through efflux regulation, it was a discovery of this invention that free cholesterol efflux is upregulated when expression of the caveolin gene is upregulated. Thus, as demonstrated in the examples, overexpressing caveolin n normal human skin cells (a model for human peripheral cells in general) greatly inhibited cell division by starving the cells of cholesterol needed to complete the cell cycle. The cholesterol is lost from the cell in a form in which it cannot easily reenter the cells. The growth inhibition obtained is at least as great as other current approaches using antisense DNA to target cell cycle proteins and has great potential in treating "transplant sickness" in cardiovascular surgery where smooth muscle cells at graft sites multiply inappropriately.

In addition, the same phenomenon has been shown in a human cancer cell model (human breast cancer-derived MCF-7 cells). Overexpression of caveolin blocks cell division in cancer cells.

The caveolin gene and/or its promoter provide good targets for modulation of cellular cholesterol and consequently a good targets for anti-mitotic agents. Thus, in one embodiment, assays are provided for identifying agents that can up- or down-regulate caveolin gene expression. In one particular embodiment, the assays utilize a reporter gene under the control of a caveolin promoter to assay for alterations in caveolin expression.

I. The LDL-FC Transport Pathway

This invention relates to the discovery of a new pathway by which free cholesterol (FC) from low-density lipoproteins (LDLs) is bound and preferentially (selectively) internalized by mammalian cells. This pathway (designated herein as the LDL-FC pathway) accounts for a major part of the free cholesterol influx required to maintain free cholesterol levels in the plasma membrane in response to the high level of free cholesterol efflux (mainly to high-density lipoproteins HDLs) under normal physiologic conditions (see, also, copending U.S. Ser. No. 08/740,444, filed on Oct. 29, 1996). This pathway is thus an important component in the regulation of cellular cholesterol levels and abnormal function of this pathway is believed to result in pathological states characterized by abnormal cellular cholesterol levels. Conversely, manipulation of this pathway, e.g., by the administration of drugs that up-regulate or down-regulate FC internalization, offers a previously unknown and unsuspected approach to the treatment of such pathologies and to the regulation of cellular mitosis.

The low-density lipoprotein free cholesterol (LDL-FC) pathway of this invention is responsible for cholesterol increase associated with, and necessary for, mitotic activity. The LDL-FC pathway of this invention is characterized by two clearly delineated endpoints. The first endpoint (the cholesterol intake point) is the ATPase-mediated selective uptake of free cholesterol from low density lipoproteins (LDLs) substantially without accompanying protein or other lipid. The second endpoint (the cholesterol efflux point) is free cholesterol efflux at coated pits mediated by caveolin upregulation. These two endpoints provide unique targets for screening for agents that have activity in regulating this pathway and thus in altering (e.g., inhibiting) the cell cycle.

A) LDL-FC Pathway Starting Point: Free Cholesterol Intake from Low Density Lipoprotein The low-density lipoprotein free cholesterol (LDL-FC) pathway of this invention is responsible for cholesterol increase associated with, and necessary for, mitotic activity. The LDL-FC pathway is a low affinity, high capacity cholesterol transport pathway by which free cholesterol is selectively taken up from LDLs substantially without accompanying protein or other lipid. The free cholesterol thus taken up is ultimately incorporated (sequestered) in an intracellular compartment, more particularly into a "cholesterol transport vesicle" where it may ultimately be esterified. The high cholesterol uptake capacity provided by this pathway indicates that it an important component in cellular regulation of cholesterol.

In properties and mechanism the LDL-FC pathway of this invention differs substantially from previously described lipid-transport pathways. For example, in one previously known pathway, the intact LDL, including LDL cholesterol, LDL protein, and LDL esterified cholesterol, was endocytosed in toto (Goldstein et al., *Ann. Rev. Cell. Biol.*, 1: 1–39 (1985)). In contrast, the LDL-FC pathway of this invention, the free cholesterol uptake was selective and almost unaccompanied by the uptake of LDL protein or LDL cholesteryl ester mass. Unlike receptor-mediated endocytosis, the LDL-FC pathway was similar in normal fibroblasts and several lines of LDL receptor-deficient cells. Finally, in contrast to receptor-mediated endocytosis which is a high affinity low capacity pathway, the LDL-FC pathway of this invention is a low-affinity, high capacity pathway whose rate varies strongly with medium LDL levels over the physiological range.

Both the LDL-FC pathway of this invention and the receptor mediated endocytosis pathway are inhibited by heparin. It is unlikely this represents a similarity between the two pathways, but, without being bound to a particular theory, probably reflects, in each case, formation of soluble charged complexes of LDL and heparin which are less reactive with the cell surface.

Consistent with observations reported herein in Example 1, Slotte et al., *Biochem. J.*, 222: 821–824 (1984), reported uptake and esterification of LDL-FC label by LDL receptor-deficient fibroblasts. However, this study only addressed LDL-FC uptake in abnormal (receptor deficient) cells. In addition, no measurement was made of cellular FC mass, was made, no inhibition of LDL-FC incorporation was observed and no mechanism of selective LDL-FC incorporation was identified.

The LDL-FC transport pathway of this invention does not reflect the simple exchange of cholesterol at the cell surface, for several reasons. There was a marked increase in cellular FC mass in the absence of HDL; indeed LDL-FC was retained in the cells almost quantitatively. Influx was largely LDL concentration dependent while efflux was HDL concentration dependent. In addition, there was an obvious lag (10 min) between the binding of labeled LDL-FC and its availability for efflux to HDL.

The effects of metabolic inhibitors also confirmed that the LDL-FC influx pathway of this invention differs from other mechanisms of FC transport. In human hepatoblastoma (HepG2) cells, progesterone promoted the transfer of FC from the plasma membrane to the interior of the cell (Lange, *J. Biol. Chem.*, 269: 3411–3414 (1994)). In contrast, progesterone was without effect on influx via the LDL-FC pathway of this invention. Similarly, as was chloroquine, an inhibitor of lysosomal transport that blocks endocytotic processing had no effect on cholesterol influx via the LDL-FC pathway. The transfer of newly-synthesized cholesterol to the plasma membrane of fibroblasts is cAMP-dependent and stimulated by forskalin and IBMX (Hokland et al., *J. Biol. Chem.*, 268: 25343–25349 (1993)), while LDL-FC influx was unaffected by these agents. Finally, LDL-FC influx was blocked by inhibitors specific for an ATPase now broadly implicated in vesicular transport in both yeast and mammalian cells (Pederson & Carafoli, *Trends Biochem. Sci.*, 12: 146–150 (1987); Sollner et al., *Nature*, 362: 318–324 (1993); Ferro-Novick & Jahn, *Nature*, 370: 191–193 (1994)).

ATPases in this family are characterized by resistance to azide and vanadate, and sensitivity to nitrate and NEM. The best-characterized of these enzymes (NEM-sensitive factor, NSF) forms a complex at the inner surface of the plasma membrane with attachment factors and other proteins (Weidman et al., *J. Cell. Biol.*, 108: 1589–1596 (1989)) and plays an essential role in the transfer of solute vesicles between intracellular compartments. ATPases with similar properties have been reported within the plasma membrane.

In LDL-FC transfer, the effect of NEM and $KNO_3$ was to prevent the transfer of free cholesterol away from the plasma membrane to the cell interior. As a result, most of the FC transferred to the cells from LDL remained accessible to plasma lipoproteins, and the initial rate of efflux of FC from prelabeled cells to plasma was increased several-fold. Without being bound to a particular theory, it is believed that the role of the NEM-sensitive factor in LDL-FC influx is to draw free cholesterol into specific plasma membrane microdomains from which it can be either interiorized or effluxed to HDL.

B) LDL-FC Pathway End Point: Export of Free Cholesterol

The endpoint of the LDL_FC pathway of this invention is the efflux of free cholesterol at coated pits. It was a discovery of this invention that this efflux is mediated by an upregulation of the caveolin gene.

Without being bound by a particular theory, it is believed that transcription factor SREBP-1 (first identified as the adipocyte determination and differentiation factor, ADD1, Tontonoz et al. (1993) *Mol. Cell Biol.* 13: 4753–4759) plays a major role. Free cholesterol (e.g., originating from the selective uptake of free cholesterol from LDL) has a consistent inhibitory effect on the cleavage of SREBP (a SREBP-related protein, e.g., SREBP-1). When free cholesterol is low, the mature SREBP fragment would enter the nucleus to bind to one of the sterol regulatory elements SREs) in the caveolin promoter, inhibiting transcription and thereby decreasing the formation of caveoli and consequent efflux of free cholesterol.

The data presented herein suggest that SREBP-1 inhibits caveolin transcription, in contrast to its effects on other free cholesterol-sensitive promoters, although effects of ALLN with other nuclear factors may also be important. Free cholesterol-sensitive genes mediated by the SREBP mechanism have so far involved only the input side of regulation, the endocytosis of LDL or the new synthesis of free cholesterol. In quiescent cells including confluent fibroblasts, the activity of these pathways is very low, yet cellular free cholesterol level was actively regulated at the level of efflux (Parton et al. (1994) *Science* 269: 1398–1399, Fielding et al. (1997) *Proc. Natl. Acad. Sci. USA* 94: 3753–3758). The SRE/SREBP mechanisms, previously shown to regulate free cholesterol influx can regulate both influx and efflux. This finding extends the role of SREBP to quiescent cells and suggests it may coordinate control over all the major pathways of cholesterol homeostasis.

II. Screening for Modulators of Cell Proliferation

As indicated above, the LDL-FC pathway of this invention provides at least two good targets for screening compounds that alter cellular free cholesterol and thus cell division. These targets include the ATPase-mediated selective uptake of free cholesterol from low density lipoproteins (LDLs) and the caveolin-mediated efflux of free cholesterol.

As indicated above, it was a discovery of this invention that cellular free cholesterol must increase in order for proper cell division to occur. Conversely, cell division can be inhibited by limiting the mitosis-associated increase in free cholesterol or by decreasing cellular free cholesterol. Thus, an agent that either inhibits (i.e., reduces or eliminates) free cholesterol influx from LDL via the LDL-FC pathway or increases free cholesterol efflux (e.g., by upregulation of the caveolin gene) will act as a potent anti-mitotic.

It will also be appreciated that screens for mitotic agents or anti-mitotic agents that act through modulation of cellular free cholesterol can also double as screens for compounds that modulate cellular free cholesterol. The assays are performed in essentially an identical manner, the assays for mitotic or anti-mitotic activity reflecting the teaching of this invention that such mitotic or anti-mitotic activity is a function of the requirement for an increase in free cholesterol to facilitate mitosis.

A) Screening for Inhibitors of Inhibition FC Uptake by the LDL-FC Transport Pathway In one embodiment, this invention provides methods of screening for inhibitors and inducers of LDL-FC uptake (e.g., where inhibitors are expected to act as anti-mitotic agents). In a preferred embodiment, the methods involve contacting a cell with a test compound in the presence of low-density lipoprotein and measuring the uptake of free cholesterol by the cell as compared to a similar (control) cell measured without exposure to the test compound. An increase of free cholesterol incorporated into the treated cells as compared to the control cells indicates the test compound has agonistic activity, while conversely, a decrease of detectable label incorporated into the treated cell as compared to the control cell indicates an inhibitory activity. Such inhibitory activity is expected to be anti-mitotic.

Preferred test cells include, but are not limited to, virtually any nucleated mammalian cell, with human cells being more preferred and fibroblasts, human vascular smooth muscle cells, human vascular (e.g., aortic) endothelial cells, macrophages, hemapoietic cells, liver, kidney, and human intestinal mucosal cells being most preferred. It is known that some cells do not naturally express caveolin, but these cells can be transfected with caveolin-expressing nucleic acids (e.g. a caveolin expression cassette) and thereby be induced to express caveolin.

In one embodiment, the free cholesterol of the LDL is labeled with a detectable label, and the uptake of free cholesterol is detected by detecting (quantifying) the amount of detectable label incorporated into the cell either as a function of time, or at a fixed time after exposing the cell to the label and the test compound. An example of one such assay is provided in Example 1(J) where the uptake of $^3$H-FC is measured in the presence of NEM or $KNO_3$ (see, e.g FIG. 8).

Alternatively, the agonistic or antagonistic activity of a compound can be determined screened simply by measuring changes in the rate of production, or the absolute concentration, of free cholesterol transport vesicles in cells exposed to the compound as compared to control cells similarly treated but without the test compound. test cells in the presence and absence of the compound that is to be tested. Methods of isolating free cholesterol transport vesicles are provided below in Section VI. Once the vesicle is isolated the lipid can be quantified according to any of a number of methods well known to those of skill in the art (see, e.g., Example 1).

One of skill will readily appreciate that assays of the type describe herein are subject to numerous variations. Thus, for example, in a competitive format, the same assays can be used to identify compounds that block agents known to up- or down-regulate the LDL-FC pathway of this invention. In such competitive formats, the cells are contacted with two agents; one agent known to up- or down-regulate the LDL-FC pathway and a second agent whose activity is to be screened. The ability of the second agent to mitigate the agonistic or antagonistic activity of the known agent is then measured as described above.

The ambient LDL and HDL concentrations can be altered to up-regulate or to down-regulate the LDL-FC pathway to provide a characteristic level of LDL-FC pathway against which to compare assay the agonistic or antagonistic effect of the agents to be tested. Thus, for example, where it is desired to up-regulate the LDL-FC pathway, the test cells are preferably cultured in media and/or plasma containing high concentrations of LDL (e.g., about 1.0 mg/ml protein), but low concentrations of HDL (e.g., about 0.25 mg/ml protein). Conversely, where it is desired to down-regulate the LDL-FC pathway, the cells are preferably cultured in media and/or plasma containing low concentrations of LDL (e.g., about 0.25 mg/ml protein) and high concentrations of HDL (e.g., about 1.5 mg/ml protein).

B) Screening for Modulators of Free Cholesterol Efflux

In another embodiment, this invention provides methods of screening for inhibitors and inducers of cellular efflux of free cholesterol (e.g., where agents that increase cellular efflux are expected to act as anti-mitotic agents). In general, the assays involve contacting a cell with an agent to be tested for anti-mitotic activity; and detecting the effect of the agent on the efflux of free cholesterol from the cell. An increase in efflux of free cholesterol indicates that the agent is anti-mitotic. Free cholesterol efflux can be determined by any of a number of means. For example, where the cell is spiked with labeled free cholesterol (e.g. [$^3$H]-FC) the free cholesterol efflux can be directly detected by detecting the amount of labeled free cholesterol released in a given time (e.g., with and without the test agent present).

In another embodiment, mitotic activity can be directly measured (e.g, as the cell proliferation rate). Thus changes in cell number per unit time with and without the test agent present can be determined. It will also be noted that a number of surrogate markers for cell proliferation are well known to those of skill in the art. Such surrogate markers include, but are not limited to, the uptake of particular metabolites (e.g. labeled amino acids, etc.).

In a particularly preferred embodiment, free cholesterol efflux is detected by another surrogate marker; expression level of the caveolin gene. It was a discovery of this invention that upregulation of the caveolin gene increases free cholesterol efflux and thereby decreases the mitotic capacity of the cell by reducing the cellular free cholesterol. Detection of changes in expression level of the caveolin gene associated with the presence, absence, or concentration of the test agent thus provide a measure of the mitotic activity of that agent.

There are a wide variety of methods of detecting expression level(s) of the caveolin gene. In one embodiment, the gene products (i.e. mRNA or caveolin protein) can be detected and/or quantified directly. Thus for example, the transcribed caveolin mRNA can be detected or quantified by hybridization assays (e.g,. a Northern blot) with or without an amplification (e.g., PCR) step, while the translated caveolin protein can be detected or quantified in an immunoassay (e.g., ELISA, Western blot, etc.). The caveolin protein can also be isolated (purified) and quantified directly. Purification procedures are well known to those of skill in the art and include, but are not limited to ammonium sulfate precipitation, affinity columns, column chromatography, gel electrophoresis and the like (see generally, Scopes, (1982) *Protein Purification*, Springer—Verlag, N.Y. and Deutscher (1990) *Methods in Enzymology* Vol. 182: Guide to Protein Purification., Academic Press, Inc. N.Y.).

In a particularly preferred embodiment, the caveolin expression can be detected and/or quantified using a reporter gene under the control of the caveolin promoter. Reporter genes are genes that are operably linked to the nucleic acid sequence of interest (i.e. the caveolin promoter) and express an easily assayable product. Detection of the assayable product indicates the level of expression of the reporter gene which, in turn, the level of expression of the caveolin protein. A cell containing such a reporter construct (reporter gene under control of a caveolin promoter) when contacted by an agent that acts as a mitogen by increasing free cholesterol efflux is expected to show increased level of the reporter gene product as compared to the cell when the agent is lacking.

Reporter genes are well known to those of skill in the art. They include, but are not limited to genes expressing bacterial chloramphenicol acetyl transferase (CAT), beta-galactosidase (β-gal), various bacterial luciferase genes encoded by *Vibrio harveyi, Vibrio fischeri,* and *Xenorhabdus luminescens,* the firefly luciferase gene FFlux, and the like.

The reporter gene can be the sole gene under the control of the caveolin promoter or it may be present in addition to the caveolin gene. When the caveolin gene is present, the caveolin protein can be expressed in fusion with the reporter protein or they can be expressed as separate molecules. The caveolin promoter, and caveolin promoter based reporter constructs are described in detail below.

C) Agents for Screening: Combinatorial Libraries (e.g., Small Organic Molecules)

Virtually any agent can be screened according to the methods of this invention. Such agents include, but are not limited to nucleic acids, proteins, sugars, polysaccharides, glycoproteins, lipids, and small organic molecules. The term small organic molecules refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) Int. J. Pept. Prot. Res., 37: 487–493, Houghton et al. (1991) *Nature,* 354: 84 88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3): 309–314), and PCT/US96/10287), carbohydrate libraries (see, e.g., Liang et al. (1996) *Science,* 274: 1520–1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo,, ChemStar, Ltd, Moscow, RU, 3D Pharmaceuticals, Exton, Pa., Martek Biosciences, Columbia, Md., etc.).

D) High Throughput Screening

Any of the assays for compounds modulating cholesterol uptake or efflux described herein are amenable to high throughput screening. Preferred assays thus detect ATPase dependent free cholesterol uptake from LDL or caveolin-mediated free cholesterol efflux.

High throughput assays for the presence, absence, or quantification of particular nucleic acids, lipids, or protein products are well known to those of skill in the art. Binding assays and reporter gene assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

III. The Caveolin Promoter and Reporter Constructs

In another embodiment this invention provides for caveolin promoter(s) and constructs comprising the caveolin promoter(s) and cells comprising such constructs.

A) Caveolin Promoter(s).

The human caveolin promoter is illustrated in FIG. 14. This figure shows the 5' flanking region, exon 1 and part of intron 1 of the human caveolin gene sequence. The promoter structure of the caveolin gene is illustrated.

Where the translational start site is designated as +1 bp, transcriptional start sites are located at −62 and −106 bp (upstream) of the ATG translational start site. There is a CAAT sequence at −84 bp. A G+C —rich box whose base sequence is identical with that of the consensus for SPI (CCGCCC) was identified at −148 bp. Three sites showing 50–60% homology with the 10-base SRE (ATACCCCAC) of the LDL receptor protein were present at −646, −395 and −287 bp (upstream) of the translational start site.

Deletional mutagenesis of individual SRE-like sequence within the caveolin promoter indicate that the SRE-0like sequences at −646 and −395 bp are both required for the response of the caveolin gene promoter to LDL-derived cholesterol, because deletion of either was associated with an almost complete loss of activity. In contrast, deletion of the third site had essentially no effect.

While the sequence of the native human caveolin promoter is illustrated in FIG. 14, it will be appreciated that this promoter can be routinely manipulated to provide other caveolin promoters that upregulate gene expression in the presence of free cholesterol. Thus, for example, as demonstrated herein, the SRE-like region at −287 bp can be deleted. The remaining SRE-like regions, or all three SRE-like regions can be substituted with other known SRE-like regions or the SRE binding domain itself. Similarly the SpI and/or CAAT regions can be excised or modified. Similarly, the spacing between the various domains can be altered (e.g., narrowed or increased).

The effect of such alterations on promoter activity can be routinely determined. This is accomplished simply by placing a reporter gene under the control of the modified promoter and assaying the expression of the reporter gene product under the conditions of interest (e.g. in the presence of a putative mitotic agent, or the in the presence or absence of LDL, etc.). The expression of the modified promoter can be compared to the expression of the native promoter which will act as a control. Screening of modified promoters is illustrated in Example 3.

B) Caveolin Promoter Constructs

The caveolin gene promoters (native or modified) of this invention can be used as a component in a promoter construct. Preferred promoter constructs are expression cassettes having one or more gene(s) (e.g., a reporter gene and/or a caveolin gene) operably linked to (under the control) of the caveolin promoter.

An expression cassette is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the expression cassettes portion of the expression vector includes a nucleic acid to be transcribed, and, in this case, a caveolin promoter. In some embodiments, the expression cassette also includes an origin of replication, and/or chromosome integration elements, and/or a termination sequence, and/or a polyadenylation sequence.

The expression cassette can comprise a vector. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). It is recognized that vectors often include an expression cassette placing the nucleic acid of interest under the control of a promoter (i.e., the caveolin promoter). Vectors include, but are not limited to replicons (e.g., plasmids, bacteriophages) to which fragments of DNA may be attached and become replicated. Vectors thus include, but are not limited to RNA, autonomous self-replicating circular DNA (plasmids), and includes both the expression and nonexpression plasmids. Where a recombinant microorganism or cell culture is described as hosting an "expression vector" this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

In one embodiment, the caveolin promoter construct can be an expression cassette comprising the caveolin promoter, but lacking the gene or genes that will be expressed. In a preferred embodiment, this expression cassette may contain one or more restriction sites to facilitate insertion of a gene or cDNA that will be operably linked to the promoter.

In a particularly preferred embodiment, the caveolin promoter constructs of this invention include a reporter gene operably linked to the caveolin promoter. One such promoter construct can be produced by cloning the caveolin promoter into the pGL3 luciferase expression vector as described in Example 3.

C) Reporter Cells

In another embodiment, this invention provide reporter cells that increase expression of a reporter gene when the caveolin promoter is upregulated. Reporter cells can be produced by transfecting a eukaryotic, preferably a mammalian cell, with a reporter-gene containing caveolin promoter construct. Method of transfecting cells are well known to those of skill in the art and include, but are not limited to calcium phosphate treatment, electroporation, lipofection, biolistics or viral-based transfection. Other methods used to transform mammalian cells include the use of polybrene, protoplast fusion, liposomes, electroporation, and microinjection.

Virtually any cell can act as a reporter cell using the caveolin promoter/reporter gene constructs of this invention. Preferred cell are mammalian cells and include, but are not limited to fibroblasts, vascular smooth muscle cells, vascular endothelial cells, macrophages, hematopoietic cells, liver cells, kidney cells, and intestinal mucosal cells.

IV. Assays for LDL-FC Pathway Activity

Alteration of cellular cholesterol levels is indicative of a number of pathologies (e.g. diabetes, thyroid hormone deficiency, renal failure and inherited hyperlipidemias, etc.). In such cases it is desirable to ascertain whether abnormal cholesterol content is a consequence of the cholesterol processing by the tissue exhibiting the abnormality or simply a response to abnormal plasma lipid content (e.g., abnormal HDL:LDL ratio). Thus, in one embodiment, this invention provides a method of detecting lipid processing by a cell.

The method involves placing the cell in media containing known physiological concentrations of HDL and LDL and then quantifying the selective uptake of free cholesterol by the cell from the LDL. Comparison of the cholesterol uptake by the test cell with a normal healthy cell of the same type under the same circumstances provides an indication as to the presence or absence of abnormal lipid metabolism by the test cell. Where the test cell deviates significantly from the healthy control, it can be inferred that the test cell shows a defect in lipid metabolism.

Quantification of the cholesterol uptake by the cell from the LDL is accomplished in the same manner as described above in Section II and in Example 1. Suitable cell types include, but are not limited to, virtually any nucleated mammalian cell with human cells being more preferred, and fibroblasts, human vascular smooth muscle cells, human vascular (e.g., aortic) endothelial cells, macrophages, hemapoietic cells, liver, kidney, and human intestinal mucosal cells being most preferred.

V. Isolating FC Transport Vesicles

As indicated above, the LDL-FC transport mechanism of this invention ultimately internalizes free cholesterol into a cholesterol transport vesicle. Moreover, detection of such cholesterol transport vesicles provides a convenient means of detecting or quantifying LDL-FC transport activity and screening for compounds that up- or down-regulate the LDL-FC transport mechanism of this invention.

Previously isolated cholesterol transport vesicles provide useful positive controls for such assays. For example, addition of isolated cholesterol transport vesicles to a density gradient provides a useful marker to establishing the equilibrium point for a cholesterol transport vesicle in a particular density gradient (a method analogous to the use of peptides of known size to calibrate an electrophoretic gel). Similarly the use of known quantities of isolated transport vesicles provides an effective means for producing standard curves to calibrate a quantitative assay. Other such uses of isolated cholesterol transport vesicles will be known and readily appreciated by one of skill in the art.

Thus, in one embodiment, this invention provides for an isolated cholesterol transport vesicle (CTV). The transport vesicle is one that is endogenously produced by a mammalian, more preferably a human, cell (e.g., a human fibroblast). Moreover, since the vesicle is an intracellular repository for free cholesterol internalized by the LDL-FC pathway of this invention, the vesicle is enriched for free cholesterol such that it has a density ranging from about 1.05 g/ml to about 1.12 g/ml, more preferably from about 1.06 g/ml to about 1.10 g/ml and most preferably from about 1.07 to about 1.09 g/ml.

Although not required, the isolation of free cholesterol transport vesicles is facilitated by the preparation of cells containing high concentrations of such vesicles. When free cholesterol is internalized from labeled low-density lipoprotein in the absence of high-density lipoprotein, free cholesterol rapidly accumulates in the cells. (Typical internalization rates of about 150 ng/min at 37° C. were found at physiological concentrations (about 250 mg/ml FC). This leads to noticeable enrichment of FC transport vesicles.

The vesicles can be purified from virtually any mammalian cell type with the exception of red blood cells. Particularly preferred cells include, but are not limited to, virtually any nucleated mammalian cell including, but not limited to fibroblasts, human vascular smooth muscle cells, human vascular (e.g., aortic) endothelial cells, macrophages, hemapoietic cells, liver, kidney, and human intestinal mucosal cells.

The vesicles can be purified from cell homogenate made in the absence of detergent and purified by sucrose density gradient centrifugation as described (see, Kaplan & Simoni, *J. Cell. Biol.*, 101: 446–453 (1985) and Lange et al. *J. Biol. Chem.*, 266: 21439–21443 (1991)). In a preferred embodiment a gradient is established between 2% w/v Ficoll in 9% deuterium oxide and 91% "vesicle buffer" (aqueous 140 mM sucrose, 0.5 mM $MgCl_2$, 1 mM EGTA, 2 mM 2-[N-morpholino]ethanesulfonic acid, 70 mM potassium acetate, pH 6.6) and 20% w/v Ficoll in 90% deuterium oxide and 10% vesicle buffer. Each solution contains in addition, a final concentration of 1 mM dithiothreitol. Using such a gradient, cholesterol transport vesicles can be recovered between the densities of about 1.05 g/ml to about 1.12 g/ml, more preferably from about 1.06 g/ml to about 1.10 g/ml and most preferably from about 1.07 to about 1.09 g/ml.

Further purification can optionally be carried out with streptolysin O-covalently linked to activated CNBr-agarose (Pharmacia). This toxin binds directly to FC-rich vesicles and does not react with FC-poor vesicles (Delattre et al., *Cell. Mol. Biol.*, 24: 157–166 (1979)).

One of skill will appreciate that with the density information provided herein and knowledge that the FC-transport vesicles of this invention are enriched for free cholesterol, other isolation methods can be devised with routine experimentation. Such methods include, but are not limited to labeling LDL-FC with a detectable label and then subsequently detecting and isolating vesicles bearing that label, or contacting the cell homogenate fractions with agarose covalently bound to streptolysin O, a composition that specifically binds cholesterol.

In a particularly preferred embodiment, the free cholesterol transport vesicles can be labeled with a detectable label. As indicated above, preferred labels to not significantly alter the density and hence the mobility of the vesicle in a density gradient. Thus, preferred labels are radioactive labels (e.g., $^3H$) as described above.

The detectable label can be incorporated into the cholesterol transport vesicle by any of a number of means well known to those of skill in the art. One approach, for example, can involve chemical conjugation of the label with the cholesterol transport vesicle after isolation of the vesicle.

However, in a preferred embodiment, the label is incorporated into the vesicle by providing the cell with free cholesterol labeled low-density lipoproteins. As the labeled free cholesterol is incorporated into the vesicle, the vesicle itself thereby becomes labeled. Provision of labeled FC LDL and subsequent incorporation of the label into the cholesterol transport vesicles is illustrated in Example 1.

VI. Modulation of Cellular Free Cholesterol

Because of its high capacity, and sensitivity to the physiological LDL concentration range, the LDL-FC transfer pathway of this invention is effective as part of a mechanism to stabilize plasma membrane free cholesterol concentration as low-density lipoprotein concentration and the free cholesterol content of LDLs changes in response to nutritional status. Under pathological conditions, including thyroid hormone deficiency, diabetes, renal failure and some inherited hyperlipidemias LDL free cholesterol content is unusually high (Fielding, *J. Lipid. Res.,* 25: 1624–1628 (1984); Bagdade et al., *Arteriosclerosis,* 10: 232–239 (1990); Dieplinger et al., *J. Clin. Invest.,* 77: 1071–1083 (1986))) while HDL levels are markedly reduced. Changes of this kind in plasma lipoproteins are often associated with an accumulation of both free and esterified cholesterol in the vascular bed.

In addition, uptake of cholesterol by cells of the blood vessel wall is an integral part of heart disease (atherosclerosis). Cholesterol-filled cells ("foam cells") burst and die, attracting scavenger cells, promoting an inflammatory reaction and contributing to the fatty part of the atherosclerotic plaque which may eventually break off or form a focus-promoting thrombosis.

One of skill in the art would appreciate that treatments that reduce net cholesterol uptake by a cell and/or increase free cholesterol efflux, and therefore cellular cholesterol content, would thereby mitigating one aspect of these pathologies. In addition, it was a discovery of this invention that an increase in cellular free cholesterol is a prerequisite for effective (normal) cell division and blockage of such an increase has an anti-mitotic effect.

Thus, in one embodiment, this invention provides for methods of modulating (e.g., increasing or decreasing or eliminating) net cholesterol uptake by a cell. Such methods preferably involve either inhibiting free cholesterol uptake or increasing free cholesterol efflux to down regulate cellular free cholesterol or upregulating free cholesterol uptake and/or decreasing free cholesterol efflux to up-regulate cellular free cholesterol.

A) Inhibitors of FC Uptake by the LDL-FC Pathway

In one embodiment, the methods of cholesterol regulation comprise inhibiting the internalization of free cholesterol from the plasma membrane into the cytoplasm, more particularly into a cholesterol transport vesicle.

These methods simply involve contacting the cell with a composition that inhibits the LDL-FC pathway of this invention. As illustrated in Example 1, inhibition of the LDL-FC pathway (e.g., by treatment with NEM or $KNO_3$) results in an almost complete (>80%) inhibition of the uptake of free cholesterol from LDLs (see, FIG. 8). Example 2 illustrates inhibition of the LDL-FC pathway of this invention by production of a hyperosmotic environment, reduction or elimination of $K^+$ (e.g., by replacement in the media with $Na^+$), by the inhibition of actin polymerization (e.g., through the use of cytochalasin, by the inhibition of ATPase-driven acidification (e.g., though the use of bafilomycin, and by the use of monensin).

NEM and $KNO_3$ are known inhibitors of vesicular ATPases. The pattern of inhibition of the LDL-FC transport mechanism is characteristic of a vacuolar-type (or vesicular type) ATPase with a cysteine residue located within a Wood type A ATP-binding sequence. Clathrin-free uncoated pits contain a single reported ATPase inhibited by NEM/$KNO_3$ (N-ethylmaleimide-sensitive protein, NSF), while clathrin-coated pits contain two structural ATPases sensitive to sensitive to $KNO_3$ and NEM; an $H^+$-ATPase responsible for acidification in compartment of uncoupling of receptor and ligand (CURL) and an ATPase of unknown function (VCP, valosin-containing protein). VCP and NSF contain virtually identical ATP binding regions:

NSF: -$L_{265}$LYGPPGCGKTLLAR-

VCP: -$L_{515}$FYGPPGCGKTLLAK- $C_{272}$ has been identified in NSF as the binding site for NEM which mediates the inhibition of vesicular transport (Whiteheart et al., *J. Cell. Biol.,* 126: 945–954 (1994)). This structure is absent in $H^+$-ATPase, where NEM binds to a different ATP-binding sequence (Feng et al., *J. Biol. Chem.,* 269: 13224–13230 (1994)).

Preferred inhibitors for use in this invention are NEM-like ATPase inhibitors that bind one or more cysteines within the ATP binding site of the target vesicular ATPase or vesicular ATPase-like mediator of the LDL-FC pathway. Preferred inhibitors can be identified by their ability to bind the ATP-binding sequences described above, or homologous ATP-binding sequences.

Other agents that inhibit or increase ATPase dependent selective uptake of free cholesterol from low density lipoprotein can be identified by routine screening as described above. Such agents can then be used, alone or in combination with other agents, to modulate (e.g., upregulate or downregulate) cellular free cholesterol.

B) Inhibition or Upregulation of Caveolin Gene Expression

Alternatively to, or in addition to, modulation of cholesterol influx, cellular free cholesterol content can be modulated by alteration of free cholesterol efflux. In a preferred embodiment, this is accomplished by altering (e.g., increasing or decreasing) the caveolin content of the cell and thereby altering the formation of caveoli. Thus, for example, where it is desired to inhibit cell proliferation, the caveolin gene expression is upregulated thereby increasing cholesterol efflux and reducing the cholesterol pool available to the dividing cell.

It will be appreciated that free cholesterol efflux can be increased by increasing the cellular caveolin content. This can be accomplished either by providing the cell with caveolin protein or by expressing a caveolin encoding nucleic acid within the cell. Where the caveolin is provided as a protein, a caveolin gene expression product is delivered to the target cell using standard methods for protein delivery. Alternatively, where the caveolin is provided as a caveolin encoding nucleic acid (e.g., a gene, a cDNA, an mRNA, etc.) the nucleic acid is introduced into the cell using conventional methods of delivering nucleic acids to cells. These methods typically involve delivery methods of in vivo gene therapy as described below.

1) Delivery of Caveolin Proteins to Target Cells

Caveolin proteins can be delivered directly to target tissues by injection or administered systemically. In a preferred embodiment, the caveolin proteins are combined with a pharmaceutically acceptable carrier (excipient) to form a pharmacological composition. The caveolin will be administered in a therapeutically effective dose. Thus the compositions will be administered in an amount sufficient to cure or at least partially arrest the pathological state and/or its complications. Amounts effective for this use will depend upon the severity of the disease and the general state of the patient's health.

It will be recognized that caveolin proteins, when administered orally, must be protected from digestion. This is typically accomplished either by complexing the polypeptide with a composition to render it resistant to acidic and enzymatic hydrolysis or by packaging the polypeptide in an appropriately resistant carrier such as a liposome as described above. Means of protecting polypeptides for oral delivery are well known in the art (see, e.g., U.S. Pat. No. 5,391,377 describing lipid compositions for oral delivery of therapeutic agents).

2) In vivo Gene Therapy

In a more preferred embodiment, the caveolin expressing nucleic acids (e.g., cDNA(s)) are cloned into gene therapy vectors that are competent to transfect cells (such as human or other mammalian cells) in vitro and/or in vivo.

Several approaches for introducing nucleic acids into cells in vivo, ex vivo and in vitro have been used. These include lipid or liposome based gene delivery (WO 96/18372; WO 93/24640; Mannino and Gould-Fogerite (1988) *Bio Techniques* 6(7): 682–691; Rose U.S. Pat. No. 5,279,833; WO 91/06309; and Felgner et al. (1987) *Proc. Natl. Acad. Sci. USA* 84: 7413–7414) and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4: 43, and Cornetta et al. (1991) *Hum. Gene Ther.* 2: 215).

For a review of gene therapy procedures, see, e.g., Anderson, *Science* (1992) 256: 808–813; Nabel and Felgner (1993) *TIBTECH* 11: 211–217; Mitani and Caskey (1993) *TIBTECH* 11: 162–166; Mulligan (1993) *Science,* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology,* Doerfler and Böhm (eds) Springer-Verlag, Heidelberg Germany; and Yu et al., (1994) *Gene Therapy,* 1:13–26.

Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol* 63:2374–2378; Miller et al., *J. Virol.* 65:2220–2224 (1991); Wong-Staal et al., PCT/US94/05700, and Rosenburg and Fauci (1993) in *Fundamental Immunology,* Third Edition Paul (ed) Raven Press, Ltd., New York and the references therein, and Yu et al., Gene Therapy (1994) supra). The vectors are optionally pseudotyped to extend the host range of the vector to cells which are not infected by the retrovirus corresponding to the vector. The vesicular stomatitis virus envelope glycoprotein (VSV-G) has been used to construct VSV-G-pseudotyped HIV vectors which can infect hematopoietic stem cells (Naldini et al. (1996) *Science* 272:263, and Akkina et al. (1996) *J Virol* 70:2581).

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.,* 4: 2072–2081; Hermonat and Muzyczka (1984) *Proc. Natl. Acad. Sci. USA,* 81: 6466–6470; McLaughlin et al. (1988) and Samulski et al. (1989) *J. Virol.,* 63:03822–3828. Cell lines that can be transformed by rAAV include those described in Lebkowski et al. (1988) *Mol. Cell. Biol.,* 8:3988–3996. Other suitable viral vectors include herpes virus and vaccinia virus.

3) Inhibition of Caveolin Gene Expression

Conversely, where it is desired to decrease the efflux of free cholesterol, caveolin gene expression can be inhibited. Many methods of gene inhibition are known to those of skill in the art.

For example, the caveolin encoding nucleic acids and caveolin polypeptides of the invention can be used directly to inhibit the caveolin endogenous genes or their gene products. For instance, inhibitory nucleic acids may be used to specifically bind to a complementary nucleic acid sequence. By binding to the appropriate target sequence, an RNA-RNA, a DNA-DNA, or RNA-DNA duplex is formed. These nucleic acids are often termed "antisense" because they are usually complementary to the sense or coding strand of the gene, although approaches for use of "sense" nucleic acids have also been developed.

The term "inhibitory nucleic acids" as used herein, refers to both "sense" and "antisense" nucleic acids. Inhibitory nucleic acid methods encompass a number of different approaches to altering expression of specific genes that operate by different mechanisms. In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids (ribozymes). These different types of inhibitory nucleic acid technology are described, for instance, in Helene, C. and Toulme, J. (1990) *Biochim. Biophys. Acta.,* 1049: 99–125. Inhibitory nucleic acid complementary to regions of c-myc mRNA has been shown to inhibit c-myc protein expression in a human promyelocytic leukemia cell line, HL60, which overexpresses the c-myc protoncogene. See Wickstrom E. L., et al., (1988) *PNAS (USA),* 85:1028–1032 and Harel-Bellan, A., et al., (1988) *Exp. Med.,* 168:2309–2318.

The caveolin polypeptides of the invention can also be used to design molecules (peptidic or nonpeptidic) that inhibit the endogenous proteins by, for instance, inhibiting interaction between the protein and a second molecule specifically recognized by the protein. Methods for designing such molecules are well known to those skilled in the art.

For instance, polypeptides can be designed which have sequence identity with the encoded proteins or may comprise modifications (conservative or non-conservative) of the sequences. The modifications can be selected, for example, to alter their in vivo stability. For instance, inclusion of one or more D-amino acids in the peptide typically increases stability, particularly if the D-amino acid residues are substituted at one or both termini of the peptide sequence.

The polypeptides can also be modified by linkage to other molecules. For example, different N- or C-terminal groups may be introduced to alter the molecule's physical and/or chemical properties. Such alterations may be utilized to affect, for example, adhesion, stability, bio-availability, localization or detection of the molecules.

In another embodiment, cells are transfected to express intrabodies that specifically target and inhibit expression of the caveolin gene or bind to and inhibit the caveolin gene product An "intrabody" as used herein is an antibody that is expressed and active inside a cell. Intrabodies are typically not secreted and instead are directed to intracellularly expressed targets. The intrabodies typically bind the targets within the cell and thereby trap the targets in an intracellular compartment (e.g., the ER). Intracellular antibodies, or intrabodies, are well known to those of skill in the art (see, e.g., Marasco et al. (1993) *Proc. Natl. Acad. Sci. USA,* 90: 7889–7893, Chen et al. (1994) *Hum. Gene Therap.,* 5: 595–601, Chen et al. (1994) *Proc. Natl. Acad. Sci. USA,* 91: 5932–5936, Chen et al. (1996) *Hum. Gene Therap.,* 7: 1515–1525, Marasco (1995) *Immunotech.,* 1: 1–19, and Maciejewski et al. (1995) *Nature Med.,* 1: 667–673).

VII. LDL-FC Related Kits

In another embodiment, this invention provides for kits for screening for anti-mitotic or mitotic compounds whose activity is mediated via the LDL-FC transport pathway of this invention. Kits are also provided for the detection and/or measurement of LDL-FC transport pathway activity. Such kits include, but are not limited to, one or more of the following: caveolin promoter constructs including, but not limited to one or more of vectors or expression cassettes comprising a caveolin promoter and/or a reporter gene under the control of a caveolin promoter, cells comprising one or more caveolin promoter constructs, labeled cholesterol (more preferably LDL containing labeled cholesterol), culture media for the cell, target cells for assaying the activity of agonistic or antagonistic agents, cholesterol transport vesicles for use as a positive control, various buffers and reagents for the culture of the cells, the isolation of cholesterol transport vesicles, and the like.

In addition, the kits may include instructional materials containing directions (i.e., protocols) for the practice of the screening methods of this invention (e.g., protocols for identifying anti-mitotic compounds whose activity is mediated by the LDL-FC pathway of this invention). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the present invention.

Example 1
Identification of an LDL-FC Transport Pathway
Preparation of $^3$H-FC Labeled Plasma and Lipoprotein Fractions Blood was taken into ice-cooled tubes from normolipemic volunteers who had fasted overnight. Streptokinase (Sigma Chemical Co, St. Louis, Mo., final concentration 150 U/ml) was included as anticoagulant (Miida et al., *Biochemistry*, 29: 10469–10474 (1990)). Plasma was obtained as supernatant following centrifugation (2000×g, 30 min at 0° C.) and used immediately in the studies described below.

To compare the influx of FC from different lipoproteins, native plasma was labeled with 1,2-$^3$H-cholesterol (40–50 Ci/mmol) (New England Nuclear, Boston, Mass., USA). Approximately 0.5–1.0 mCi of isotope was brought to 10–20 ml in ethanol, and injected slowly with stirring into 20–30 ml of plasma at room temperature. The plasma was then incubated at 37° C. for 1–2 h to equilibrate the FC label between lipoprotein fractions.

Dithiobis(2-nitrobenzoic acid) (2 mM) was included to inhibit the in vitro esterification of labeled cholesterol (Fielding & Fielding, *Proc. Natl. Acad. Sci. (USA)* 78, 3911–3914 (1981)). FC equilibration was confirmed from the cholesterol specific activity of each lipoprotein class following fractionation as described below. In other experiments labeling of LDL was carried out following fractionation of native unlabeled plasma on columns (2.5×10 cm) of heparin-agarose (Pharmacia, Piscataway, N.J., USA) which had been previously equilibrated in phosphate-buffered saline (PBS) (pH 7.4). Approximately 6–10 ml of plasma was added at 0–2° C. The nonabsorbed fraction contained HDL and other plasma proteins (Fielding & Fielding, *J. Biol. Chem.*, 261: 5232–5236 (1986)). VLDL and LDL were eluted together with 3 M NaCl, 0.01 M phosphate (pH 7.4). Individual lipoproteins were isolated from these fractions by ultracentrifugal flotation (Havel et al., *J. Clin. Invest.*, 34: 1345–1353 (1954)). Lipoproteins were dialyzed PBS containing 0.1 mM sodium EDTA (pH 7.4). Immediately before use in individual experiments the medium was brought to 1 mM $Ca^{++}$, 1 mM $MgCl_2$. If necessary, individual lipoprotein fractions were reconcentrated to their original plasma volume with ultrafiltration membranes (Macrosep: Filtron, Northborough, Mass., USA) at 0° C. Recovery (greater than 95% in these experiments) was assessed by comparing the FC content of the original plasma with the sum of the free cholesterol concentration of the individual fractions recovered.

More than 98% of label in the nonabsorbed fraction in 0.15 M NaCl was recovered as HDL between density limits 1.063–1.21 g/ml. More than 95% of label in the fraction (VLDL+LDL) eluted with 3 M NaCl was recovered as LDL (1.019<d<1.063 g/ml). The ratio of protein and FC mass in LDL was 2.9±0.1

In most experiments, LDL was labeled directly with $^3$H-FC by exchange from albumin-agarose covalent complex essentially as previously described (Miida et al., *Biochemistry*, 29: 10469–10474 (1990)). Briefly, recrystallized human serum albumin (Sigma Chemical Co, St. Louis, Mo., USA) was covalently linked to CNBr-activated Sepharose 6B (Pharmacia). 1,2-$^3$H-FC in ethanol (0.1–1.0 mCi, 10–20 ml/ml gel suspension) was added and the mixture incubated with gentle stirring for 60 mm at 37° C. The labeled suspension was centrifuged (500×g, 1 min) and the gel equilibrated (60 min, 37° C.) with unlabeled LDL prepared as described above. Finally the gel was removed by centrifugation, leaving labeled LDL in the supernatant. LDL total and FC mass was determined fluorimetrically with cholesterol oxidase (Heider & Boyett, *J. Lipid Res.* 19: 514–518 (1978)) in the presence or absence of cholesterol esterase. EC mass was obtained by difference. LDL $^3$H-radioactivity was measured by liquid scintillation spectrometry. FC specific activity in these experiments was $3\times10^4$ to $5\times10^5$ cpm $mg^{-1}$.

In other experiments LDL was labeled with $^{125}$I by the iodine monochloride method (McFarlane, *Nature*, 182: 53 (1958). More than 98% of label was TCA precipitated. Lipid-bound label was <5% when LDL was extracted with $CHCl_3$. The specific activity of $^{125}$I-labeled LDL in these experiments was 2–3×$10^5$ cpm $mg^{-1}$ protein, equivalent to 6–9×$10^5$ cpm of protein label $mg^{-1}$ LDL FC.

Cell Culture

Normal skin fibroblasts, two lines of LDL-receptor-deficient fibroblasts (American Type Culture Collection, ATCC GM 0701 and GM 2000) and a receptor internalization-defective line (GM 2408) were cultured in 10% fetal bovine serum in Dulbecco's modified Eagle's medium (DMEM). For individual experiments, cells were cultured in 3.5 cm plastic dishes until nearly confluent. 24 h before use in individual experiments, dishes were transferred into DUEM containing 7–80% of human plasma.

The viability of cells in DMEM containing 7–80% human plasma was compared to cells in PBS or m DMEM-10% fetal bovine serum in terms of the release of label into each medium from cells prelabeled (60 min, 37° C.) with $^{14}$C-adenine (New England Nuclear, 1 mCi $ml^{-1}$ medium) (Shirhatti & Krishna, Anal. Biochem., 147: 410–418 (1985)). In each case, $^{14}$C label released into PBS or human serum was the same as or lower than that into the standard growth medium containing 10% fetal calf serum-DMEM (8–10% over 120 min).

Determination of FC Influx

Cell monolayers were washed with PBS (×4) at 37° C. then incubated for 5–120 min with 1 ml of $^3$H-labeled plasma or the same volume of purified labeled lipoprotein in PBS with Ca$^{++}$ and Mg$^{++}$ (complete PBS) on an orbital shaker (1 cycle/sec). The protein concentration of isolated lipoproteins was usually 0.5–1.0 mg ml$^{-1}$. The inclusion of irrelevant protein (purified goat IgG, 4 mg ml$^{-1}$) was without effect on FC flux in these experiments.

Following incubation, each monolayer was washed with human album solution (recrystallized, 4 mg ml$^{-1}$) in complete PBS, then 4× with complete PBS. For lipid analysis or fractionation, the washed monolayers were digested with 1 ml of 0.2N NaOH ,24 h, room temperature) before extraction with equal volumes of chloroform and methanol. Portions of chloroform phase were taken for chemical analysis. To determine cell-associated $^3$H-FC label only, cell monolayers were dissolved directly in 4 ml of liquid scintillation cocktail (RPI, Mount Prospect, Ill., USA). Recovery of label under these conditions was greater than 99%. Influx was linear for at least 10 min under these conditions. In some experiments sodium heparin, chloroquine, isobutyl methylxanthine (IBMX) or forskolin (all from Sigma) were included in the influx medium. In other experiments the cells were preincubated with proteinase K (final concentration 10 mg ml$^{-1}$) in PBS for 8 to 10 min prior to measurement of influx.

The FC and EC mass of cell monolayers was determined before and after incubation with lipoprotein as described above. Portions of the chloroform phase were analyzed for total and free cholesterol. Except where indicated each data point represents the mean of triplicate dishes. The coefficient of variation was <5% of means in these experiments.

Determination of Cholesterol Efflux

Fibroblast monolayers were equilibrated with $^3$H-FC-labeled native plasma or with isolated $^3$H-labeled LDL, as specified for each experiment. Following incubation, the dishes were washed with albumin-complete PBS and then (×4) with complete PBS. They were then incubated for 3 min with unlabeled plasma or lipoprotein fractions and the rate of appearance of radioactivity in the medium determined. Samples of medium (100 ml) were immediately chilled in ice water and centrifuged (10 min, 2000×g) at 0–2° C. $^3$H-cholesterol radioactivity in the supernatant was either assayed directly, or fractionated by agarose gel electrophoresis. FC efflux was linear as previously reported (Kawano et al., Biochemistry, 32: 5025–5028 (1993)).

For electrophoresis, 20 ml portions of labeled medium were added to strips of 0.75% w/v agarose in 0.025 M barbital buffer (pH 8.6) and separated as previously described (Fielding et al., Biochemistry, 30: 8551–8557 (1991)). 2.5 mm gel fractions were then collected, and radioactivity measured. The location of major lipoprotein classes was determined from strips run simultaneously with whole native plasma equilibrated (60 min, 37° C.) With $^3$HFC.

Contributions of Plasma Lipoproteins to Cellular Cholesterol Influx and Efflux

Rates of FC influx and efflux between medium and fibroblast monolayers preincubated for 24 h with 7–80% native human plasma in DMEM were determined. Cells equilibrated in 80% compared to 7% v/v plasma contained 35–40% more total cholesterol but only 10–15% more FC. In 50% v/v plasma, cholesteryl ester levels were lower than in 80% plasma but FC levels were almost the same. Rates of transfer of FC between the cells and their extracellular medium were determined for each plasma dilution. Efflux was measured as the rate of transfer of $^3$H-FC radioactivity from labeled native plasma to unlabeled cells. Efflux was determined as the rate of transfer of radioactivity from uniformly labeled cells to unlabeled native plasma medium. As shown in Table 1, both influx and efflux increased almost in parallel by 6-fold when medium FC content was increased 11-fold.

TABLE 1

Effects of medium plasma concentration on rates of cholesterol influx and efflux.

|  | 7% v/v[a] | 50% v/v[a] | 80% v/v[a] |
|---|---|---|---|
| Fg FC dish$^{-1}$ | 13.2 ± 0.2 | 14.8 ± 0.2 | 15.0 ± 0.2 |
| Fg EC dish$^{-1}$ | <0.1 | 1.6 ± 0.6 | 3.0 ± 0.7 |
| FC influx[b] | 27.1 ± 4.6 | 107.0 ± 19.9 | 133.0 ± 20.8 |
| FC efflux[b] | 25.1 ± 0.5 | 102.9 ± 12.8 | 156.6 ± 20.3 |

[a]percent native plasma v/v in DMEM.
[b]Cholesterol influx and efflux are expressed as ng FC transferred min$^-$ between the cell monolayer and 1 ml of plasma medium. Cell monolayers in 3.5 cm dishes were preincubated with unlabeled plasma-DMEM (influx) or with $^3$H-cholesterol labeled plasma-DMEM (efflux) for 24 h. The unlabeled cells were then incubated with $^3$H-FC plasma at the same plasma dilution and cell-associated label determined as described above. The $^3$H-cholesterol labeled cells were incubated at the indicated dilution of unlabeled plasma and efflux determined from medium radioactivity as described above. Each value represents the means ± one SD of six determinations. FC: free cholesterol; EC: esterified cholesterol.

Maximal rates of influx and efflux reached as much as 1% of cell FC min-1. These data show that there is a rapid bidirectional transfer of FC between the cell monolayers and medium-lipoproteins, whose rate is strongly dependent on medium FC concentration.

Cellular FC efflux to plasma media is mainly mediated by HDL (Francone et al., J. Lipid Res., 31: 2195–2200 (1990)). The prebeta-migrating fraction of small HDL appears to be particularly active in this pathway (Castro & Fielding, Biochemistry, 27: 25–29(1988); Huang et al., Arterioscler. Thromb., 13: 445–458 (1993)). The contributions of HDL and LDL to FC influx were determined, and compared to that catalyzed by unfractionated native plasma (Table 2). Each lipoprotein was tested at its original plasma concentration. As shown in Table 2, the greatest influx was obtained from LDL (about 85% of the rate with native plasma).

TABLE 2

Contributions of LDL and HDL to influx from native plasma.

|  | Native Plasma | | LDL | | HDL | |
|---|---|---|---|---|---|---|
|  | FC[a] | Influx[b] | FC[a] | Influx[b] | FC[a] | Influx[b] |
| Experiment 1 | 409 | 79.0 | 282 | 58.9 | 102 | 14.6 |
| Experiment 2 | 367 | 63.6 | 231 | 55.9 | 118 | 15.0 |
| Experiment 3 | 432 | 58.0 | 284 | 51.5 | 149 | 11.5 |
| Means | 403 ± 33 | 69 ± 11 | 266 ± 30 | 56 ± 4 | 123 ± 24 | 14 ± 2 |

[a]FC concentration of plasma and plasma fractions was determined enzymatically and is expressed as Fg FC ml$^{-1}$ original plasma volume.
[b]Rate of $^3$H-cholesterol influx is expressed as ng min$^{-1}$ following determination of cell-associated $^3$H-cholesterol radioactivity over 5 min. Influx was linear over this time course.

This value exceeded the proportion of total FC in plasma associated with LDL. While HDL contributed on average 35% of plasma FC, the rate of PC influx when only HDL was present represented only about 15% that determined with native plasma. The sum of influx catalyzed by HDL and LDL was similar to that measured with native plasma. These data indicated that most FC entering the cells from media containing native plasma originated from LDL.

To determine whether cellular factors contributed to the increased influx of LDL FC with increasing LDL concentration, cells were equilibrated with unlabeled 7% v/v plasma in DMEM and then transferred to unlabeled 80% v/v plasma medium. At zero time and at intervals thereafter up to 24 h in the 80% medium, triplicate dishes of cells were washed, and $^3$H-FC labeled LDL (94 mg FC ml$^{-1}$) added for 10 min at 37° C. to determine the rate of influx of FC. The initial rate of influx into 7% plasma-DMEM medium was 39.8±7.0 ng min$^{-1}$. This rate was almost unchanged at the end of 24 h m 80% plasma-DUEM medium (49.4±8.3 ng min$^{-1}$) (difference not significant). This result indicates that the increase in cholesterol influx as a function of medium plasma FC content shown in Table 1 was solely a function of medium LDL concentration over the 7–80% plasma range.

The concentration dependence of influx from $^3$H-FC labeled LDL is shown in FIG. 1. The data illustrate a saturable pathway with a maximum velocity of 80–100 ng$^{-1}$ (3 experiments) and a Km$_{app}$ of 250±20 mg LDL-FC ml$^{-1}$, equivalent to 0.8 mg ml$^{-1}$ LDL protein (Fielding et al., *Proc. Natl. Acad Sci.* (USA) 81: 2512–2516 (1984)).

Figure 2:
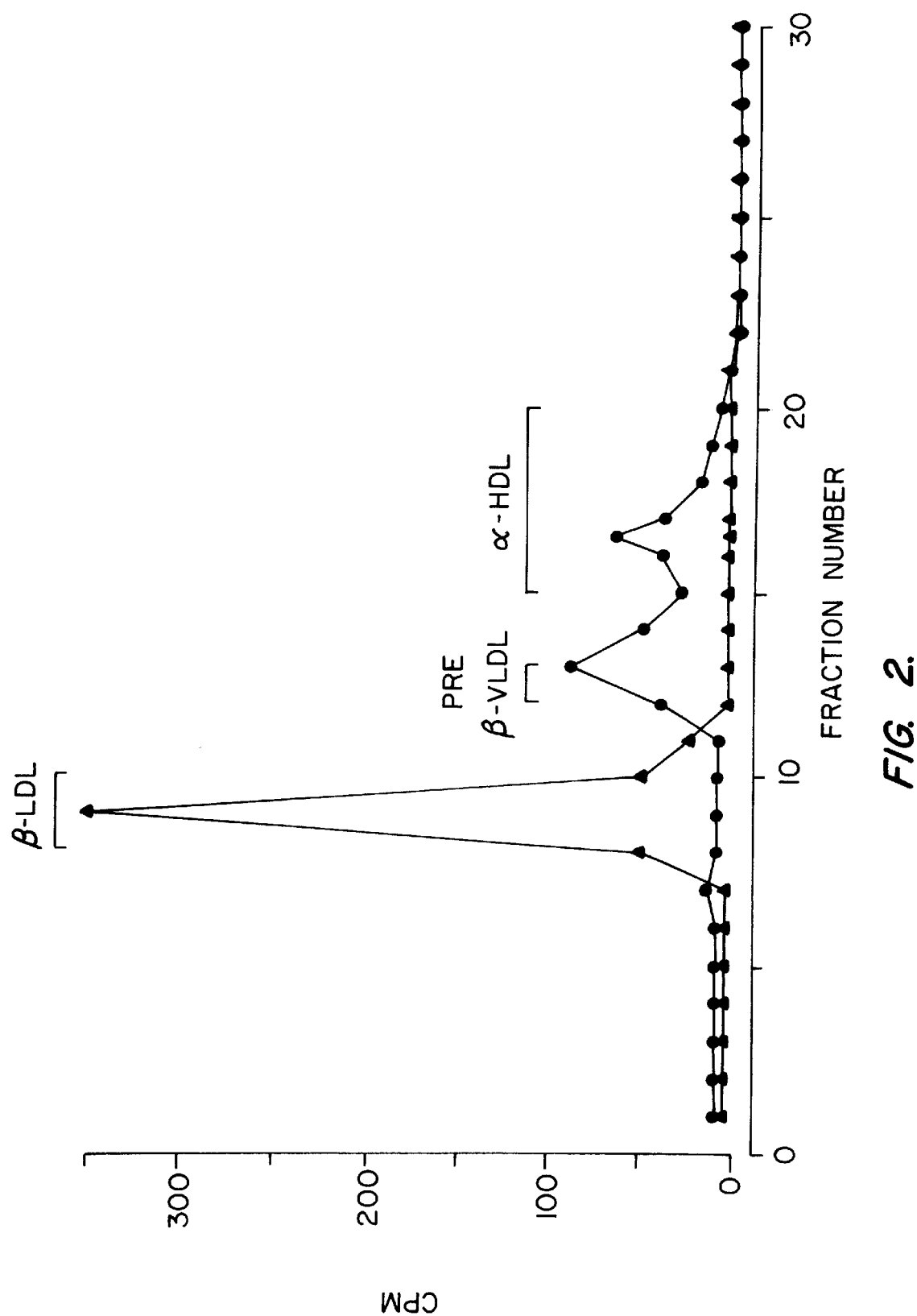
FIG. 2 shows the efflux of radioactivity from cells prelabeled with $^3H$-FC labeled LDL. Unlabeled cells equilibrated in 7% plasma-DMEM were washed, incubated with labeled LDL (10 min, 37° C.) then washed with PBS-albumin and PBS as described in the legend to FIG. 1. Unlabeled native plasma was then added for 1 min at 37° C., then a sample (20 Fl) taken for immediate agarose gel electrophoresis. 2.5 mm wide gel strips were collected after separation and analyzed for contained radioactivity. Closed circles, label recovered from plasma incubated with the cell monolayer. Closed triangles, original $^3H$-FC labeled LDL run in a separate agarose strip. The positions of major lipoprotein species were determined from a sample of whole plasma prelabeled with $^3H$-FC and electrophoresed simultaneously. FC efflux was 17.8 ng min$^{-1}$ in this experiment. Label recovered in total HDL was >90% of that applied.

Cells were incubated (10 min) with $^3$H-FC-labeled LDL. These were then transferred for 3 min to unlabeled native plasma Samples of this plasma were then fractionated by agarose-gel electrophoresis (FIG. 2). Almost the whole of radioactivity was recovered in those fractions which co-migrated with prebeta- and alpha-HDL, consistent with earlier findings (Fielding et al., *Biochemistry*, 30: 8551–8557 (1991); Miida et al. *Biochemistry*, 29: 10469–10474 (1991)). None was detected co-migrating with the LDL or albumin fractions of plasma. These data indicated that transfers of FC occurring at the cell surface were represented for the most part by the uptake of FC from LDL into the cell, and the release of cellular FC to HDL in the medium.

Receptor-Mediated Endocytosis and Free Cholesterol Transfer

The rate of delivery of FC by the endocytosis of intact LDL was determined from the rate of appearance of TCA-soluble $^{125}$I-radioactivity from $^{125}$I-labeled LDL. The rates of influx of $^3$H-FC label from LDL to normal fibroblasts and to several lines of LDL receptor-deficient cells were also compared under the same conditions and assayed as described above.

The appearance of TCA-soluble label from $^{125}$I-LDL was measured over 3 h at 37° C. Its rate was linear and its magnitude (1.2±0.3 ng LDL protein min.$^{-1}$; 3 experiments) represents an LDL FC transfer to the cells of 0.4±0.1 ng LDL free cholesterol min$^{-1}$ from the FC/protein mass ratio of LDL determined experimentally. Under the same conditions the rate of selective transfer of $^3$H-FC label from LDL was 32.4±3.5 ng min$^{-1}$, about 80-fold greater.

The rate of FC transfer from $^3$H-FC labeled LDL to normal, receptor-deficient and internalization-deficient fibroblast monolayers was compared. In a representative experiment at an LDL FC concentration of 46 mg ml$^{-1}$, the rate of transfer to nominal cells was 15±3 ng min$^{-1}$; while the rate of influx from the same preparation to receptor-deficient cells was 16±3, 15±3 and 19±3 ng min$^{-1}$ respectively for GM 2000, GM 0701 and GM 2408 lines.

These data suggest that the influx of LDL FC to cell monolayers maintained in the presence of human plasma was largely independent of the receptor-mediated endocytosis of intact LDL.

Figure 3:
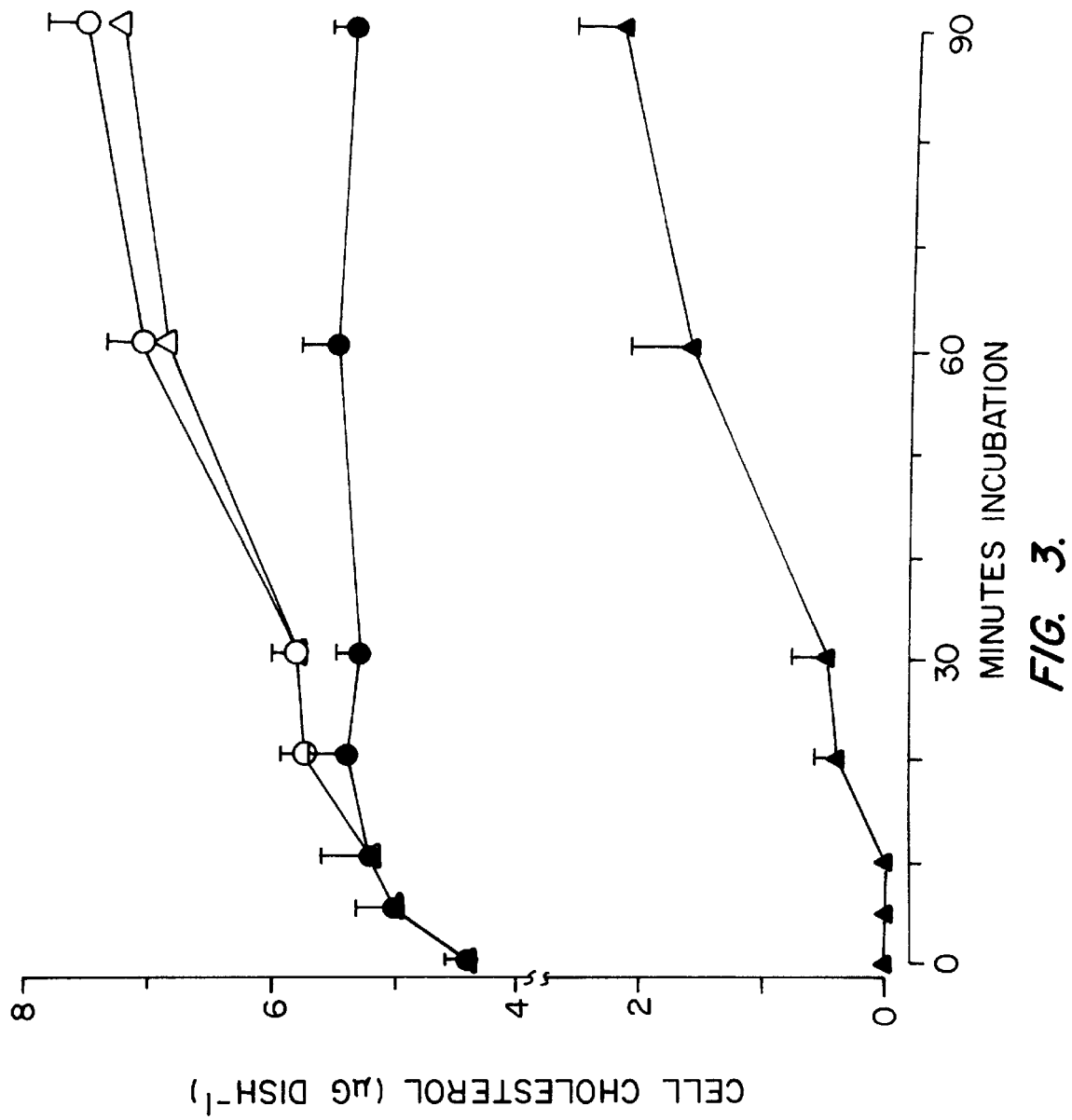
FIG. 3 shows cell free and ester cholesterol mass and cholesterol radioactivity as a function of time in unlabeled cells incubated with $^3H$-FC labeled LDL. Closed circles, cellular FC mass determined enzymatically; open circles, total cholesterol mass; closed triangles, EC mass determined as the difference between total and free values; open triangles, predicted total cholesterol mass based on the sum of the measured initial content of the cells (4.4±0.2 Fg dish$^{-1}$) together with cell-associated $^3H$-cholesterol from labeled LDL based on a measured specific radioactivity of 5.8×10$^4$ cpm Fg$^{-1}$. Data points are the means of six measurements in each case.

Cellular Effects of LDL-mediated FC Influx $^3$H-FC-labeled LDL was incubated with fibroblast monolayers at 37° C. for up to 90 min. At intervals, cells were washed, and assayed for FC and EC mass and radioactivity. Before the addition of LDL, the cells contained no detectable EC (FIG. 3). Transfer to LDL solution was associated with an increase in cellular FC mass without the appearance of EC over the first 10 min of incubation. Beyond this point, as cell-associated cholesterol label continued to increase, FC mass remained almost constant while EC mass began to accumulate.

Cell-associated cholesterol radioactivity and the increase in cell total cholesterol mass were compared. As shown in FIG. 3, when the specific activity of LDL was used to convert the increase in cell-associated label to mass, calculated values for cellular cholesterol mass were similar to those determined directly, indicating that in the absence of other lipoproteins almost the whole of FC taken up from labeled LDL was retained within the cells. Since much of this cholesterol was esterified, this finding shows that at least some of the FC internalized from $^3$H-FC-labeled LDL must be accessible to microsomal acyl CoA:cholesterol acyltransferase (ACAT), the only significant source of EC in these cells (Suckling & Stange, *J. Lipid Res.*, 26: 647–671 (1985)). This was confirmed by determining the specific activities of FC and EC in extracts of cells incubated with LDL for 60 and 90 min. These did not differ significantly, confirming that internalized LDL FC was available for esterification and in equilibrium with cellular EC.

Kinetics of Cellular FC Influx Mediated by LDL

The mechanism of LDL-mediated influx of labeled FC was studied further by measuring the ability of unlabeled lipoprotein fractions to displace cell-associated label, as a function of the time during which the influx of $^3$H-FC took place.

Figure 4:
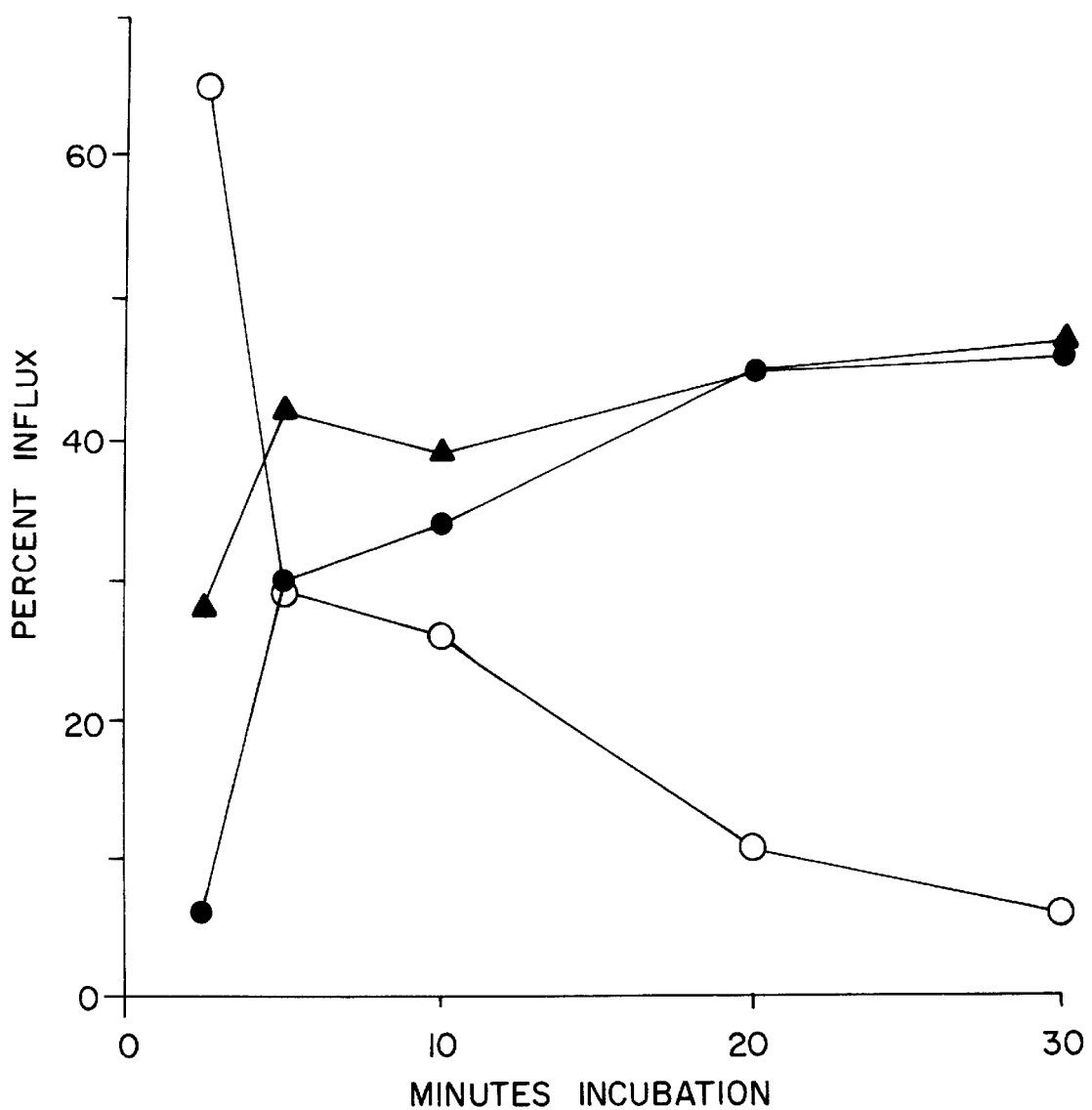
FIG. 4 shows the distribution of cell-associated $^3H$-FC from LDL as a function of time. Label released by unlabeled LDL (open circles); label released by unlabeled HDL but not unlabeled LDL (closed triangles) and label released with neither LDL or HDL (closed circles) expressed as percent of total label released. LDL specific activity was 3.1×10$^4$ Fg ml$^{-1}$. All fractions are defined in terms of label released by either unlabeled lipoprotein within 5 min of incubation at 37° C.

Cell monolayers equilibrated with 7% plasma-DMEM were first incubated with $^3$H-FC labeled LDL as described above. At intervals, dishes of cells were washed, then incubated with unlabeled LDL or HDL at their plasma concentrations. A fraction of cell-associated label was rapidly released; maximum recovery in the medium occurred within 10 min at 37° C. In FIG. 4, the proportions of cell label which were LDL-releasable, LDL-resistant but HDL-releasable, and resistant to both LDL and HDL are shown as a function of time.

The major part of cell-associated LDL $^3$H-FC could initially be dissociated into the medium with cold LDL; but this proportion decreased with time as label accumulated in the cells. The proportion of label resistant to LDL but released by HDL was initially low but reached 40–60% (3 experiments) after 15 min. Label inaccessible to either LDL or HDL over the time course of these experiments was 30–50% of total label after 15 min of incubation at 37° C. These data are consistent with a mechanism in which LDL 3 H-FC was first bound to the cell surface, and then transferred to a compartment from which it was either released by HDL to the medium, or transferred into the cell for further metabolism.

Figure 5:
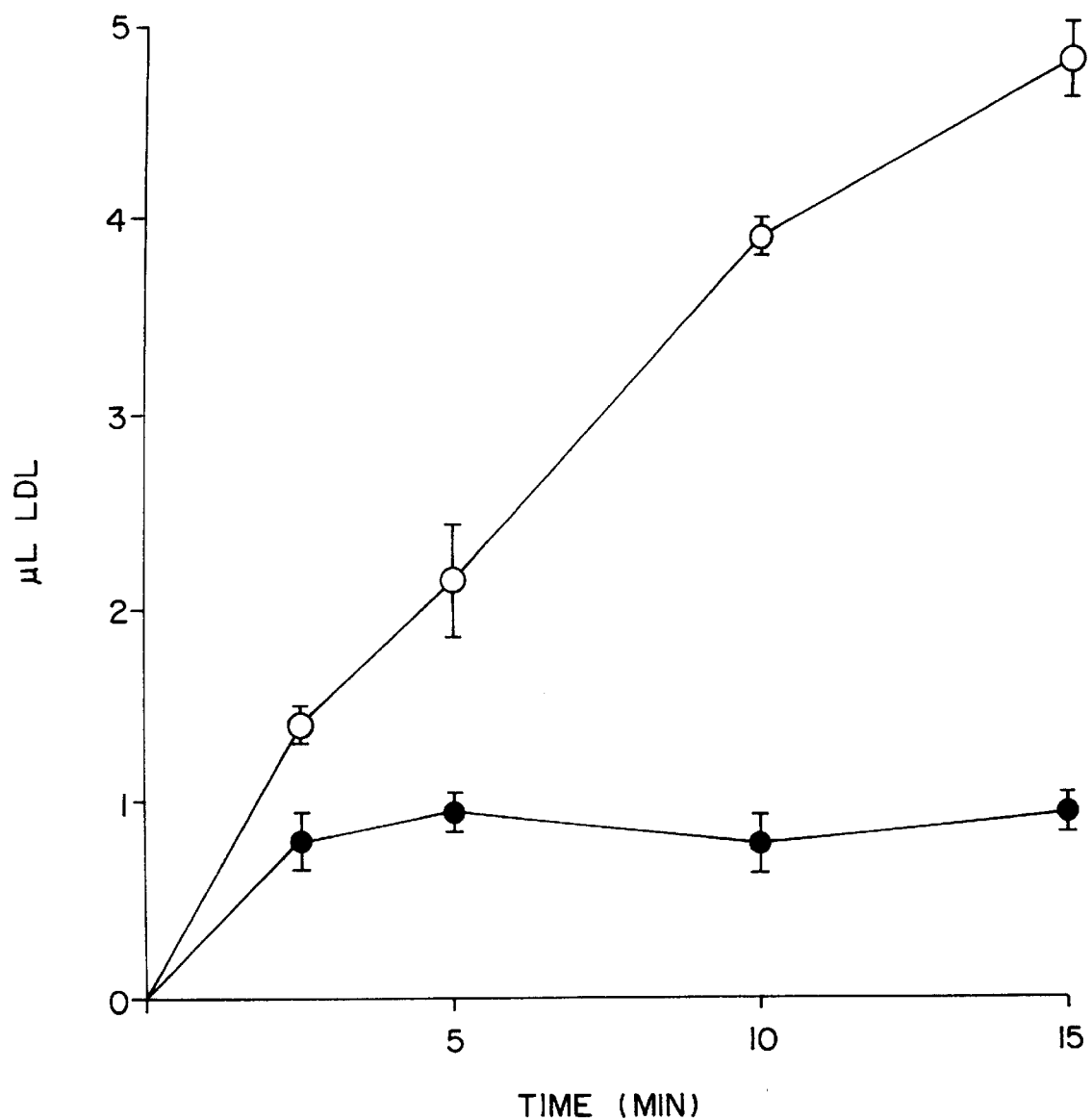
FIG. 5 illustrates the association of LDL $^{125}I$-protein and $^3H$-FC labels with fibroblast monolayers as a function of time. LDL (69 Fg FC ml$^{-1}$) was labeled with either isotope as described in Example 1 and incubated with unlabeled cell monolayers for the period shown. After washing with PBS-albumin and PBS, cell-associated label was determined following solubilization of the cell monolayers with 0.2 N NaOH. Data are expressed in terms of the volume of LDL solution associated with the cells at each time point to allow direct comparison with the cell association of both labels. Values shown are the means of three different experiments. Open circles, LDL $^3H$-free cholesterol; closed circles, LDL $^{125}I$-protein.

Further information on the mechanism of FC influx was obtained by comparing the cell association of LDL labeled in the protein moiety with $^{125}$I, or in the free cholesterol moiety with $^3$H-FC. Unlabeled cell monolayers were incubated with the same concentration of either $^3$H- or $^{125}$I-labeled LDL for 2.5–15 min at 37° C. At each time point the dishes were washed and bound 125 $^{125}$I-protein or $^3$H-FC radioactivity determined. As shown in FIG. 5, cell-associated $^{125}$I-label reached a maximum with 2.5 min of incubation that was maintained during a 15 min incubation period. In contrast, $^3$H-FC label increased nearly linearly over the same period. To allow comparison of protein and free cholesterol labels, the data have been expressed as the uptake of LDL medium volume min$^{-1}$. In these units the uptake of LDL FC by the cells represented 0.3–0.4 ml LDL solution min$^{-1}$, equivalent to 20.7 ng FC min$^{-1}$. In four experiments with different LDL preparations the final ratio of $^3$H/$^{125}$I label was 5.6±1.5 following 15 min of incubation.

Figure 6:
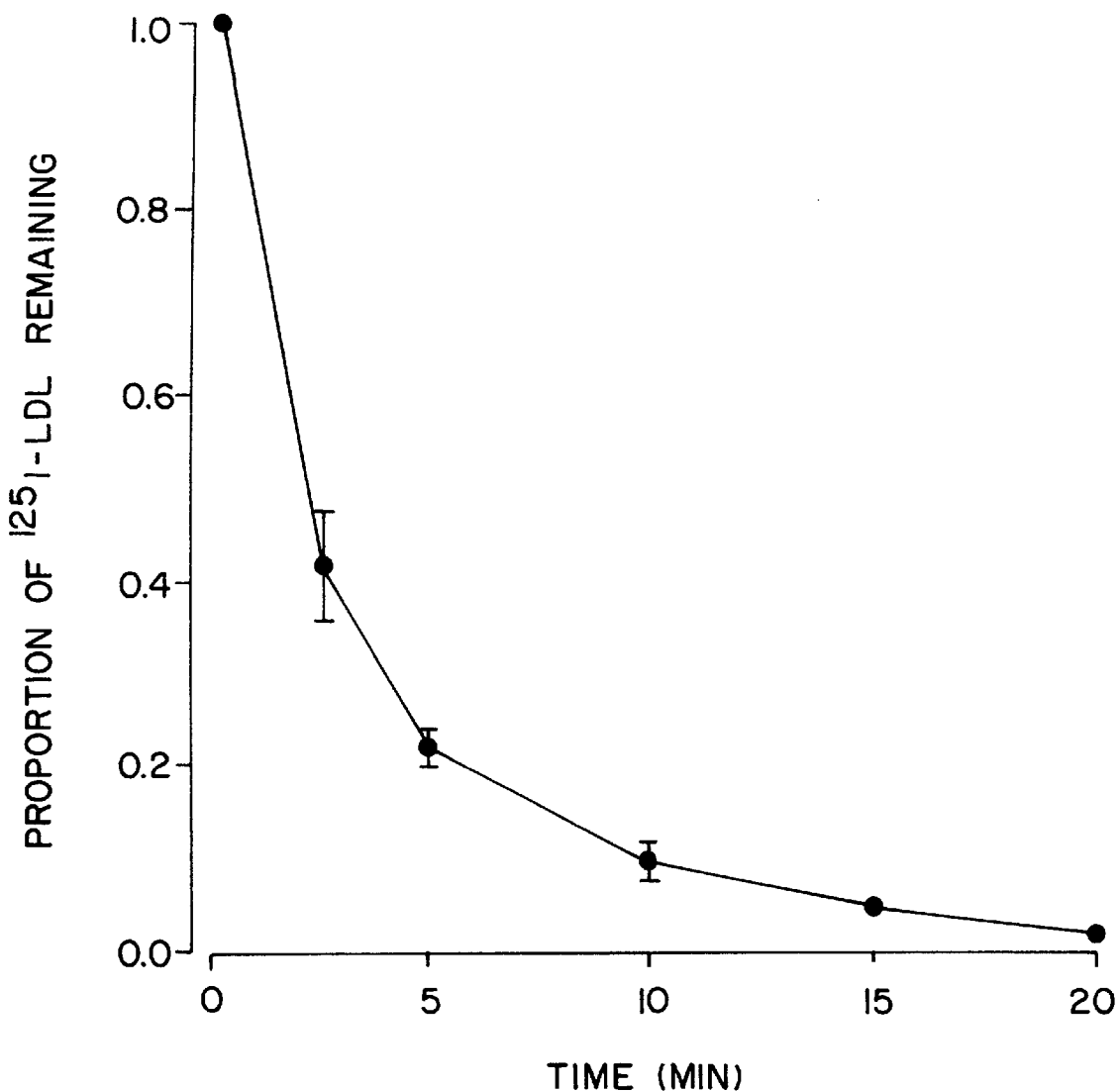
FIG. 6 illustrates the turnover of $^{125}I$-labeled LDL at the cell surface after addition of unlabeled LDL. Labeled LDL (70 Fg FC ml$^{-1}$) was incubated with fibroblast monolayers for 10 min at 37° C. The cells were then washed, and incubated for the time shown with unlabeled LDL at the same concentration. Remaining cell associated label was determined as a function of time with unlabeled LDL following extraction of the cells with 0.2N NaOH. Data from three independent experiments is expressed relative to initial cell content of $^{125}I$-radioactivity.

In other experiments, $^{125}$I-labeled LDL was incubated (10 min) with unlabeled cell monolayers. These were then washed and transferred to medium containing unlabeled LDL at the same concentration. The whole of bound $^{125}$I-label was rapidly displaced (FIG. 6) with a half-time of 1.5—0.5 mm (3 experiments).

The data in FIG. 5 suggest that LDL first bound to the cell, then transferred part of its FC content to the cell surface before being displaced by new particles. The data shown in FIG. 6 indicate that little if any bound LDL was retained at the cell surface.

Inhibition of the Uptake of LDL-derived Free Cholesterol

Figure 7:
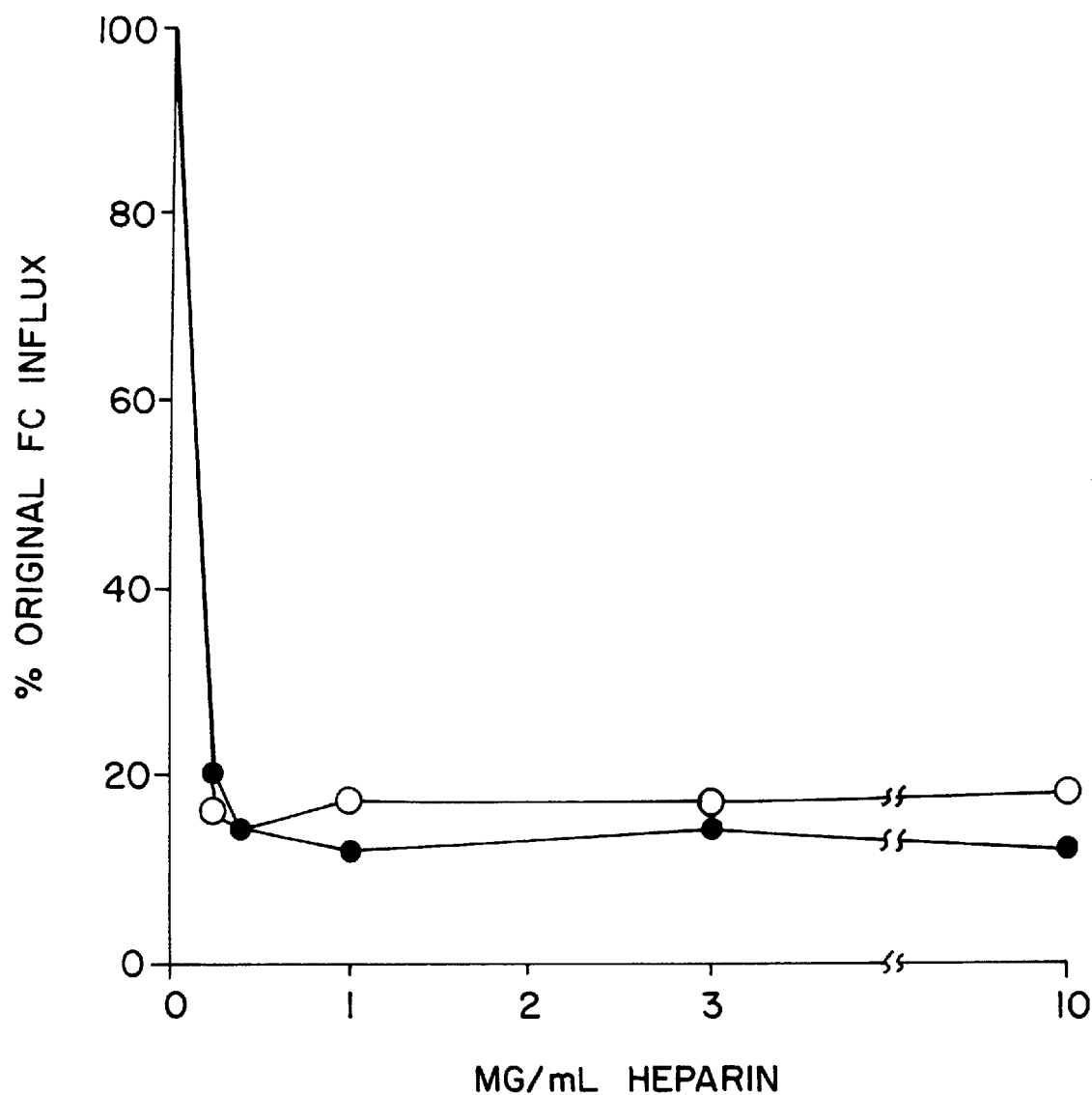
FIG. 7 illustrates the inhibition of LDL $^3H$-FC influx by sodium heparin. Monolayers of either normal fibroblasts (closed circles) or LDL-receptor deficient cells (GM 2000 line, open circles) were incubated with LDL (150 Fg FC ml$^{-1}$) for 10 min at 37° C. in the presence of the indicated concentration of heparin. The plates were then washed as described in the legend to FIG. 1 and extracted to determine cell-associated radioactivity. Data are expressed as a percent of the label bound in the absence of heparin.

As shown in FIG. 7, the influx of FC from LDL was similarly inhibited by heparin in both normal and LDL-receptor deficient (GM 2000) cells. Approximately 80% inhibition was obtained at 0.1 mg/ml heparin. In contrast to LDL receptor-mediated influx (Goldstein & Brown, 1974) or HDL-mediated efflux (Kawano et al., *Biochemistry*, 32: 5025–5028 (1993)) the uptake of $^3$H-FC LDL label was only slightly inhibited (7±6%; 4 experiments) when the cell monolayers was pretreated with proteinase K under the same conditions as previously.

HDL mediated efflux has been reported dependent upon cellular cAMP levels and activity of signaling intermediates, (Oram et al., *Arterioscler. Thromb.*, 11: 403–414 (1991); Hokland et al., *J Biol. Chem.*, 268: 25343–25349 (1993); Voyno-Yasentskaya et al., *Proc. Natl. Acad Sci. (USA)*, 90: 4256–4260 (1993)). The effect of these agents on the internalization and retention of LDL-derived FC was determined. As shown in Table 3, there was no effect on LDL FC uptake by forskolin or isobutyl methylxanthine under conditions shown previously to modify HDL-mediated signaling (Oram et al., *Arterioscler. Thromb.*, 11: 403–414 (1991)). Azide and vanadate, effective inhibitors of ATPases catalyzing transmembrane ion transport (Pederson & Carafoli, *Trends Biochem. Sci.*, 12: 146–150 (1987)) were also without effect on LDL FC transfer. There was no effect of progesterone, even at a concentration (30 mM) which would maximally inhibit fibroblast ACAT activity (Goldstein et al., *Proc. Natl. Acad. Sci. (USA)*, 75: 1877–1881 (1978)) or cholesterol transport in hepatocytes (Lange, *J. Biol. Chem.*, 269: 3411–3414 (1994)). However N-ethylmaleimide (NEM) and KNO$_3$, inhibitors of the ATPases required for vesicular transport between cell compartments (Pederson & Carafoli, *Trends Biochem. Sci.*, 12: 146–150 (1987); Tageya et al., *J. Biol. Chem.*, 268: 2662–2666 (1993)) both strongly (>75%) inhibited the uptake of LDL FC by these cells.

TABLE 3

Effects of metabolic inhibitors on the uptake of $^3$H-cholesterol from LDL.

| | Concentration | FC Influx (Fg)$^a$ | % |
|---|---|---|---|
| PBS only | — | 1.31 ± 0.05 | 100.0 |
| Na-azide | 1 mM | 1.18 ± 0.02 | 89.5 |
| NH$_4$-vanadate | 1 mM | 1.36 ± 0.08 | 103.2 |
| N-ethylmaleimide | 2 mM | 0.40 ± 0.01 | 30.0 |

TABLE 3-continued

Effects of metabolic inhibitors on the uptake of $^3$H-cholesterol from LDL.

| | Concentration | FC Influx (Fg)$^a$ | % |
|---|---|---|---|
| KNO$_3$ | 50 mM | 0.28 ± 0.02 | 21.0 |
| Progesterone | 30 FM | 1.28 ± 0.06 | 97.3 |
| Forskolin | 30 FM | 1.39 ± 0.01 | 105.3 |
| IBMX | 100 FM | 1.46 ± 0.04 | 110.8 |
| Chloroquine | 20 FM | 1.34 ± 0.04 | 102.3 |

Confluent cell monolayers were cultured in unlabeled 7% plasma-DMEM, washed in PBS (×4), pre-equilibrated in PBS (30 min, 37° C.) with the factors shown at the indicated concentration (or with PBS only, in the control dishes) then incubated (60 min, 37° C.) in $^3$H-cholesterol labeled LDL-FC (60.2 Fg ml$^{-1}$). Cells were then washed and extracted as described above. Values shown are means ± one SD for triplicate dishes.
$^a$Influx is calculated from cell-associated $^3$H-label (LDL-FC specific activity 2.24 × 10$^4$ cpm Fg$^{-1}$).

With cells prelabeled to equilibrium (24 h) with $^3$H-FC, inhibition by NEM was complete within 30 min. of the extracellular addition of inhibitor. Maximal inhibition was obtained at 2–5 mM NEM in intact cells, compared to 1 mM in assays of vesicular transport in vitro (Tageya et al.,*J. Biol. Chem.*, 268: 2662–2666 (1993)).

Figure 8:
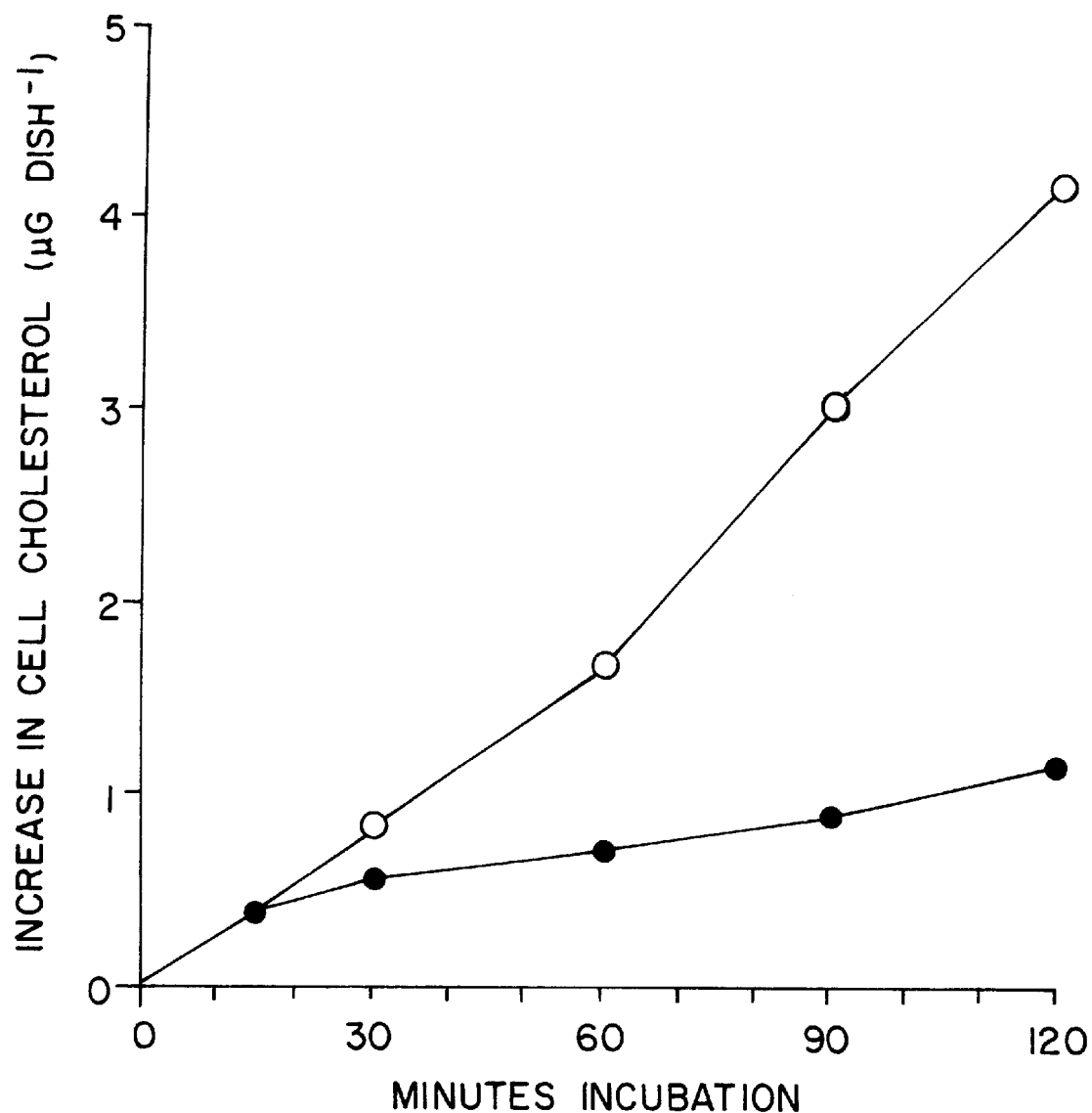
FIG. 8 shows the time course of uptake of $^3$H-FC labeled LDL in the presence or absence of 5 mM NEM. Cells in 7% plasma-DMEM were washed, preincubated (30 min, 37° C.) with PBS or PBS-NEM, then transferred $^3$H-FC LDL solution (91 Fg FC ml$^{-1}$) for the indicated period. Open circles, without NEM; closed circles, with NEM. Data points represent means of triplicate dishes.

The time course of inhibition of $^3$H-FC transfer from labeled LDL to unlabeled fibroblast monolayers preincubated (30 min) with NEM is shown FIG. 8. For the first 10–15 min of incubation with LDL, there was no effect of NEM on the cellular uptake of LDL FC. Upon further incubation an almost complete (>80%) inhibition of the uptake of $^3$H-FC from LDL. This was associated with a parallel inhibition of accumulation of cholesterol mass (Table 4). A comparable time course to that shown in FIG. 8 was obtained for cells preincubated with 50 mM KNO$_3$ (data not shown).

TABLE 4

Effects of N-ethylmaleimide (NEM) on cholesterol transfer between cell monolayers and plasma lipoproteins:

| | Control | +NEM |
|---|---|---|
| D total cholesterol (Fg dish$^{-1}$)$^a$ | 4.1 ± 0.3 | 0.4 ± 0.2 |
| Lipoprotein-resistant label$^b$ | 0.57 ± 0.03 | 0.24 ± 0.03 |
| % efflux to plasma (3 min)$^c$ | 13.3 ± 0.1 | 32.4 ± 0.2 |

Values represent data obtained in cells incubated in the presence or absence of 2 mM NEM.
$^a$Increase in cellular cholesterol mass determined enzymatically over 120 min. at 37° C. Initial cell FC was 5.0 ± 0.2 Fg.
$^b$Proportion of cell cholesterol label retained in the cells following incubation (10 min, 37° C.) with 80% v/v plasma-PBS;
$^c$Percent loss of label from cells prelabeled (10 min, 37° C.) with $^3$H-cholesterol labeled LDL, during incubation (3 min, 37° C.) with unlabeled 80% v/v plasma-PBS.

Further information on the mechanism of NEM-mediated inhibition was obtained by preincubating NEM-blocked or unblocked cells with $^3$H-FC labeled LDL for 10 min, before the inhibition of $^3$H-FC transfer was detectable (FIG. 8). The initial rate of appearance of cellular $^3$H-FC in the medium, and the proportion of label resistant to lipoprotein-mediated efflux, were then compared in NEM-blocked and unblocked control cells. As shown in Table 4, NEM mediated an increased rate of efflux, and reduced the proportion of cellular label transferred to the lipoprotein-resistant compartment.

Example 2
Intracellular Transport of Low Density Lipoprotein-derived Free Cholesterol Begins at Clathrin-coated Pits and Terminates at Cell Surface Caveolae Preparation of $^3$H-FC-labeled LDL Plasma was obtained from the blood of normal donors who had fasted overnight. LDL was isolated from plasma by affinity chromatography on heparin-agarose (Pharmacia-LKB, Piscataway, N.J., USA) as described above. LDL-FC was labeled to a final specific activity of $2-6 \times 10^4$ cpm mg$^{-1}$ by incubation (60 min, 37° C.) with agarose-human serum albumin covalent complex labeled with 1,2-[$^3$H]-FC(45–56 Ci mmol$^{-1}$; NEN, Boston, Mass.) (Miida et al. (1990) Biochem., 29: 10469–10474). Free cholesterol (FC) mass was measured fluorimetrically with cholesterol oxidase (Helder & Boyett (1978) J. Lipid Res. 19: 514–518). Phospholipid mass was measured colorimetrically as inorganic phosphate (Emmelot et al., (1964) Biochim. Biophys. Acta 90: 126–145).

Cell Culture

Normal and LDL receptor-deficient fibroblasts (GM2000 line, American Type Culture Collection, Rockville, Md.) were grown to near confluence in plastic dishes in Dulbecco's modified Eagle's medium (DMEM) containing 10% fetal calf serum. The cells were transferred to media containing human plasma or LDL for individual experiments described below.

Uptake of FC from LDL

To measure the rate of selective internalization of $^3$HFC from LDL cell monolayers were washed with Dulbecco's phosphate-buffered saline pH 7.4 (PBS) (CaCl$_2$, 0.1 gl$^{-1}$; KCl and KH$_2$PO$_4$ both 0.2 gl$^{-1}$; NaCl 8 gl$^{-1}$, Na$_2$HPO$_4$ 1.15 gl$^{-1}$; NaH$_2$PO$_4$.7H$_2$O). and then incubated at the temperature indicated for 1–15 min with $^3$H-FC labeled LDL (50–200 mg ml$^{-1}$ FC). Unbound labeled LDL was removed by washing with PBS, and adsorbed intact $^3$H-LDL was then displaced with excess unlabeled LDL (60 min, 0–2° C.). The dishes were washed with PBS-recrystallized human serum albumin (5 mg ml$^{-1}$) and four times with PBS alone. The cells were solubilized with liquid scintillation cocktail (3a70b, RPI, Mount Prospect, Fla., USA) and radioactivity measured by liquid scintillation spectrometry.

In some experiments, the cells were preincubated (60 min) with metabolic inhibitors affecting different steps of intracellular transport. $^3$H-FC labeled LDL was then added, together with inhibitor. The experiment was then completed as described above.

Cytochalasin D, monensin, brefeldin A, nocozadole, taxol and vinblastine were purchased from CalBiochem, San Diego, Calif. Trifluoperazine and N-ethyl maleimide were purchased from Sigma Chemical Co, St Louis, Mo., USA. Bafilomycin Al was obtained from Wako Chemical, Richmond, Va., USA. These reagents were dissolved as a stock solution in dimethyl sulfoxide (DMSO) prior to dilution (>500-fold) in PBS or DME-0.01M Hepes buffer (pH 7.4). There was no effect of carrier alone on the uptake of $^3$H-FC label by the cells.

Transfer of FC Between Intracellular Compartments

Early endosomal vesicles were labeled with LDL-derived $^3$H-FC by a modification of procedures described by Woodman & Warren (1991) J. Cell Biol., 112:1133–1141. Fibroblast monolayers in 10 cm dishes were washed in ice-cold PBS. The cells were labeled by incubation (2 h, 4° C.) with $^3$H-FC LDL. The monolayers were washed in PBS and brought to 31° C. for 0–15 min. The cells were then quickly chilled on ice, and cold unlabeled LDL was added (15 min, 4° C.) to displace any remaining surface-bound labeled LDL and all subsequent steps were carried out at 0–4° C.

Cells from three 10 cm dishes were used for each gradient. Monolayers were washed with 140 mM sucrose, 0.5 mM MgCl$_2$, 1 mM EGTA, 20 mM 2-[N-morpholino] ethanesulfonic acid (MES), 70 mM potassium acetate, pH 6.6 ('vesicle buffer') (Woodman & Warren, supra.). The cells were scraped from the dishes. Dithiothreitol (1 mm) and protease inhibitors (PMSF, 200 mg ml$^{-1}$; benzamidine 0.5 mM; soybean trypsin inhibitor 10 mg ml$^{-1}$; leupeptin 1 mg ml$^{-1}$) were added. The cells were broken with a Dounce homogenizer (15 strokes) and the homogenate centrifuged at 500×g for 5 min. Ribonuclease A (50 mg ml$^{-1}$) was added. After 30 min a second centrifugation was carried out (7000× g, 30 min). Supernatant (~2 ml) was layered on a 10 ml continuous gradient of 2% Ficoll-9% D$_2$O to 20% Ficoll-90% D$_2$O in vesicle buffer containing 1 mM dithiothreitol. Centrifugation in a Beckman SW41 rotor was carried out at 80,000×g for 16 h. Fractions (~0.6 ml) were collected dropwise and the distribution of FC label determined. Because of slight variation in fraction size between gradients, data were normalized to 20 fractions for comparison between experiments. Solution density was determined gravimetrically using 100 ml portions of each fraction. The density of a given fraction was reproducible ±0.5% between experiments.

The identity of intracellular transport intermediates and the extent of any cross-contamination between fractions was established using specific antibodies to protein markers, labeled ligands of receptor proteins, and assays of enzyme proteins. Antibodies included monoclonal antibody to human clathrin heavy chain (ICN Pharmaceuticals, Costa Mesa, Calif., USA), anti-human caveolin polyclonal antibody (Transduction Laboratories, Lexington, Ky., USA) and anti-mannose-6-phosphate receptor protein. For antibody assays, portions of gradient fractions were mixed with 0.1 ml of recrystallized human serum albumin (2 mg ml$^{-1}$ in PBS) and brought to 1 ml with PBS. Protein was precipitated with trichloroacetic acid (final concentration 10% w/v). Following centrifugation (5000×g, 15 min) the pellets were washed with 70% aqueous ethanol, and dissolved in 20 ml of SDS gel sample buffer. After 12% SDS-polyacrylamide electrophoresis, proteins were transferred to nitrocellulose (0.2 mm pore size, S & S, Keene, N.H., USA). Following incubation with individual primary antibodies, blots were incubated with second antibody (anti-mouse or rabbit IgG, Transduction Laboratories, Lexington, Ky., USA) conjugated with horse radish peroxidase, and then visualized with Super-Signal CL-HRP substrate (Pierce, Rockford, Ill., USA). The distribution of antigen between different gradient fractions was determined with a computerized scanner (ImageQuant, Molecular Devices, Sunnyvale, Calif., USA).

Human transferrin (Sigma Chemical Co., St. Louis, Mo., USA) was $^{121}$I-labeled with chloramine T (Markwell (1982) Anal. Biochem., 125: 427–432). Labeled protein was incubated with the cell monolayers, lysate was prepared, and density gradient fractionation was carried out, as described for labeled LDL, except that unincorporated cell-surface transferrin was removed with desferroxamine (Woodman & Warren, supra.) rather than cold LDL.

Enzyme assays were carried out directly on samples of gradient fractions. Alkaline phosphatase was assayed by spectrophotometry at 420 nm after incubation with p-nitrophenyl phosphate (CalBiochem-BRL, San Diego, Calif., USA) according to the supplier's protocol. 5'-nucleotidase was assayed as the rate of production of inorganic phosphate from 5'-ANP (Emmelot et al., supra.).

Transfer of Intracellular FC to the Cell Surface

This assay utilized the finding (see Example 1) that only FC in the caveolar fraction of the plasma membrane fraction was modified by cholesterol oxidase in unfixed fibroblast monolayers.

The rate at which intracellular LDL-derived ³H-FC became accessible at the cell surface was measured as follows. Cell monolayers were labeled with ³H-FC LDL under the conditions shown for each experiment. Unbound and adsorbed LDL were removed as described above. In some experiments metabolic inhibitors of different transport steps were then added for 30 min at 15° C. In each case, at the end of the experiment, the cells were washed with PBS containing recrystallized human serum albumin (5 mg ml⁻¹, pH 7.4) and then PBS. Cholesterol oxidase (Boehringer-Manheim, Indianapolis, Ind., USA) was added in PBS to a final concentration of 1 U ml⁻¹. Incubation was for 4 h at 0° C. The cells were washed with ice-cold PBS, and extracted with 0.1 N NAOH. Cell total lipid was extracted with chloroform-methanol (1:1 v/v). Thin-layer chromatography of portions of CHCl₃ phase was carried out on silica gel layers (Whatman PE Sil G, Fisher Scientific, Pittsburg, Pa., USA) developed in petroleum ether-diethyl ether-acetic acid 80/20/1 v/v. The yield of labeled cholest-4-en-3-one after 4 h at 0° C. did not differ significantly from that obtained after 1 h at 37° C., conditions shown earlier to completely oxidize FC in the caveolar membrane fraction (Smart et al., supra.).

Transfer of ³H-FC from LDL-effects of Inhibitors

Horseradish peroxidase enters human fibroblasts exclusively by fluid phase endocytosis (Steinman et al., (1972) *J. Cell Biol.* 68: 665–687). Transferrin is internalized selectively via the clathrin-coated pits (Pearse & Robinson (1990) *Ann. Rev. Cell Biol.* 6: 151–172), while cholera toxin binds to ganglioside GMI localized to the caveolae (Montesano et al. (1982) *Nature,* 296: 651–653).

Internalization via clathrin-coated pits was selectively reduced by PBS made hyperosmotic by inclusion of 350 mM in place of 150 mM NaCl (Larkin et al., (1983) Cell 33: 273–285; Hansen et al. (1993) *J. Cell Biol.,* 121: 61–72; Cupers et al. (1994) *J. Cell Biol.,* 127: 725–735).

Figure 9:
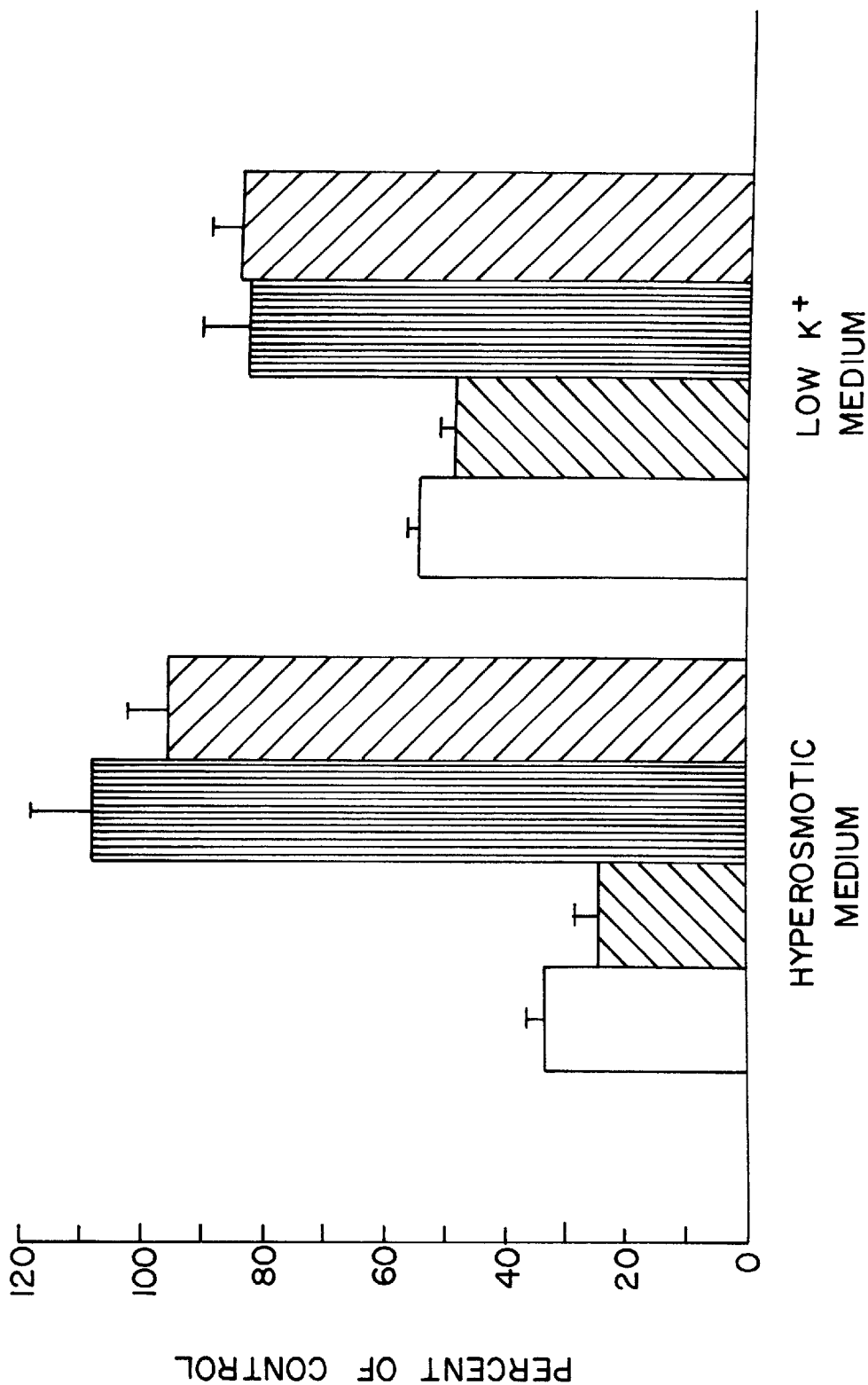
FIG. 9 illustrates uptake of $^3$H-LDL-FC, $125^I$-transferrin, $^{121}$I-cholera toxin or $^{121}$I-peroxidase by fibroblast monolayers incubated in hyperosmotic or K$^+$-free media. Monolayers were preincubated (60 min, 37° C.) with PBS or with hyperosmotic or K$^+$-free medium. Incubation was then carried out with $^3$H-labeled LDL or $^{125}$I-labeled transferrin or cholera toxin in the same media for 30 min. Incubation with $^{121}$I-peroxidase was for 5 min to minimize regurgitation of label. All rates were linear with time over the period of incubation. Cell-associated label in hyperosmotic or K$^+$-free media is expressed relative to the rate of uptake measured in PBS. Left to right for each panel: Open bars, $^3$H-FC LDL; diagonal bars, $^{121}$I-transferrin; vertical bars, $^{121}$I-peroxidase; black bars, $^{125}$I-cholera toxin.

The uptake of ³H-FC from LDL was significantly inhibited under these conditions (FIG. 9). A similar inhibition was observed with ¹²⁵I-labeled transferrin. There was no significant reduction in the uptake of labeled peroxidase or cholera toxin by hyperosmotic medium. Endocytosis via clathrin-coated pits was also reduced in PBS in which K⁺ was replaced isoosmotically by Na⁺ (Cupers et al., supra.). The uptake of transferrin and ³H-FC from LDL was reduced comparably in K⁺-free medium. There was no significant effect on the uptake of peroxidase or cholera toxin under these conditions (FIG. 9). Together the data indicate that the initial transfer of LDL-FC into the cell takes place via the coated pits.

Formation and Subcellular Fractionation of FC-labeled Vesicles

The early stages of intracellular FC transport were studied by density-gradient centrifugation of cell homogenates, under conditions maximizing the formation of clathrin-coated vesicles (Woodman & Warren, supra.). These homogenates were obtained from fibroblast monolayers which had been incubated (2 h, 4° C.) with ³H-FC-LDL, then brought to 31° C. for 0.5 min.

Figure 10:
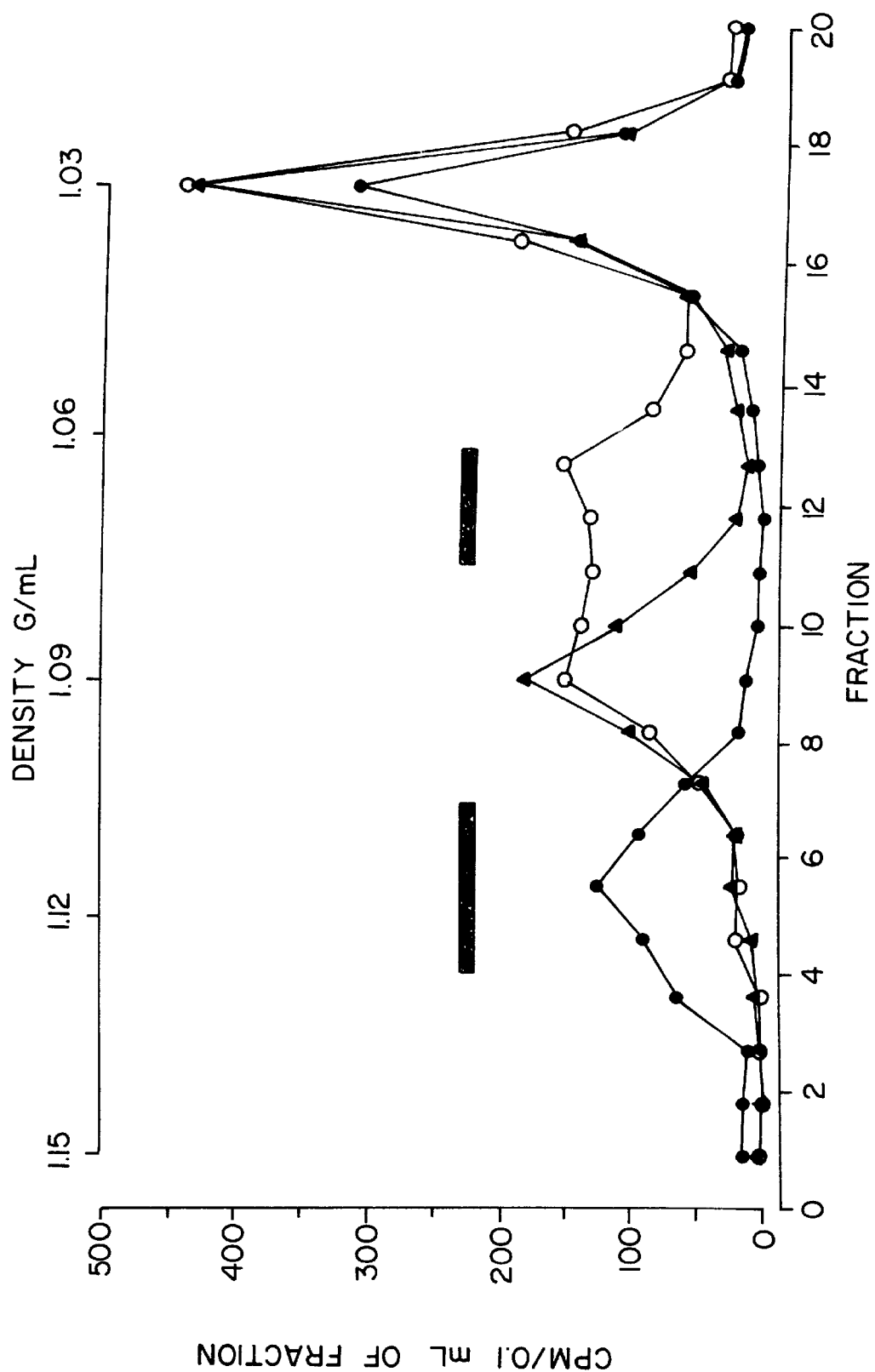
FIG. 10 shows the distribution of $^3$H-FC from LDL following D$_2$O-Ficoll density gradient centrifugation of fibroblast monolayers incubated with labeled LDL. Closed circles, incubation with $^3$H-FC LDL for 2 h at 4° C. then 0. 5 min at 31° C. in the absence of LDL. Open circles, the same, but with 2 min incubation at 31° C. in the absence of LDL. Closed triangles, the same, but with 15 min incubation at 31° C. in the absence of LDL. The distribution of $^{125}$I-transferrin is shown by solid bars. Greater than 95% of label was found within the fractions marked.

A peak of ³H-FC was recovered within the gradient at a density 1.12 g ml⁻¹ (fractions 4–6). The rest of the label was found at the top of the gradient (d 1.03 g ml⁻¹) (FIG. 10). A similar distribution was seen when the cells were incubated with ¹²¹I-transferrin, or when LDL-receptor-deficient (GN12000) cells replaced normal cells in reaction with ³HFC-labeled LDL. After 0.5 min, 74% of transferrin label within the gradient was recovered in the density 1.12 g ml⁻¹ fraction. 96% of clathrin was identified immunologically at d 1.12 g ml⁻¹ with the balance at the top of the gradient. Clathrin was undetectable in other fractions. Alkaline phosphatase, a GPI-anchored protein located in plasma membrane caveolae (Rothberg (1995) *Meth. Enzymol.* 250: 669–679) and 5'-nucleotidase, an additional marker for plasma membrane domains (Emmelot et al., supra.) were detected at the top of the gradient, but not elsewhere, under conditions where a 2% contaminant would have been detected. These data suggest that the initial appearance of ³H-FC label within the cell is in the clathrin-coated vesicles formed from cell-surface coated pits.

Effects of Metabolic Inhibitors on the Uptake of LDL-FC

Several inhibitors reduce internalization of proteins through clathrin-coated pits (Pearse & Robinson, supra.). These agents were used initially at the highest concentrations described in the references cited below. Where inhibition was found, a concentration curve was obtained over at least a 10-fold concentration range. Cytochalasin inhibits endocytosis from coated pits, probably by preventing the polymerization of actin in microfilaments required for effective invagination (Gottlieb et al. (1993) *J. Cell Biol.* 120: 695–710). This agent reduced the uptake of ³H-FC from LDL by an average of 65% at 40 mM (Table 5). No greater inhibition was obtained at 100 mM.

TABLE 5

Transfer of LDL-derived 3H-FC into fibroblast monolayers in the presence and absence of metabolic inhibitors. Influx rates are means (" 1 SD) from three experiments.

| Inhibitor | Concentration | Influx of 3H-FC % Remaining |
|---|---|---|
| None | — | 100 |
| Cytochalasin D | 40 mM | 38" 2 |
| Monensin | 40 mM | 39" 6 |
| Nocodazole | 60 mM | 101" 6 |
| Bafilomycin A1 | 45 mM | 70" 4 |

Monensin inhibits the endocytosis of intact LDL particles through the coated pits (Goldstein et al. (1985) *Ann. Rev. Cell Biol.* 1: 1–39). As shown in Table 5, it was also effective in reducing the selective uptake of FC from LDL. As with cytochalasin D, no increase in inhibition was found at concentrations up to 100 mM. Comparable results were obtained in LDL-receptor deficient (GM2000) cells.

Bafilomycin Al (45 mM), which inhibits ATPase-driven acidification of endocytic vesicles (Furuchi et al. (1993) *J. Biol. Chem.,* 268: 7345–7348) had a smaller maximal effect 30%) in these cells. Inhibitors of Golgi-mediated protein transport (brefeldin A, vinblastine, taxol) (Kristakis et al. (1992) *Nature,* 356: 344–346.) were without effect at concentrations up to 60 mM on the uptake of ³H-FC from LDL, as was nocodazole (up to 60 mM), which inhibits microtubule-dependent transport under these conditions (Thyberg & Moskalewski (1992) *J. Cell Sci.,* 103: 1167–1175).

Intracellular Transport of ³H-FC

Fibroblast monolayers were labeled as before (2 h., 4° C.). Cell-surface and soluble LDL were removed. The dishes were then brought to 31° C. for 2 min in the absence of LDL. Density gradient ultracentrifugation, and determination of label distribution and solvent density, were carried out as described above. Most of the ³H-FC label had now disappeared from the d 1.12 g ml⁻¹ fraction. Label within the gradient was now in a light vesicle fraction (d 1.07 g ml⁻¹) (centered on fraction 12) with significant radioactivity in a fraction of intermediate density (d 1.09 g ml⁻¹) centered on fractions 9–10. Following more extended incubation in the absence of ³HFC LDL (up to 15 min at 31° C.) most of the label within the gradient became concentrated in the fraction of intermediate density. The distribution of FC was compared with that of transferrin, which in fibroblasts enters the cell exclusively via the clathrin coated pits (Woodman & Warren, supra. 1991).

$^{121}$I-transferrin label was also found in the light vesicle fraction (FIG. 10). In contrast to FC, none was found in the intermediate density fraction. Clathrin was not detected in either light or intermediate density fractions.

Under these conditions, the cellular origin of light and intermediate density fractions was investigated with antibodies to protein markers. The density of the light vesicles, the presence of $^{121}$I-transferrin and the absence of clathrin, suggested this fraction contained uncoated vesicles formed by the removal of clathrin by uncoating ATPase (Pearse & Robinson supra., Woodward & Warren supra.). This conclusion was strengthened by an apparent precursor-product relationship between the dense (1.12 g ml$^{-1}$) and light vesicles (d 1.07 g ml$^{-1}$).

In cells incubated with LDL as described above (15 min, 37° C.) the FC/phospholipid molar ratio of the light vesicle fraction was 0.42±0.02, while that of the intermediate density fraction was 0.65±0.03. The dense vesicle fraction (d 1.12 g ml$^{-1}$) had a FC/phospholipid molar ratio of 0.35±0.04, similar to the value of 0.30 reported for adrenal cell coated vesicles (Pearse (1976) *Proc. Natl. Acad. Sci. USA* 73: 1255–1259). The FC/phospholipid ratio for the fraction (d 1.03 g ml$^{-1}$) containing the plasma membrane markers was 0.68±0.03, consistent with published data on this fraction (Cullis & Hope (1991) *In Biochemistry of Lipids, Lipoproteins and Membranes* (Vance, D. E. & Vance, J., Eds) pp 1–41, Elsevier Press, Amsterdam.). Under the same conditions, 75% of caveolin antigen was present in the intermediate density vesicle fraction. The balance was recovered with the plasma membrane markers at the top of the gradient.

The absence of $^{121}$I-transferrin from the intermediate density fraction (d 1.09 g ml$^{-1}$) suggested that transferrin and LDL-derived FC separated from each other in the endosomes, and returned to the cell surface by different pathways. This interpretation was also consistent with the kinetic data, which implied a precursor-product relationship between the light and intermediate-density fractions. Antibodies to different vesicle-bound proteins were used to obtain better identification of the intermediate density fraction.

Mannose 6-phosphate receptor protein is localized mainly to the trans-Golgi network (TGN) (Pfeffer (1991) *Cell Biophys.* 19: 131–140). Caveolin is present in the TGN as well as the plasma membrane (Dupree et al. (1993) *EMBO J.*, 12: 1597–1605) Both proteins are considered to recycle between the TGN and the cell surface. In cells preincubated (15 min) with $^3$H-FC LDL, 75% of caveolin antigen was recovered with the whole of detectable mannose 6-phosphate receptor protein in the intermediate density fraction. These data suggest that FC label in the intermediate density fraction comigrates during density gradient fractionation with vesicles derived from the TGN. The lack of any detectable alkaline phosphatase or 5'-nucleotidase activity in the intermediate density fraction argues against contamination with plasma membrane material.

To determine if exchange or diffusion during fractionation contributed to the changing distribution of FC label shown in FIG. 10, cells were labeled with $^3$H-FC from LDL. Fractionation of the cell homogenate was carried out by density gradient centrifugation as described above. Labeled fractions from the gradient were collected, mixed with homogenate from unlabeled cells, and recentrifuged as before. There was no significant redistribution of label. This finding indicates that the transfer of FC observed within the cell represents not an equilibration, but the orderly transport of this lipid between different cell compartments.

Effects of Metabolic Inhibitors on Intracellular Transport

N-ethylmaleimide (2 mM) blocks selective uptake of FC from LDL. In the presence of 2 mM NEM, no peak of FC label was present with clathrin at d 1.12 g ml$^{-1}$. Almost all was recovered with the plasma membrane fraction at the top of the gradient. A similar result was obtained in the presence of cytochalasin or monensin. The results indicate that these inhibitors of the selective transfer of LDL-FC into the cell inhibit the formation of clathrin-associated vesicles from the plasma membrane.

Return of Intracellular FC to the Cell Surface

Figure 11:
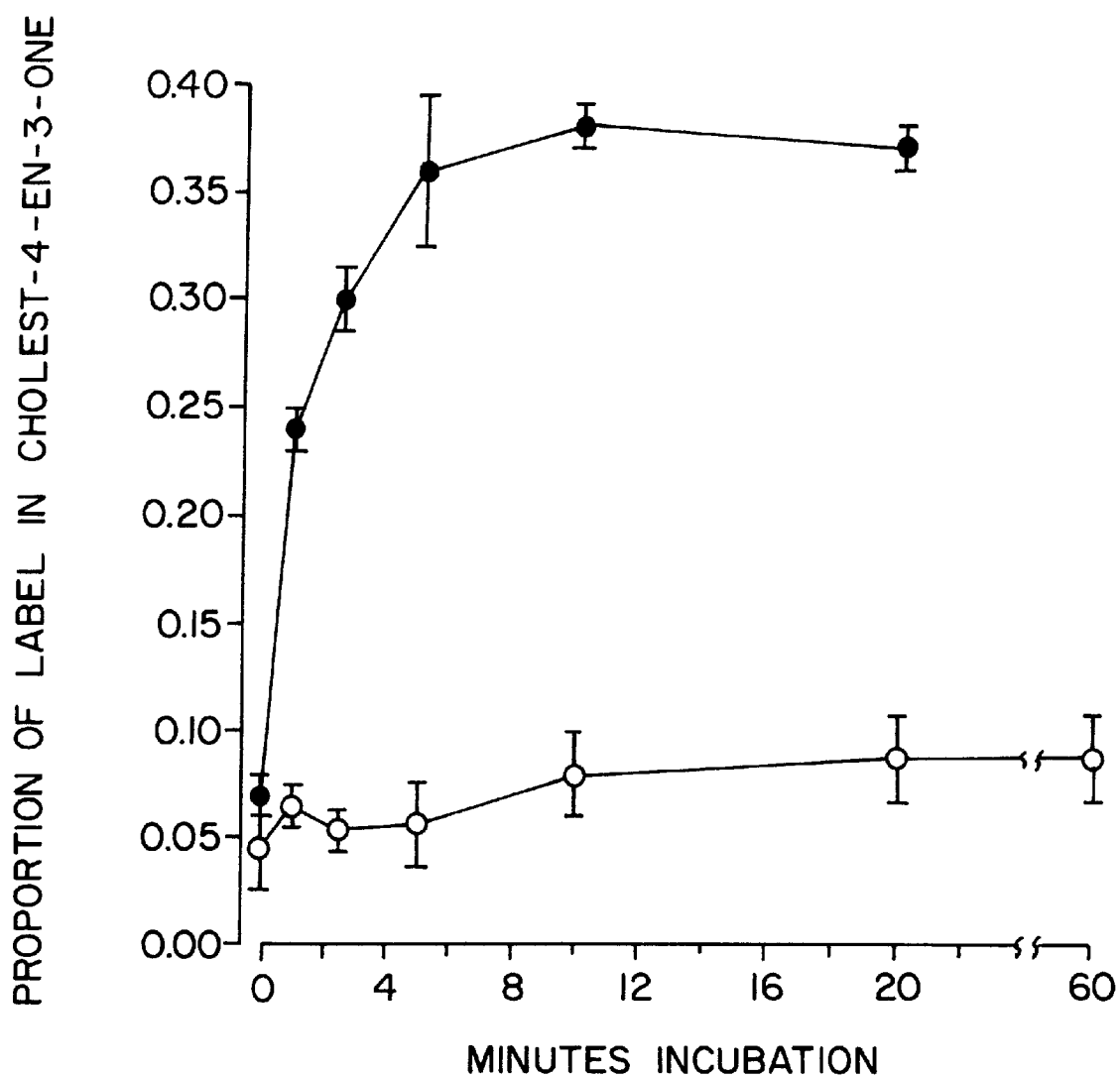
FIG. 11 shows the rate of transfer of $^3$H-FC to the cell surface as a function of temperature. Cell monolayers were prelabeled (2 min, 31° C.) with labeled LDL. Noninteriorized LDL was removed as described in Example 2. The cells were then incubated in the absence of LDL at either 15 or 31° C. for the period indicated. The cells were then cooled on ice, and incubated with cholesterol oxidase (1 U ml$^{-1}$) for 4 h. The oxidized fraction of FC is expressed as a percent of total label. Open circles, 15° C., closed circles, 31° C.

In preliminary studies, fibroblast monolayers were pulse-labeled (2 min, 31° C.) with $^3$H-FC transferred from LDL. The cells were then washed, and surface-bound labeled LDL displaced, as described above. The cells were incubated with cholesterol oxidase at 0–4° C., and the oxidized fraction of FC determined as a fraction of total FC label (Smart et al. supra.). Under these conditions, the cholest-4-en-3-one fraction represented less than 1% of total label (4 experiments, 0.8±0.2%). This result indicates that little or no $^3$H-FC moves through the cell into the caveolae at 4° C. Other cells labeled in the same way were brought to 15° C. for up to 60 min before incubation with cholesterol oxidase at 0–4° C. There was only a slight increase in the amount of cell-surface FC label accessible to cholesterol oxidase (FIG. 11). In contrast, when incubation was carried out at 31° C., there was a rapid increase in oxidized FC ($t_{1/2}$~2 min) reflecting the transfer of FC label from intracellular pools to the cell surface. Following the 2 min pulse label, about 40% of internalized FC became eventually localized to the oxidase-sensitive fraction, a proportion approximately ten-fold higher than that of cellular FC in this fraction in unloaded cells.

Figure 12:
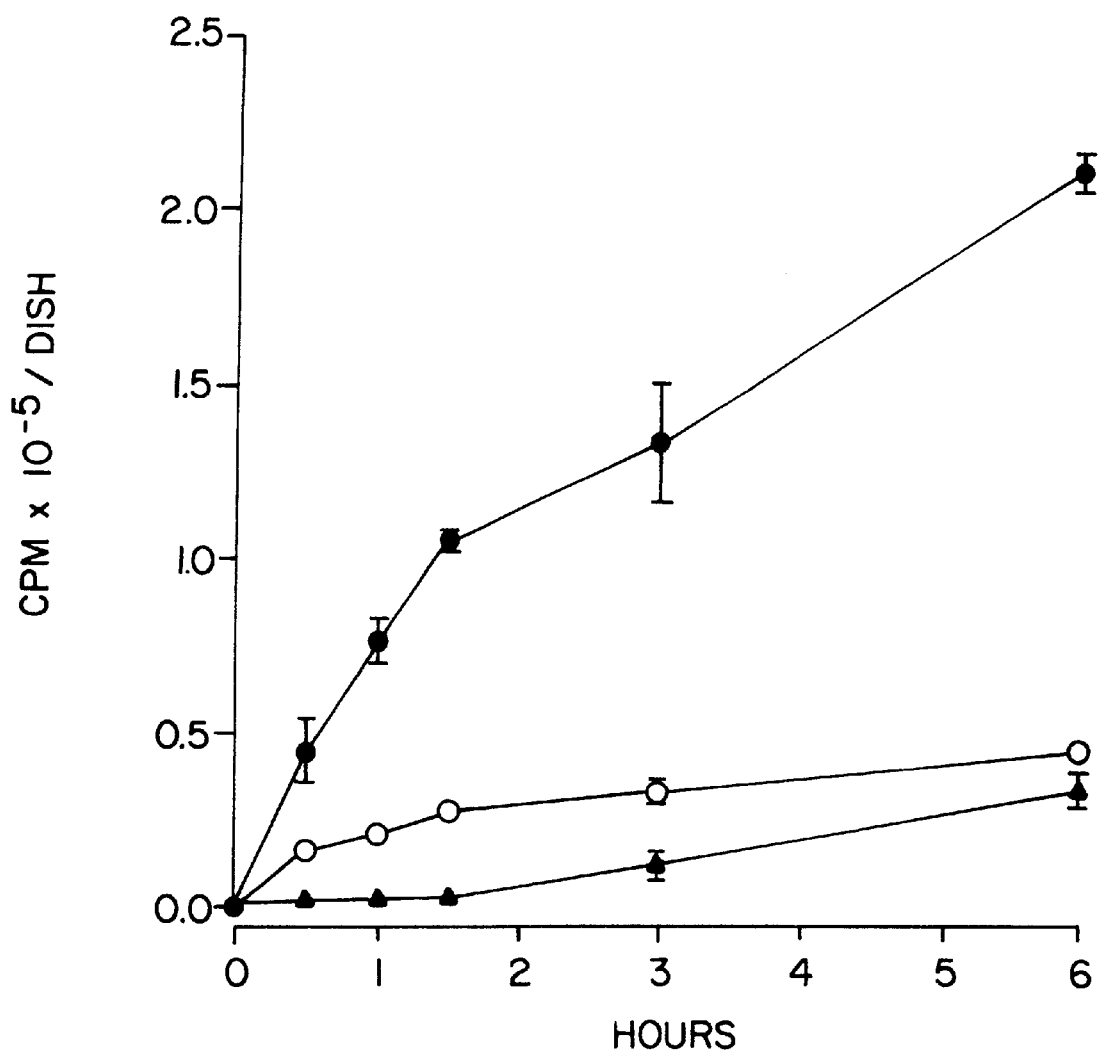
FIG. 12 illustrates evidence of the saturation of the caveolar FC compartment. Cells were incubated at 31° C. with $^3$H-FC-labeled LDL. At the intervals shown, cells were cooled on ice, and intact LDL particles removed as described in Example 2. Cholesterol oxidase (1 U ml$^{-1}$) was added for 4 h at 4° C.C. The level of label in cholesterol ester (CE), free cholesterol (FC) and cholest-5-en-4-one was then determined following thin-layer chromatography as described in Example 2. Open circles, cholest-4-en-3-one; closed circles, FC; closed triangles CE.

In other experiments, cells were continuously labeled with $^3$H-FC LDL at 31° C. in the absence of medium HDL, for a period of up to 60 min. Under these conditions FC accumulates in the cell. At intervals monolayers were cooled on ice, medium and cell-surface LDL removed, and the washed cells incubated at 0–4° C. with cholesterol oxidase. Oxidase-accessible FC was nearly maximal after approximately 60 min at 37° C. Total cell label (mainly unoxidized FC) continued to increase (FIG. 12). FC label accumulated in an intracellular compartment not accessible to cholesterol oxidase. As shown above, the intracellular (oxidase-inaccessible) label under these conditions is recovered as a single major peak in the intermediate density fraction.

Fibroblast monolayers were prelabeled with FC-labeled LDL for 2 min at 31° C. Medium and surface-bound labeled LDL were removed as described above. The cells were incubated with inhibitors of intracellular transport for 30 min at 15° C. Movement of FC label to the cell surface remained negligible (FIG. 11). The cells were brought to 31° C. for 15 min, and then cooled on wet ice. $^3$H-FC transfer to the cell surface (in the presence and absence of inhibitor) was assayed with cholesterol oxidase as described above.

The transport of intracellular 3H-FC to the cell surface was reduced by nocodazole (Table 6). It was unaffected by vinblastine and by brefeldin A, which inhibit transport from the Golgi stacks but has little reported effect on vesicular transport from the TGN (Chege & Pfeffer (1990) *J. Cell Biol.*, 1: 893–899). There was no effect of cytochalasin D or monensin on transport to the caveolae under conditions that inhibited initial uptake of FC from LDL (Table 5). N-ethyl maleimide and $NO_3^-$ inhibitors of vesicle ATPases, which inhibited the initial endocytosis of LDL-FC, also inhibited the return of FC to the cell surface, but less effectively than did nocodazole.

TABLE 6

Effects of metabolic inhibitors on the rate of transfer of intracellular $^3$H-FC to the cell surface.

| Inhibitor | Concentration | % transfer[a] |
|---|---|---|
| N-ethyl maleimide | 2 mM | 50" 3 |
| KNO$_3$ | 50 mM | 70" 4 |
| Nocodazole | 40 mM | 40" 1 |
| Brefeldin A | 40 mM | 95" 5 |
| Vinblastine | 40 mM | 100" 2 |

[a]Relative to rate in the absence of inhibitor. Values are expressed in terms of 3H-FC oxidized to cholest-5-en-4-one by cholesterol oxidase (1 U ml$^{-1}$, 4 h at 0° C.) with cells pulse labeled with labeled LDL (2 min 31° C.) then incubated without LDL for 30 min (31° C.) in the presence of individual inhibitors. Data are from triplicates of individual dishes expressed as a percent of oxidized label recovered in the absence of inhibitor.

Effect of Medium Lipoproteins on the Distribution of Intracellular FC

Figure 13:
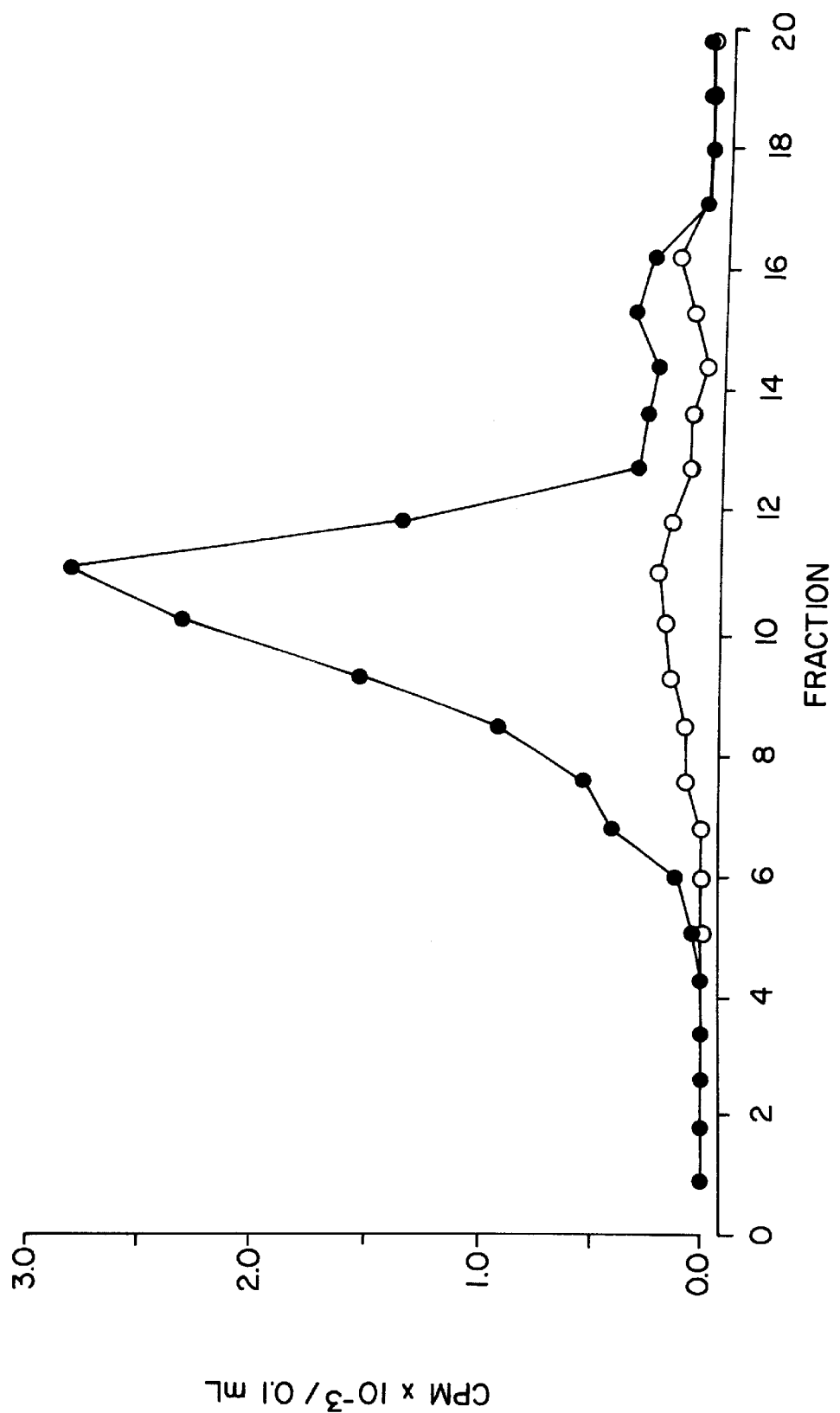
FIG. 13 illustrates the unloading of LDL-derived FC to the extracellular medium in the presence of native plasma. Labeling of the cells was carried out as described in Example 2. The labeled cells were then incubated with plasma or PBS for 5 min at 31° C. The cells were then cooled on ice, homogenized, and fractionated by D$_2$O-Ficoll gradient. Closed circles, distribution after incubation in the presence of PBS; open circles, distribution in the presence of plasma.

Fibroblast monolayers were incubated with $^3$H-FC LDL for 30 min at 31° C. to predominantly label the intermediate density vesicle fraction. Cell surface LDL was removed as described above. The cells were then incubated (5 min, 31° C.) in the presence of human plasma or PBS. In the cells exposed to plasma there was a 12-fold decrease in the intermediate density fraction (FIG. 13). There was a smaller decrease in the plasma membrane fraction. Since relatively little of total cell label was at the cell surface under these conditions (FIG. 12), these data indicate that label in the intermediate density fraction can be quickly unloaded to the extracellular medium. It was shown above that FC was rapidly unloaded from these cells through the caveolae. Consequently, FC in the intermediate density fraction must be transferred to the caveolae prior to unloading.

Intracellular Transport of LDL-derived Free Cholesterol

Cell-surface clathrin-coated pits are the portal by which many receptor-bound proteins enter the cell. The selective uptake of FC from LDL takes place without the internalization of LDL protein. Nevertheless, the results of this study are consistent in indicating that selective FC transfer is also initiated via coated pits. Interalization of FC, like that of transferrin (Pearse & Robinson supra.) was reduced by hyperosmotic and K$^+$-deficient media. Reduced FC uptake was also observed with other inhibitors of receptor-mediated endocytosis, including monensin and cytochalasin. Finally, LDL-derived FC was recovered in the same density gradient fraction as $^{121}$I-transferrin and clathrin; and the appearance of label in these peaks was blocked by inhibitors along with selective FC transfer into the cell. The mechanism by which FC enters coated pits selectively from LDL must be distinct from that involving the high affinity LDL receptor, since the rate of FC transfer is normal in LDL-receptor deficient (GM2000) cells. The FC/phospholipid ratio of isolated coated vesicles in this study was relatively low, compared to that of whole plasma membrane fraction or LDL itself (Fielding & Fielding (1986) *J. Biol. Chem.,* 261: 5233–5236) consistent with earlier data (Pearse supra.). It is possible that FC transfers spontaneously to the outer leaflet of the coated pits, and could help trigger the budding of the endocytic vesicle. The selective uptake of FC may be most relevant in cells where LDL receptors are mainly downregulated.

Vesicles formed from clathrin-coated pits are converted rapidly to a light vesicle fraction through the action of uncoating ATPase (Rothman & Schmit (1986) *Cell,* 46: 5–9). The endosomal contents are retained in the vesicle. The first appearance of $^{121}$I-transferrin and H-FC in a light (d 1.07 g ml$^{-1}$) fraction is consistent with the expected kinetics of this conversion (Woodman & Warren supra.). Shortly thereafter, FC and transferrin separated into different compartments. FC but not transferrin moved to an intermediate density fraction and finally appeared in a plasma membrane fraction enriched in caveolin. Transferrin (but not FC) was returned to a non-caveolar domain of the cell surface. Earlier studies showed that FC selectively internalized from LDL became briefly inaccessible, before reappearing in the plasma membrane caveolae fraction, from which it could be released by HDL. These new data suggest that as part of this transport process, FC transits through a vesicle fraction of intermediate density.

Several pieces of evidence now suggest that the TGN may be a significant component of this fraction. The mannose 6-phosphate receptor protein, identified in the intermediate density fraction, is present mainly in the TGN (Pfeffer supra.). Caveolin, present mainly in the intermediate density fraction in this study as well as in the plasma membranes, has been previously recognized as a protein component of the TGN (Dupree et al. supra.). Caveolin is believed to migrate between the TGN and cell-surface caveolae (Conrad et al. (1995) *J. Cell Biol.* 131, 1421–1433), at least partially in response to cellular FC levels (Smart et al., supra.). Consistent with this relationship, the TGN was identified by electron microscopy in filipin-treated cells as the most FC-rich component of the Golgi stack (Coxey et al. (1993) *J. Lipid Res.,* 34: 1165–1176). In the present study, the FC/phospholipid ratio of the intermediate density vesicle fraction was higher than that of primary endocytic vesicles, and similar to that of the plasma membrane fraction. It was recently suggested that FC may play an important role in regulating the sorting activities of the Golgi apparatus, with the lowest levels of FC (relative to phospholipid) in the cis-Golgi vesicles and the highest in the Irans-Golgi and TGN (Bretscher & Munro (1993) *Science* 261: 1280–1281).

The above data are consistent with a model in which the intermediate density fraction, which colocalizes with material from the TGN on density gradients, represents a component of the intracellular transport of LDL-derived FC, and a reservoir from which excess FC can be transferred to the caveolae for release to plasma lipoproteins, particularly HDL.

Example 3
Two Regulatory Element-like Sequences Mediate Upregulation of Caveolin Gene Transcription in Response to Low Density Lipoprotein Free Cholesterol This example demonstrates that caveolin mRNA levels in confluent human skin fibroblasts are upregulated following increased uptake of low density lipoprotein FC. The increase induced by FC is not associated with detectable change in mRNA stability, indicating that caveolin mRNA levels were mediated at the level of gene transcription. 924 bp of 5'-flanking region of the caveolin gene were cloned and sequenced. The promoter sequence included three GC-rich potential sterol regulatory elements (SREs), a CAAT sequence and a Sp1 consensus sequence. Deletional mutagenesis of individual SRE-like sequences indicated that of these, two (at −646 and −395 bp) were essential for the increased transcription rates mediated by LDL-FC, while the third was inconsequential. Gel shift analysis of protein binding from nuclear extracts to these caveolin promoter DNA sequences, together with DNAase I footprinting, confirmed nucleoprotein binding to the SRE-like elements as part of the transcriptional response to LDL-FC. A supershift obtained with antibody to SRE-binding protein-1 (SPEBP-1) indicated this protein binds at −395 bp. There was no reaction at −395 bp with anti-Sp1 antibody, nor with either antibody at −646 bp. The cysteine protease inhibitor ALLN, which inhibits SREBP catabolism, superinhibited caveolin mRNA levels regardless of LDL-FC. This finding suggests that SREBP inhibits caveolin gene transcription, in contrast to its stimulating effect on other promoters. The findings of this study are consistent with the postulated role for caveolin as a regulator of cellular FC homeostasis in quiescent peripheral cells, and the coordinate regulation by SREBP of FC influx and efflux.

Introduction

In most peripheral cells, the expression of low density lipoprotein (LDL) receptors is strongly downregulated, even by the low levels of LDL present in extracellular fluid. It is demonstrated herein that these cells, which internalize free cholesterol (FC) selectively from LDL at a rate proportional to medium LDL concentration, respond to changes in FC content by modifying the rate of FC efflux. Plasma membrane caveolae represent a major site from which FC exits the cell for transfer to medium plasma lipoproteins, particularly high density lipoprotein (HDL)(Fielding et al. (1995) Biochemistry 34: 14288–14292, Fielding et al. (1996) Biochemistry 35: 14932–14938).

Caveolae are invaginated cell-surface microdomains (60–80 nm diameter) expressed in many quiescent peripheral cells (Fielding et al. (1996) Biochemistry 35: 14932–14938). LDL-FC, internalized through clathrin-coated pits, is transferred in endosomal vesicles to the region of the trans-Golgi network (TGN) (Id.). This FC, together with newly synthesized sterol, is returned to the cell surface caveolae by a temperature-sensitive, nocodazole-dependent pathway, probably as part of the FC-glycolipid "rafts" also carrying GPI-anchored proteins (Parton et al. (1994) Science 269: 1398–1399).

Caveolae contain FC-binding proteins (caveolins) which play a key role in the organization of these organelles at the cell surface. Transformed cells normally contain few if any caveolae, and caveolin is reduced or completely absent (Fra et al. (1994) J. Biol. Chem. 269: 30745–30748, Koleske et al. (1995) Proc. Natl. Acad. Sci. USA 92: 1381–1385). Transfection of lymphoblastoma cells with full-length caveolin cDNA was associated with the expression of morphologically-authentic caveolae (Fra et al. (1995) Proc. Natl. Acad. Sci. USA 92: 8655–8659). The expression of caveolae at the cell surface is regulated by the FC content of the cell (Smart et al. (1994) J. Cell Biol. 127: 1185–1197). These findings suggest that the expression of caveolin may represent a mechanism by which FC efflux can be modulated, in response to changes in cellular cholesterol content. Consistent with this hypothesis, we recently showed that caveolin mRNA levels and FC efflux were upregulated when medium LDL levels, and the uptake of LDL-FC, were increased (Fielding et al. (1997) Proc. Natl. Acad. Sci. USA 94: 3753–3758). Fibroblasts transfected with caveolin antisense DNA also had a reduced rate of FC efflux (Id.). Finally, incubation of fibroblast monolayers with oxysterols or progesterone, which inhibited FC transport between the TGN and cell surface (Fielding et al. (1996) Biochemistry 35: 14932–14938) also reduced equilibrium caveolin mRNA levels (Fielding et al. (1997) Proc. Natl. Acad. Sci. USA 94: 3753–3758). In particular, cholesterol epoxides, major oxysterols of minimally modified LDL (Berliner et al. (1990) J. Clin. Invest. 85: 1260–1266) and human atherosclerotic plaque (11) halved caveolin mRNA levels and FC transport.

Caveolin-1, the largest and first identified product of the caveolin gene family, contains 178 aa and is coded by a 2.2 kb mRNA ((1992) FEBS Lett. 314: 45–48, Scherer (1995) J. Biol. Chem. 270: 16395–16401). Neither the sequence or transcriptional regulation of the 5′-flanking region of the caveolin gene have been described. The present research shows that the caveolin gene promoter contains sterol regulatory element (SRE)-like sequences comparable to those identified for several genes promoting cholesterol influx and cholesterol and fatty acid synthesis (Goldstein et al. (1990) Nature 343: 425–430, Spear et al. (1994) J. Biol. Chem. 269: 25212–25218, Valett et al. (1996) J. Biol. Chem. 271: 12247–12253). These sequences were found to control the response of caveolin to LDL-derived FC.

Materials and Methods

Cell Culture

Normal human skin fibroblasts were cultured to near confluence in 3.5 or 6 cm dishes in Dulbecco's modified Eagle's medium (DMEM) containing 10% bovine fetal serum, before use in individual experiments described below.

Blood was drawn into ice-cooled plastic tubes from normolipemic human volunteers who had fasted overnight. Streptokinase (150 U ml$^{-1}$ final concentration) was included as anticoagulant (Miida et al. (1990) Biochemistry 29: 10469–10474). Plasma was obtained by centrifugation (2000×g, 30 min, 2–4° C.). Plasma total cholesterol was 185–210 mg dl$^{-1}$ and LDL cholesterol was 65–130 mg dl$^{-1}$. Fibroblast monolayers were transferred to 7% or 80% v/v human plasma for 3 h prior to measurement of caveolin mRNA levels (Fielding et al. (1997) Proc. Natl. Acad. Sci. USA 94: 3753–3758). This range approximates to the LDL concentration to which different peripheral cells may be exposed in vivo. In some experiments, native plasma was replaced by plasma from which low density lipoprotein (LDL) had been removed by heparin-agarose affinity chromatography (Fielding et al. (1986) J. Biol. Chem. 261: 5233–5236). In others, incubation with 7% or 80% plasma was carried out in the presence of 25 μM ALLN (Boehringer-Mannheim, Indianapolis, Ind.), a proteosomal cysteine protease inhibitor (Wang X et al. (1994) Cell 77: 53–62). To determine the turnover rate of caveolin mRNA, actinomycin D (CalBiochem, San Diego, Calif.) (2.5 μg ml$^{-1}$) was added to the incubation medium. mRNA levels were then followed as a function of time.

mRNA Preparation and Northern Blotting

Total RNA was extracted from fibroblast monolayers which had been rapidly cooled on ice and washed (×4) with cold phosphate-buffered saline pH 7.4. Total RNA was purified using RNeasy kits (Qiagen, Chatsworth, Calif.). 4 μg of RNA from each sample was applied to 1% agarose-formaldehyde denaturing gels. The fractionated RNA was transferred to 2 μm pore nylon screens by capillary blotting.

A full length caveolin cDNA had been previously isolated from a human lung library (Fielding et al. (1997) Proc. Natl. Acad. Sci. USA 94: 3753–3758). Random-primed $^{32}$P-labeled cDNA was hybridized with the nylon filters at 65° C. Blots were visualized on Kodak X-OMAT AR film. The images obtained were digitized using a computerized densitometer (ImageQuant, Molecular Dynamics, Sunnyvale, Calif.) normalized to total 28S RNA.

Genomic Sequencing of the Caveolin Promoter Region

A human blood leukocyte genomic library (Clontech Laboratories, Palo Alto, Calif.) was screened by plaque hybridization, using as probe a $^{32}$P-labeled 30 bp oligonucleotide antisense to 1–30 bp of the caveolin coding sequence (Glenney (1992) FEBS Lett. 314: 45–48).

Approximately 10⁶ phage were screened on nylon filters (Amersham Life Sciences, Arlington Heights, Ill.). Prehybridization was carried out overnight at 42° C. in 50% formamide, 5×SSC, 20 mM Tris buffer (pH 7.5), 50% dextran sulfate and 0.1% SDS. Hybridization was done under the same conditions. The filters were washed with 2×SSC, 0.1% SDS at room temperature and with 1×SSC, 0.1% SDS at 37° C. and then at 42° C. Four strongly hybridizing clones were digested with BamHl. A 4 kb digestion product was identified by Southern hybridization. This fragment was recovered from agarose gel following electrophoresis, and subcloned into pTZ19. Double stranded sequencing was performed on the subcloned DNA fragment by the dideoxy method using Sequenase 2.0 DNA sequencing kits (Amersham). The 4 kb fragment was found to include approximately 1.0 kb of sequence 5'-to the translational start site, together with the first exon including the 5'-untranslated region, the first intron, the second exon and part of intron 2.

Primer Extension Analysis

Transcription start sites were determined by rapid amplification of cDNA ends (RACE). Total RNA was isolated from human skin fibroblasts to synthesize first strand cDNA. A 30 base oligonucleotide was used corresponding to bp 301–330 of the reported cDNA sequence of caveolin. The reaction was carried out in the presence of Superscript 11RT. Synthesized cDNA was tailed using dCTP in the presence of 1.5 mM $MgCl_2$ and 50 mM KCl in 20 mM Tris-HCl buffer, pH 8.4, and terminal deoxynucleotidyl transferase. The dC-tailed cDNA was amplified by PCR using a nested gene specific primer corresponding to bp 121–150 of caveolin cDNA, and an anchor primer (5'-CUACUACUACUAGGCCACGCGTCGACTAGTACGG-GIIGGGIIGGGIIG-3' SEQ ID NO:3). The amplified DNA product was blunt-ended in the presence of 10 units each of $T_4$ polynucleotide kinase and DNA polymerase I in 10× DNA polymerase buffer (0.5M Tris-HCl pH 7.5, 0.1M $MgCl_2$, 10 mM DTT, 0.5 mg ml⁻¹ bovine serum albumin, 200 μM dNTPs) and 1.0 mM ATP. This DNA was then cloned into the SmaI site of a pTZ vector and sequenced using the vector primer.

Plasmid Construction

The pGL3 luciferase vector (Promega, Madison, Wis.) was used for cloning purposes. A 705 bp Bgl II restriction fragment corresponding to −781 to −76 bp (relative to the translational start site) was isolated from the 4 kb genomic fragment described above. This was subcloned into the Bgl II site of the vector. The orientation of the insert was identified by restriction mapping and DNA sequencing.

Mutations of sequences within the promoter were created by deletional mutagenesis on single strand DNA, using the Sculptor mutagenesis kit (Amersham). On the basis of the caveolin gene promoter sequence, three oligonucleotides were designed: i) from −664 to −620 with bases −646 to −637 deleted; ii) from −412 to −363 with bases −395 to −386 deleted; and iii) from −302 to −262 with bases −287 to −278 deleted. These were used to generate the promoter mutants designated Δ1, Δ2 and Δ3 respectively.

Transient Transfection

Normal skin fibroblasts were plated at a density of 5–8× 10⁵ cells per 6 cm dish. These cells were transfected with 10 μg per dish of the wild type (705 bp) caveolin promoter fragment subcloned in the forward and reverse orientation in the luciferase expression vector pGL3. Transfection was carried out in the same way with pGL3 vector containing the mutant caveolin promoters Δ1, Δ2 and Δ3. Co-transfection with pSV-β-galactosidase (Promega) expressing galactosidase under control of the SV40 early promoter served as an internal control. All transfections were carried out using a calcium phosphate coprecipitation method (Profectin, Promega). The dishes were incubated for 16 h at 37° C. The cells were then re-fed DMEM+10% fetal calf serum. After a further 30 h incubation, the cells were changed to DME medium containing 7% or 80% v/v native human plasma, or plasma-LDL obtained following affinity chromatography (Fielding et al. (1986) *J. Biol. Chem.* 261: 5233–5236). After 3 h the cells were washed with PBS (×2) and then solubilized with lysis buffer (Promega). Cell extracts were centrifuged at 12,000 rpm for 5 min. 20 μl of lysate supernatant was used to measure normalized luciferase activity, using the assay system described by the supplier. After 10–20 sec, luciferase activity was determined using an analytical luminometer (Monolight 2010, Analytical Luminescence Laboratories, San Diego, Calif.).

Electrophoretic Mobility Shift and Supershift Assays

The assay was carried out using a Bandshift kit from Pharmacia. Nuclear extract was prepared from the purified nuclei of confluent human skin fibroblasts equilibrated in 7% v/v plasma medium (22). Three synthetic oligonucleotide probes were synthesized, designated cav-287, cav-395 and cav-646. Their sequence was as follows: cav-287: 5'-CTG CCC AAG CAC CCC AGC GCG GGA CAA C-3' (SEQ ID NO: 4); cav-395: 5'-GCG TCG GCT CCC TCC ACC CCT GCT GAG ATG ATG CAC TG-3' (SEQ ID NO: 5); and cav-646: 5'-CAA AAG TAC ACC ACA GGC ACC CAC ACA GAT TCC TT-3' (SEQ ID NO: 6).

The complementary oligonucleotides were annealed and the probes ³²P-end labeled. 0.5 pmole of end-labeled probe and 4 μg of nuclear extract were used in each reaction in a volume of 20 μl. To compete for nonspecific DNA binding-protein, 1 μg of polydI.dC was included in each reaction. In competition assays, a 200-fold molar excess of unlabeled competitor DNA was added. Homologous double-stranded oligonucleotide was added 5 min prior to addition of radio-labeled probe. Competition was also carried out using mutant double stranded oligonucleotides corresponding to cav-287, cav-395 and cav-646. Reaction mixtures were incubated at room temperature for 30 min. For the supershift assays, nuclear extracts were preincubated with antibody for 1 h on ice before addition of other reaction components. Product DNA-protein complexes were resolved from free DNA on 5% w/v polyacylamide gels in TAE buffer. Gels were dried, and labeled complexes visualized by autoradiography. In some incubations polyclonal antibodies to nucleoproteins reactive with GC-rich promoter sequences (SRE-binding protein-1 (SREBP-1) and Sp proteins 1–4 (Santa Cruz Biotechnology, Santa Cruz, Calif.) were included with the mixture of oligonucleotide and nuclear extract. Formation of a ternary complex was identified by the supershift of labeled complexes following electrophoresis as described above.

DNAase I Footprinting

A probe encompassing bp −646 to −637 was prepared from the coding strand of the 705 bp fragment obtained by Bgl II digestion of the wild type promoter. This fragment was digested with Afl III and the 237 bp Bgl II—Afl III fragment was isolated. DNA containing the −395 to −386 sequence was prepared by digesting the 705 bp promoter fragment with Afl III. The 350 bp fragment produced was digested with BSU 36I. The 225 bp Afl III-BSU 36l DNA fragment obtained was purified as described above.

10⁴ cpm of end-labeled probe was incubated with nuclear extract in a reaction volume of 20 μl also containing 1 μg of poly dI.dC, 10% glycerol, 50 mM NaCl, 2.5 mM $MgCl_2$, 0.5 mM DTT, 0.5 mM EDTA, 0.05% NP-40 in 10 mM Tris-HCl, pH 7.5. After incubation for 30 min at room temperature, 5 μl of a solution containing 5 mM $CaCl_2$, 10 mM $MgCl_2$ was added, and then 0.33 U of freshly diluted DNAase I. 0.074 U of DNAase I was used for probes without nuclear extract. After 1 min the reaction was stopped with 140 μl of 64 μg $ml^{-1}$ of yeast RNA, 192 mM Na-acetate, 32 mM EDTA and 0.14% w/v SDS. DNA was extracted with chloroform/phenol and precipitated in ethanol. DNA was run out on 8% polyacrylamide sequencing gels containing 7M urea. Autoradiography was then carried out as described above.

Results

Transcriptional Regulation of the Caveolin Gene

Actinomycin D inhibits DNA transcription at the level of DNA-dependent RNA polymerase. In the presence of actinomycin (2.5 μg $ml^{-1}$) caveolin mRNA levels in unstimulated cells decayed as a function of time according to log-linear kinetics. In parallel experiments, caveolin mRNA levels were first upregulated with 80% v/v plasma (3 h, 37° C.). Actinomycin was then added, and mRNA levels followed over the same time course. In a third series of experiments, the cells were incubated with both cholesterol α-epoxide (50 μM) and 80% v/v plasma for 3 h at 37° C. before addition of actinomycin. The rate of decrease in caveolin mRNA levels in the presence of actinomycin ($t_{1/2}$ 8.0±1 h, n=4) did not differ in activated and baseline cells. After an 8 h incubation at 37° C., caveolin mRNA, level (relative to total RNA) was 0.52, 0.48 and 0.47 for baseline cells, cells activated with 80% v/v plasma, and cells activated with 80% v/v plasma in the presence of 50 μM cholesterol α-epoxide. These results indicate that the change in equilibrium caveolin mRNA levels following transfer to 80% plasma in the presence or absence of cholesterol α-epoxide was mediated mainly or exclusively at the level of transcription, rather than by changes in mRNA stability. This conclusion is consistent with the 3–5 fold increase in caveolin mRNA levels previously observed after 3 h in cells transferred from 7% v/v to 80% v/v plasma medium (Fielding et al. (1997) Proc. Natl. Acad. Sci. USA 94: 3753–3758).

Structure of the Caveolin Gene Promoter Region

Approximately 1 kb of genomic DNA upstream of the start of exon 1 was sequenced as described under Experimental Methods. Two PCR products 366 and 410 bases in length were detected by RACE and sequenced. The data showed that transcriptional start sites were located 62 and 106 bp upstream of the ATG translational start site. The translational start site was designated as +1 and the two transcriptional start sites as –62 and –106 (FIG. 14a and FIG. 14b). There is a CAAT sequence at –84 bp. A GC-rich box whose base sequence was identical with that of the consensus for SpI (CCGCCC)(Sanger et al. (1977) Proc. Natl. Acad Sci. USA 74: 5463–5468) was identified at –148. Three sites showing 50–60% homology with the 10-base SRE (ATCACCCCAC) of the LDL receptor protein were present –646, –395 and –287 bp upstream of the translational start site.

Deletional Mutagenesis of Caveolin Gene Promoter Sites

Wild type promoter DNA, or mutant promoters Δ1, Δ2 or Δ3 were ligated 5'-to the luciferase gene of the expression vector pGL3. The mutants lacked the SRE-like GC-rich boxes at –646, –395 and –287 bp respectively (FIGS. 14a and 14b). These constructs were used to transfect human fibroblast monolayers as described herein. Three hours following transfer of the cells to 80% v/v plasma medium, luciferase expression was 4–6-fold greater compared to that in cells in baseline (7% v/v) plasma medium. In contrast, galactosidase activity in cells cotransfected with galactosidase expression vector driven by the sv40 early promoter was unchanged (±7%) under the same conditions. Luciferase expression in cells incubated with 80% v/v plasma was reduced by 60% in the presence of 50 μM cholesterol α-epoxide. Expression was reduced ~80% when LDL had been selectively removed from plasma by affinity chromatography.

Figure 15:
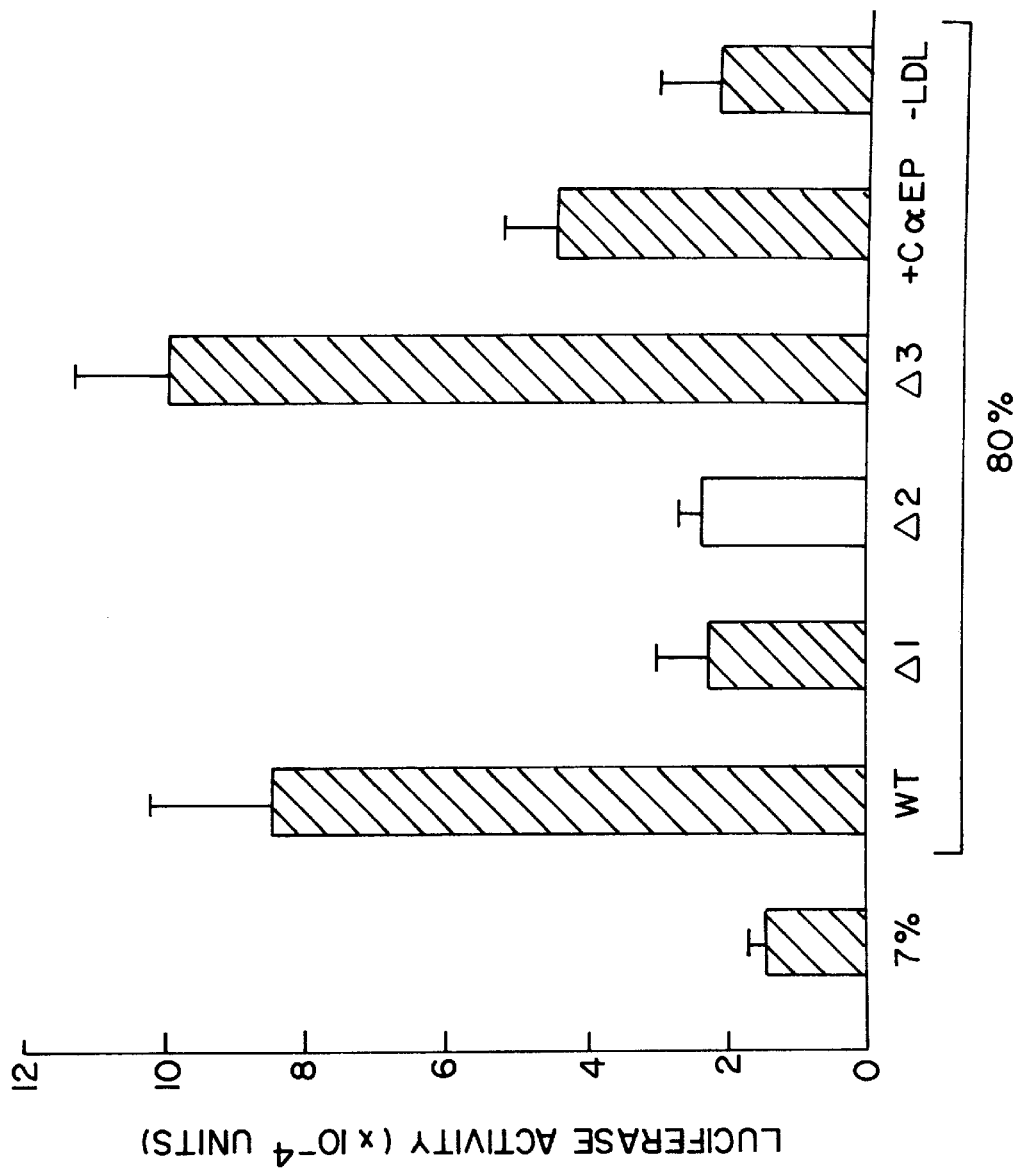
FIG. 15 illustrates luciferase activity from pGL3 driven by wild-type or mutant caveolin promoters. Δ1, Δ2 and Δ3 refer to promoter mutants from which SRE-like sequences at −646, −395 and −287 bp (FIG. 1) had been deleted. Fibroblast monolayers transiently transfected with wild-type or mutant caveolin promoters (Δ1, Δ2 or Δ3) were incubated with 80% v/v native human plasma for 3 h at 37° C. Other transfected cells monolayers were incubated with 80% v/v native plasma in the presence of 50 μM cholesterol α-epoxide, or with plasma from which LDL had been removed by heparin affinity chromatography. Values shown are means ± one SD for 3–5 determinations. Luciferase yield, determined as described herein, did not differ significantly from baseline values when the wild type caveolin promoter was inserted in reverse orientation, or in the absence of cell lysate.

Deletional mutagenesis of individual SRE-like sequences within the caveolin promoter was carried out as described under Experimental Methods. Deletion of the SRE-like sequence at –646 bp was associated with an almost complete (~90%) loss of the stimulation of luciferase expression observed when cells were transfected with vector containing the wild type promoter (FIG. 15). A comparable loss of activity was observed when the second SRE-like site at –395 bp was deleted. In contrast, when the SRE-like sequence at –287 bp was selectively excised from the promoter, luciferase expression was slightly higher than with the wild-type sequence. Together, these results indicate that the SRE-like sequences at –646 and at –395 bp are both required for the response of the caveolin gene promoter to LDL-derived cholesterol, since deletion of either was associated with an almost complete loss of activity. In contrast, the third site was inactive in this assay.

Gel Shift Analysis of the Caveolin Gene Promoter Region

These experiments were carried out to determine whether nucleoproteins were complexed with the SRE-like elements of the caveolin gene promoter as part of the transcriptional response to LDL. Incubation of nuclear extract with $^{32}P$-labeled promoter DNA fragments was carried out as described above. Binding of a nucleoprotein to the DNA fragment generates a labeled complex of increased molecular weight (relative to unbound DNA) with a decreased migration rate during electrophoresis. The wild type DNA fragment corresponding to the promoter region surrounding each SRE-like sequence formed a single shifted DNA-protein complex. A 200-fold excess of unlabeled homologous oligonucleotide competitor displaced nucleoprotein binding to the labeled DNA. In contrast, inclusion of an equivalent molar concentration of DNA lacking the 10-base SRE-like sequence led to no loss of shifted label. These results confirm that nuclear extract contains nucleoprotein binding to the SRE-like sequences in the caveolin gene promoter region.

DNAase I Footprint Analysis

The data obtained using promoter constructs ligated to luciferase indicated the presence of two essential SRE-like sequences at –646 and –395 bp in the 5'-flanking region of the caveolin gene. DNAase I protection assays were carried out using end-labeled DNA fragments encompassing either the –646 or the –395 bp site. Fragments were incubated with nuclear extract and the sequence of protected bases in both cases determined. In the case of the first site, the protected region extended from –646 to –637 bp. For the second, it extended between –401 and –386 bp.

Mechanism of SRE-mediated Regulation of Caveolin Gene Transcription

The identity of nucleoproteins binding to the essential caveolin GC-rich boxes at –646 and –395 bp was further analyzed by incubating each oligonucleotide and nuclear extract from cells equilibrated with 7% v/v plasma with anti-SREBP-1 or anti-Sp-1 antibodies. Formation of an IgG-nucleoprotein-DNA ternary complex was indicated by the presence of a supershift complex following reaction of the GC-rich sequence at –395 bp. No complex was detected following addition of antibody against Sp1-family or Sp-2, -3 or -4. The GC-rich sequence at –646 bp did not react with any of the antibodies tested.

The biologically active, soluble fragment of SREBP promotes the transcription of FC-dependent genes including the LDL receptor protein. Release of soluble SREBP from the endoplasmic reticulum is mediated by the action of two proteases, one sterol-inhibited (Wang X et al. (1994) *Cell* 77: 53–62, Sakai et al. (1996) *Cell* 85: 1037–1046). Soluble SREBP is degraded by a third, cysteine-dependent, proteasomal protease (Wang X et al. (1994) *Cell* 77: 53–62). As a result, LDL cholesterol inhibited LDL receptor gene transcription rates, while the cysteine protease inhibitor ALLN superactivated this and other SREBP-dependent genes regardless of the level of FC. In contrast, in the present experiments, ALLN superinhibited the expression of the caveolin gene. Caveolin mRNA levels were reduced to the same, minimal level, whether the cells were equilibrated in 7% v/v or 80% v/v plasma.

Discussion

Many steps of cellular cholesterol metabolism in peripheral cells are mediated by gene products whose equilibrium mRNA levels are FC-sensitive. These steps include reactions catalyzed by the LDL receptor protein, and HMG CoA synthase, HMG CoA reductase, farnesyl pyrophosphate synthase and squalene oxidase among enzymes of FC synthesis (Scherer (1995) *J. Biol. Chem.* 270: 16395–16401, Goldstein et al. (1990) *Nature* 343: 425–430, Spear et al. (1994) *J. Biol. Chem.* 269: 25212–25218, Guan et al. (1995) *J. Biol. Chem.* 270: 21958–21965). Equilibrium mRNA levels for all these proteins are reduced when cellular FC levels increase, often as a result of changes both in transcription rate and in mRNA stability (Scherer (1995) *J. Biol. Chem.* 270: 16395–16401). As a result, entry of new FC into regulatory pools within the cell is decreased. In contrast, caveolin mRNA levels are increased under the same conditions, and efflux of FC from the cell stimulated (Fielding et al. (1997) *Proc. Natl. Acad. Sci. USA* 94: 3753–3758). Nevertheless, the present study shows that these opposite effects are achieved using the same mechanisms.

Nucleoprotein-mediated regulation of the genes coding for HMGCoA reductase and the LDL receptor protein have been studied in particular detail (Wang X et al. (1994) *Cell* 77: 53–62, Sakai et al. (1996) *Cell* 85: 1037–1046). The transcription factor SREBP-1 (first identified as the adipocyte determination and differentiation factor, ADD1) (Tontonoz et al. (1993) *Mol. Cell Biol.* 13, 4753–4759) plays a major role. A soluble SREBP fragment released from the endoplasmic reticulum enters the nucleus to bind to one of several SREs in the LDL receptor promoter, stimulating transcription. Transcriptional regulation also involves Sp1, a second nucleoprotein binding to an adjacent site (Dawson et al. (1988) *J. Biol. Chem.* 263: 3372–3379). Two essential SRE-like sequences were identified within the caveolin promoter, at −395 and −646 bp. The first of these binds SREBP-1, shown by the supershift obtained when the corresponding antibody was present, but not Sp1, or other Sp family proteins. No binding of SREBP-1 or Sp proteins to the GC-rich box at −646 bp could be identified under the same conditions. SREBP-1 and a related transcriptional factor (SREBP-2) are considered equivalent in effect (Sheng et al. (1995) *Proc. Natl. Acad. Sci. USA* 92: 935–938). This makes it unlikely that other SREBP-related proteins react at −646 bp. Nevertheless, the present study clearly shows that SREBP-1 can bind to the promoter region of caveolin, a gene upregulated by FC, as well as LDL receptor protein and HMG CoA reductase, genes whose expression is FC-suppressed. Two alternative mechanisms might explain this divergence. FC originating from the selective uptake of FC from LDL might increase the cleavage of SREBP at the endoplasmic reticulum, while FC from the endocytosis of intact LDL or cholesterogenesis does the opposite. This would need identification in the cell, for example by vesicle marker proteins, for FC of different origins. Alternatively FC might have a consistent, inhibitory effect on the cleavage of SREBP; in this case, the mature SREBP fragment would stimulate the transcription of the LDL receptor and reductase, and inhibit the transcription of caveolin.

These alternatives were distinguished with the inhibitor ALLN. By the first mechanism, ALLN would activate caveolin transcription; by the second, it would inhibit it. ALLN strongly inhibited caveolin mRNA levels even below the level expressed in cells equilibrated in 7% v/v plasma. ALLN completely prevented the activation of caveolin mRNA levels observed in 80% v/v plasma in the absence of inhibitor. This finding suggests that SRBP-1 inhibits caveolin transcription, in contrast to its effects on other FC-sensitive promoters, although effects of ALLN with other nuclear factors may also be important. Further research will be needed to indicate if the upregulation of caveolin gene transcription in 80% v/v plasma medium is mediated by the physical displacement of SREBP-1 from the −395 bp site, and the possible roles of other transcription factors and enhancer proteins.

FC-sensitive genes mediated by the SREBP mechanism have so far involved only the input side of regulation, the endocytosis of LDL or the new synthesis of FC. In quiescent cells including confluent fibroblasts, the activity of these pathways is very low, yet cellular FC level was actively regulated at the level of efflux (Parton et al. (1994) *Science* 269: 1398–1399, Fielding et al. (1997) *Proc. Natl. Acad. Sci. USA* 94: 3753–3758). The present study suggests that the SRE/SREBP mechanism, previously shown to regulate FC influx, can regulate both influx and efflux. This finding extends the role of SREBP to quiescent cells, and suggests it may exert coordinate control over all the major pathways of cholesterol homeostasis. Finally, the observation that caveolin expression is regulated by the SRE/SREBP pathway substantiates the role of caveolin and caveolae, recently identified, as a significant element in FC homeostasis.

Example 4

Role of Caveolin in Intracellular Cholesterol Transport in Synchronized Human Skin Fibroblasts In this experiment, serum-maintained normal human skin fibroblasts were released into synchrony from aphidicolin arrest. Free cholesterol (FC) homeostasis was determined at intervals during the cell cycle. FC mass per cell doubled following S-phase, reaching its maximum shortly before mitosis. This increase was the result of both a stimulation of the rate of selective uptake of FC from medium lipoproteins, and a marked inhibition of FC efflux. Low rates of cholesterol synthesis and endocytosis of low density lipoprotein observed in the arrested cells were not increased during the cell cycle. Selective uptake of cholesteryl esters from medium lipoproteins was undetectable. The mechanism of the regulation of FC efflux during the mitotic cycle was further investigated. FC efflux in quiescent peripheral cells has been linked to the expression of caveolin, the structural protein of cell surface caveolae, suggested as a portal for FC efflux (Fielding & Fielding, (1996) *Biochemistry* 35:14932–14938). Decrease in caveolin mRNA levels in early S-phase was associated with a delayed reduction in the level of FC in cell surface caveolae, assayed with cholesterol oxidase, and in FC efflux. To test the hypothesis that expression of caveolin directly regulated FC efflux during cell division, arrested and dividing cells were transfected with human caveolin cDNA. FC accumulation at S-phase and mitosis were both marked inhibited (>70%) compared to control values, while caveolar FC available for efflux had doubled. These data provide evidence for a key role for caveolin in the cell cycle, mediated at least in part by its effects on FC homeostasis.

Materials and Methods

Cell Culture and Synchronization

Normal human skin fibroblasts were cultured in 10% fetal calf serum in Dulbecco's modified Eagles medium (DMEM). Cells were plated into 3.5 cm dishes at an initial density of $3-4\times10^4$ cells/dish, or at comparable densities in 6 cm dishes. After 3 days, dishes were incubated with aphidicolin (4 µg/ml)(CalBiochem, San Diego, Calif.) to inhibit DNA polymerase, leading to cell arrest immediately before S-phase (Tobey et al. (1988) Expt. Cell Res. 179400–179416). After 24 h incubation with aphidicolin, the inhibitor was removed for a further 12 h, then restored for a 'double block' at 8 µg/ml for a further 24 h (Sourlingas et al. (1996) Anal. Biochem. 234:104–107). After final removal from inhibitor into 10% serum-DME medium, the cells during incubation over the next 32 h at 37° C. At intervals, dishes were collected to determine progression through the cell cycle, and rates of FC synthesis and transport. In some experiments, normal human plasma was used in place of fetal calf serum. Blood was drawn after an overnight (16 h) fast into polyvinyl tubes containing streptokinase (100 U/ml final concentration) as anticoagulant (Fielding et al. (1991) Biochemistry 30:8551–8557).

Flow Cytometry

Cells arrested with aphidocolin, or at intervals after removal of inhibitor, were stained with bromodeoxyuridine (BrdU), trypsinized, and fixed at −20° C. in 95% ethanol. Nuclei were prepared with 0.08% pepsin, then resuspended in 0.01M Hepes buffer, pH 7.4 containing 10% fetal calf serum. Anti-BrdU antibody coupled to fluorescein isothiocyanate (Molecular Probes, XX, OR) was added for 30 min at 4° C. The nuclei were finally stained with propidium iodide (50 µg/ml) for 15 min at 37° C. Flow cytometry was carried out with a computerized Coulter EPICS cytometer (Tisty et al. (1995) Meth. Enzymol. 254: 125–133).

Determination of Cholesterol Mass

Fibroblast monolayers were dissolved in 0.2N NaOH, and extracted with equal volumes of methanol and $CHCl_3$. Portions of $CHCl_3$ phase were dried under $N_2$. FC mass was determined fluorimetrically with cholesterol oxidase, using authentic FC as standard (Heider et al. (1978) J. Lipid Res. 19: 514–518). Total cholesterol (FC+cholesteryl ester) was assayed with cholesterol oxidase in the presence of cholesterol esterase.

In some experiments, the cells were preequilibrated($2\times24$ h) with 1,2-$^3$H-FC (NEN, Boston, Mass.; 55–60 Ci/mmol). Label was dried under $N_2$, dissolved in ethanol, and incorporated with stirring into fetal calf serum maintained at 37° C. After equilibration (60 min, 37° C.) the serum was diluted into DMEM and added to individual cell monolayers. Final cellular FC specific activity was determined from FC mass, assayed as described above, and by liquid scintillation spectrometry. Cell and medium specific activity were consistent ±5%, and were $1.2-3.6\times10^5$ dpm/g FC in individual experiments.

Assay of FC Efflux and FC Synthesis

FC efflux was assayed from $^3$H-FC cells, labeled as described above, to unlabeled plasma medium containing 10–80% v/v plasma in DMEM in different experiments. Briefly, labeled cells were washed (×3) in phosphate-buffered saline (PBS) then incubated with unlabeled LDL (100–150 µg/ml FC) for 10 min at 37° C. to dissociate any LDL adsorbed to the cell surface (Fielding et al. (1995) Biochemistry 34:14237–14244). After washing with PBS-human serum albumin (4 mg/ml, pH 7.4) and three times with PBS, prewarmed plasma-DMEM was added for 3 min at 37° C. A 0.7 ml sample was collected, and chilled on ice. The medium was microfuged to precipitate any cellular debris. A 0.5 ml portion of supernatant was taken for liquid scintillation counting. FC efflux was linear over the 3 min period (Kawano et al. (1993) Biochemistry 32:5025–5028). The rate of FC efflux (ng/min) was calculated from the rate of appearance of medium label÷cell FC specific radioactivity.

FC influx was measured using comparable techniques, as the rate of uptake of $^3$H-FC from native plasma or heparin-affinity isolated LDL pre-labeled from H-FC-albumin-agarose covalent complex (Miida et al. (1990) Biochemistry 29:10469–10474). The specific activity of plasma or LDL FC, and the rate of FC influx (ng/min) was calculated as described above for FC efflux.

Rate of FC Synthesis

FC synthesis was estimated as previously as the rate of incorporation of 2-$^{14}$C-acetate into digitonin-precipitable sterols (Gospodarowicz et al. (1978) J. Biol. Chem.). Labeled acetate (final concentration 0.02 mM) was incubated with arrested or synchronized fibroblast monolayers in 10% fetal calf serum-DMEM for 60 min at 37° C. Following incubation, the cells were dissolved in 0.2N NaOH. Cell lipids extracted into $CHCl_3$ as described above were fractionated by thin-layer chromatography on silica gel plates developed in petroleum ether-diethyl ether-acetic acid 80/20/1 v/v. The sterol band (Rf 0.3) was extracted with ethanol, and precipitated with digitonin after addition of cold carrier FC. >95% of $^{14}$C-label was recovered as digitonide under these conditions. The rate of FC synthesis was determined based on the incorporation of 14 acetate units per molecule of FC.

Rate of LDL Endocytosis

Total LDL endocytosis (receptor-mediated+nonspecific) was estimated in terms of the rate of production of TCA-soluble radioactivity from $^{125}$I protein-labeled lipoprotein. LDL was isolated by heparin-agarose affinity chromatography and by density ultracentrifugation between density limits 1.019 and 1.063 g/ml. LDL protein was labeled with $^{125}$I by the iodine monochloride method (Markwell (1982) Anal. Biochem. 125:427–432), then dialyzed overnight against PBS-0.001M disodium-EDTA, pH 7.4. >99% of label was precipitated with 10% w/v trichloroacetic acid. LDL protein specific radioactivity was 880–940 dpm/µg. Arrested or synchronized cells were washed three times with PBS, then incubated with 8–10 µg $^{125}$I-labeled LDL in PBS-human serum albumin (4 mg/ml, pH 7.4) for 60 min at 37° C. Following incubation, protein was precipitated from the medium with TCA (final concentration 10% w/v). Supernatant (0.5 ml) was mixed with 5 λ of 40% w/v aqueous KI and 20 λ of 30% w/v $H_2O_2$. After extraction of free I with chloroform (1 ml) portions of supernatant aqueous phase were assayed for $^{125}$I-radioactivity (Goldstein eet al. (1974) J. Biol. Chem., 249: 5153–5162). The rate of endocytosis of LDL cholesterol was estimated as TCA-soluble $^{125}$I-label, multiplied by 1.33 to correct for the ratio between protein (25.0% w/w), FC (8.6% w/w) and cholesteryl ester (41.9% w/w, equivalent to 25.2% sterol mass)( Fielding et al. (1991) In 'Biochemistry of Lipids, Lipoproteins and Membranes, Vanced D. E. & Vance J., eds., Elsveir Press, New York. pp 427–459).

Rate of Selective Uptake of CE from HDL

HDL was isolated by centrifugal flotation between density limits 1.063 and 1.12 g/ml. Following dialysis into PBS-0.001M EDTA, pH 7.4, HDL was labeled by exchange for 24 h at 37° C. with $^3$H-cholesteryl oleate (Amersham, Chicago, Ill.) adsorbed to celite (Gwynne et al. (1989) *J. Biol. Chem.*, 264: 8141–8150). More than 98% of CE label was recovered with HDL between the original density limits. Final specific activity was (0.5–0.8×10$^5$ cpm/µg CE. HDL (final concentration 20 µg HDL protein/ml in PBS-HSA) was incubated with arrested or synchronized cells for 60 min at 37° C. Following incubation, surface-bound label was dissociated with unlabeled HDL (10 min, 37° C.). The cell monolayers were washed with PBS-HAS and then three times with PBS. The cells were then dissolved in scintillation cocktail (3a70B, Research Products, Mount Prospect, Ill.) and internalized CE label determined.

Measurement of Cell Surface FC

The fraction of total cell FC accessible to cholesterol oxidase in unfixed fibroblast monolayers was assayed in cells prelabeled to equilibrium with $^3$H-FC as described previously. Dishes were cooled on ice, and washed with cold PBS-HAS and PBS. Cholesterol oxidase (Boehringer-Mannheim, Indianapolis, Ind.) was added to a final concentration of 1.0 U/ml. Incubation was carried out for 4 h at 0–2° C. to inhibit the exchange of intracellular $^3$H-FC with the cell surface (Fielding et al. (1996) *Biochemistry* 35:14932–14938). Under these conditions, reactivity with cholesterol oxidase was maximal. The cells were washed with cold PBS, then solubilized overnight with 0.2N NaOH. After extraction with methanol and CHCl$_3$ as described above, portions of CHCl$_3$ phase were fractionated on silica gel layers on plastic sheets developed in petroleum ether-diethyl ether-acetic acid 80/20/1 v/v. FC (Rf 0.3) and its oxidation product cholest-4-en-3-one (Rf 0.45) were identified using authentic lipid standards (Sigma, St Louis, Mo.). Both TLC spots were cut out and $^3$H-label determined.

Northern Blot Analysis of Caveolin

Total RNA was purified from arrested and synchronized cells using Rneasy kits (Qiagen, Chatsworth, Calif.). For Northern blotting, 4 µg of total RNA was applied to 1% agarose/formaldehyde gels. After electrophoresis and transfer to nylon membrane, caveolin mRNA was identified using random-primed $^{32}$P-labeled full length caveolin cDNA (Fielding et al. (1997) *Proc. Natl. Acad. Sci. USA*, 94: 3753–3758). cDNA for the 'housekeeping' gene GAPD (ATCC/NIH Repository, Rockville, Md.) was labeled with $^{32}$P in the same way. The level of each mRNA was estimated with a computerized densitometer (ImageQuant; Molecular Dynamics, Sunnyvale, Calif.) under conditions where signal was linear with RNA load applied. Caveolin mRNA levels during the cell cycle are expressed relative to GAPD in the same RNA sample.

Transfection with Caveolin cDNA

Fibroblasts were plated at a density of 1.7×10$^5$ cells per 6 cm dish. After 48 h they were transfected with 8 µg/dish of caveolin cDNA (838 bp)(Fielding et al. (1997) *Proc. Natl. Acad. Sci. USA*, 94: 3753–3758) subcloned in forward orientation in a pCDNA3 vector (Invitrogen, Carlsbad, Calif.). In some experiments plating and transfection were carried out on a one-third scale in 3.5 cm diameter dishes. Transfection was carried out using the calcium phosphate coprecipitation method (Profectin; Promega, Madison, Wis.) in 10% fetal calf serum-DMEM. After incubation for 16 h at 37° C., the medium was changed, and aphidicolin added using the protocol described above. Cells treated with empty vector+calcium phosphate or with calcium phosphate alone were included in these experiments as controls.

Results

FC Content of Synchronized Cells

Figure 16:
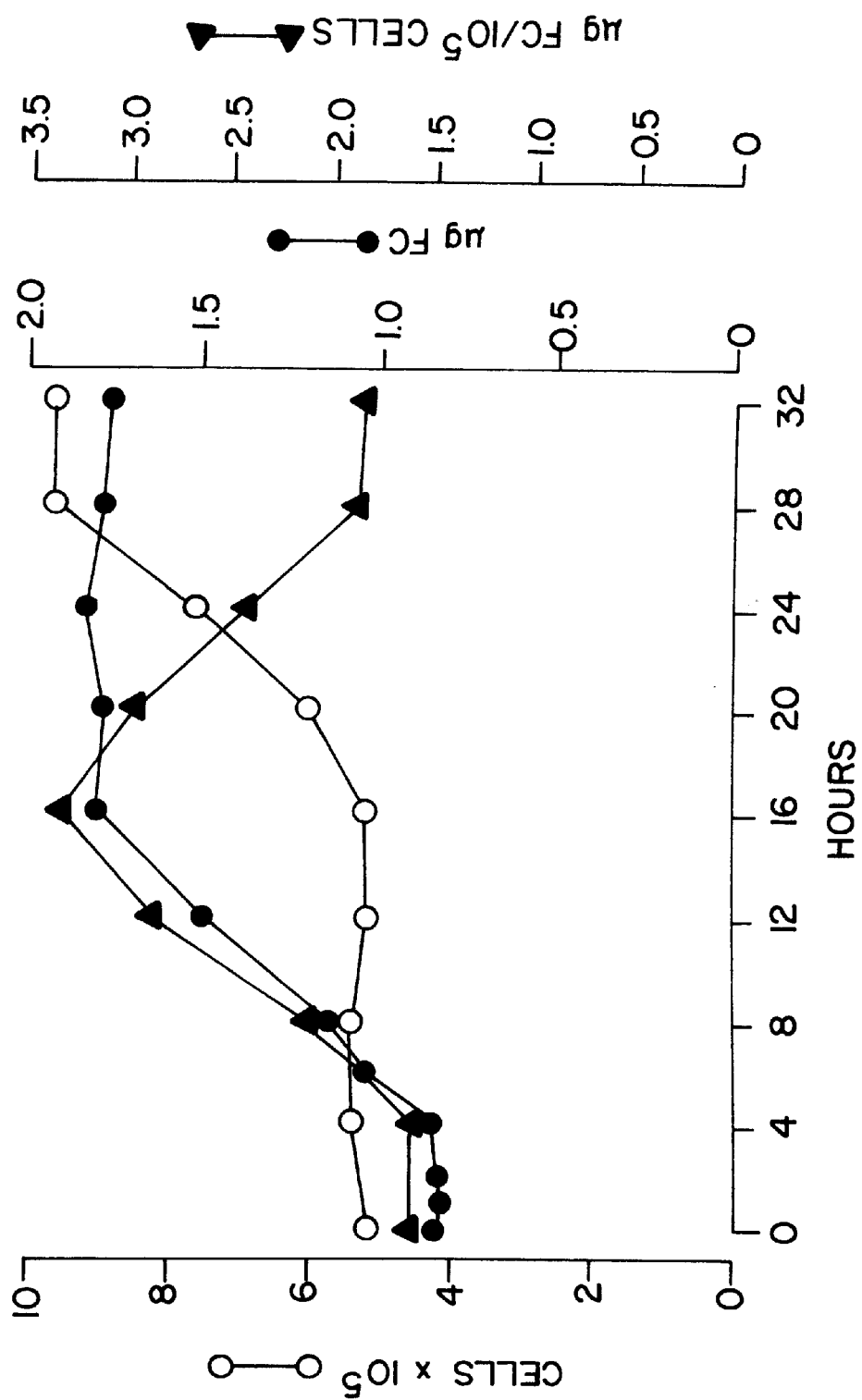
FIG. 16 shows cell FC content as a function of time following release from aphidicolin-mediated cytostasis. Open circles, cell number/6 cm dish; Closed circles, FC mass per 6 cm dish over the same time course. Closed triangles, FC mass per 10$^6$ cells over the same time course.

FC mass in cell monolayers released into synchrony from aphidocolin block remained constant for 2–4 h. This interval corresponded to the peak of S-phase. FC then doubled over the next ~12 h, prior to the inception of mitosis, as measured from cell number. As a result, when the data was expressed as FC/10$^6$ cells, cellular FC content was initially constant, increased transiently (8–16 h) then returned to its original value (FIG. 16).

Figure 17:
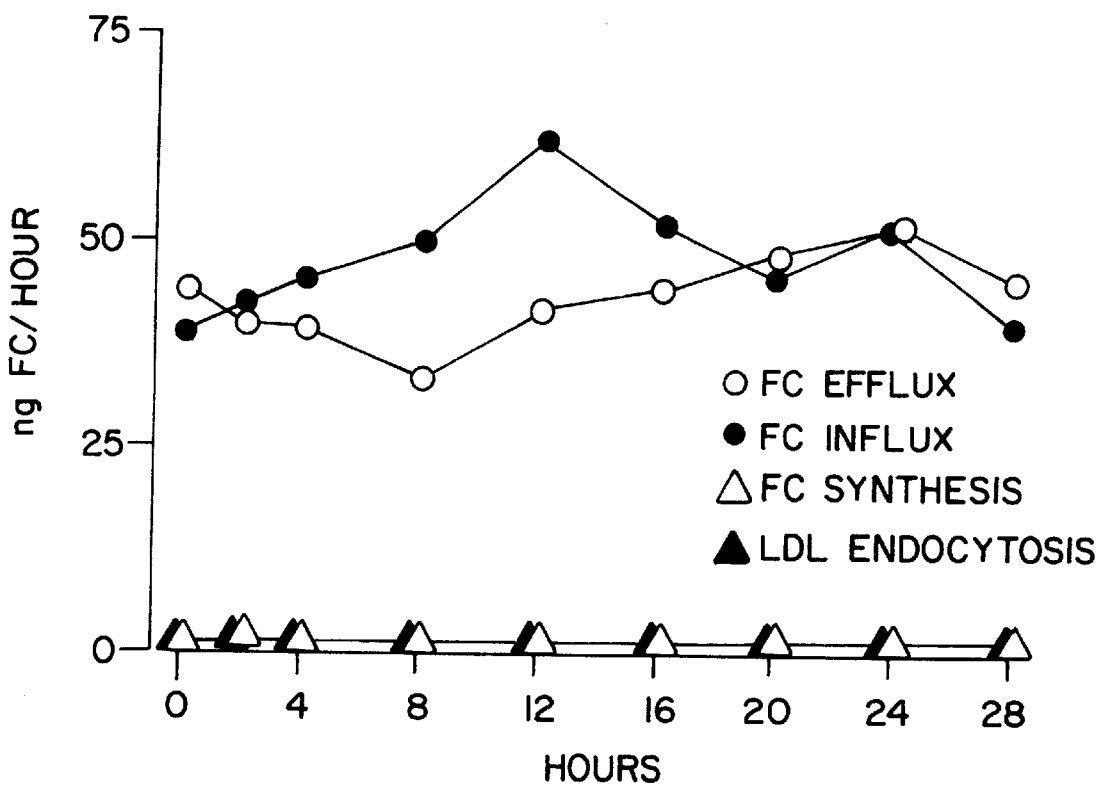
FIG. 17 shows FC homeostasis in synchronized human fibroblasts. Open circles, FC efflux measured as the rate of transfer of $^3$H-FC to the medium following the incubation of cells labeled to equilibrium in 10% v/v $^3$H-FC human serum-DMEM with unlabeled 10% serum-DMEM medium. Efflux rates (open circles) were calculated from a cell FC specific activity of 0.69×10$^5$ dpm/μg. Rates of influx (closed circles) were calculated from the rate of uptake of radioactivity from $^3$H-FC equilibrated 10% human serum (specific activity 0.69×10$^5$ dpm/μg) into unlabeled fibroblast monolayers. Both measurements were made simultaneously with equivalent dishes of cells. Open triangles, FC synthesis from 2-$^{14}$C-acetate. Rates of synthesis have been converted to ng FC/h from acetate specific activity and the incorporation of 14 2-C units/mole FC. Closed triangles, uptake of LDL total cholesterol, calculated from the rate of formation of TCA-soluble $^{125}$I-radioactivity from $^{125}$I-labeled LDL, as described under Experimental Methods.

In quiescent cells, FC mass remains constant even though a significant flux of FC through the cell was maintained. Both the endocytosis of LDL, and FC synthesis are down-regulated. FC uptake and efflux in 10% v/v plasma were determined as a function of time following the release of fibroblast monolayers from aphidocolin. Efflux was determined from the rate at which $^3$H-FC label appeared in unlabeled medium. Total uptake of FC from $^3$H-labeled medium into the cells was assayed over the same time period. Initial rates of influx and efflux were closely similar, consistent with the stable FC content observed in FIG. 16. Following release into S-phase, a significant decrease in the rate of FC efflux was observed, which was not restored until 16 h. A comparable increase in FC influx was measured over the same time period (FIG. 17).

Low rates of cholesterogenesis from 2-$^{14}$C-acetate were measured at all points the during cell cycle; these rates were not increased during the period at which the FC content of the cell monolayer was rapidly increasing (approximately 4–12 h). The rate of total endocytosis of LDL was measured with I-labeled $^{125}$LDL. This rate, while finite, like that of cholesterogenesis was low relative to the total flux of FC, and did not change appreciably during the cell cycle. Finally, the rate at which CE was selectively internalized from $^3$H-CE was determined. This reaction, catalyzed by the cell-surface SR-B1 receptor, most notably in hepatic, adrenal and gonadal cells, was not significantly increased above background rates in human fibroblasts released into cell division from aphidocolin.

Expression of Caveolin During the Cell Cycle

Figure 18:
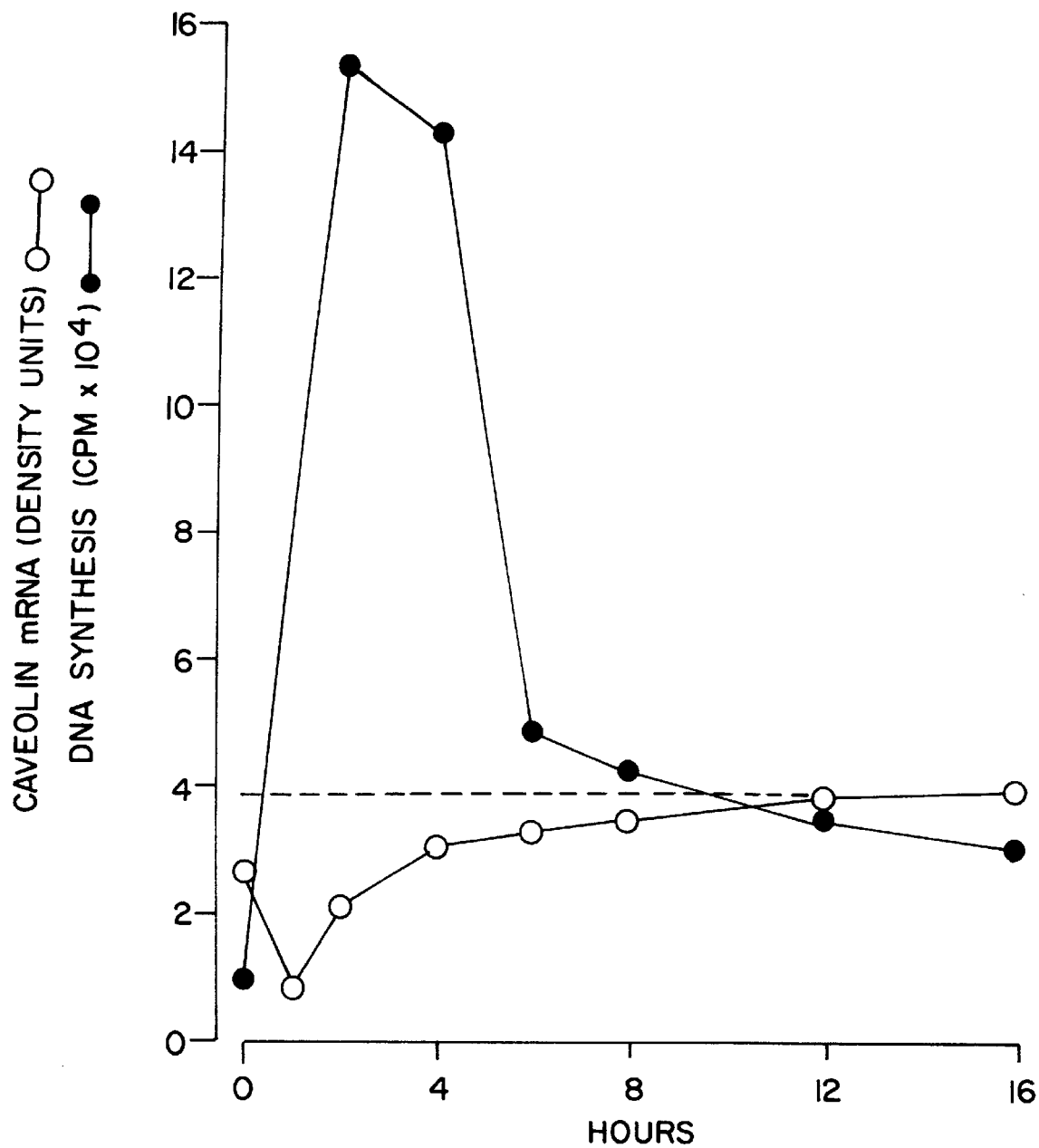
FIG. 18 shows expression of caveolin mRNA normalized to that of the housekeeping gene GAPD. The shaded portion represents the area under the curve calculated from arrested (zero time) caveolin concentration. A plot of the rate of DNA synthesis from $^3$H-thymidine (closed circles) measured at the same time (closed circles) is included to indicate S-phase in the same cells.

When fibroblast monolayers were released from arrest into cell division, entry into S-phase was associated with a marked (60–70%) decrease in the expression of caveolin mRNA both in absolute units and also relative to expression of the 'housekeeping' gene GAPD. mRNA levels returned to baseline over the next 8–12 h (FIG. 18).

Caveolar FC was assayed in terms of its reactivity with cholesterol oxidase in unfixed cells preequilibrated with $^3$H-FC. The oxidation product $^3$H-cholest-4-en-3-one and unmodified FC were separated from the total lipid of synchronized cells collected at intervals following release from arrest. Caveolar FC, like caveolin mRNA, decreased sharply at S-phase, and gradually returned to baseline (arrested) levels over the next 8–12 h. Under the same conditions, a parallel decrease in the efflux of $^3$H-FC from cells to the extracellular medium was observed. These data were consistent with earlier reports that reactivity with cholesterol oxidase reflects the mass of FC accessible to external lipoprotein acceptors, particularly HDL; and that FC efflux was linked to the expression of caveolin in these cells.

Effects of Transfection with Caveolin cDNA on FC Transport in Dividing Cells

The expression of caveolin and its effects of FC homeostasis were experimentally modulated in synchronized cells that had been transfected with human caveolin cDNA whose overexpression was directed by the viral sv40 promoter. In $^3$H-labeled aphidocolin-arrested cells, and at intervals after removal of inhibitor, cell mass and the expression of cell surface, caveolar FC were determined, using procedures described above.

Transfection with caveolin cDNA significantly reduced the accumulation of FC mass following S-phase that was observed in normal and sham-transfected cells. The increase observed was on average only ~40% of that required to double FC mass. There were also major differences in the mass of cell surface FC reactive with cholesterol oxidase. Initial levels were about 50% higher in cDNA-transfected compared to sham-transfected cells. Following entry into S-phase, a similar rapid decrease in oxidized FC was observed in both transfected and sham-transfected cell monolayers. In contrast, while recovery of baseline levels was slow and incomplete in the sham-transfected cells, in the cells transfected with caveolin cDNA, recovery was much more rapid, and exceeded normal baseline levels within 8 h of release from arrest.

If doubling of cell FC was required for effective entry into G2/M, then inhibition of FC accumulation mediated by caveolin might influence cell division. Overexpression of caveolin significantly reduced cell number after 32 h. Relative to original cell number, the data obtained represented an inhibition of 60–65% in the rate of cell division.

Discussion

Even in serum-maintained quiescent cells, whose overall FC content remains unchanged, FC is continuously interiorized from the medium, mainly via selective transfer from LDL. Such FC, after passing through intracellular vesicle compartments, is returned to the cell surface, from which it can be transferred to HDL (Fielding et al. (1996) Biochemistry 35: 14932–14938, Fielding et al. (1995) Biochemistry 34:14237–14244). It is believed that in human fibroblasts, and probably other peripheral cells, caveolae form a major site at which recycling or newly synthesized FC reaches the plasma membrane (Fielding et al. (1995) Biochemistry 34:14288–14292, Smart et al. (1996) J. Biol. Chem. 271:29427–29435, Fielding et al. (1995) Biochemistry 34:14237–14244).

As part of cell division, intracellular FC must double to restore the membrane composition of the products of mitosis. In cells chronically deprived of extracellular FC in vitro, this requirement can be met by upregulation of the FC synthesis pathway from acetate, and by induction of high affinity LDL receptors. It has been less clear which pathways might contribute to the FC required when cells divide under physiological conditions, in the presence of plasma lipoprotein.

In the present study, normal skin fibroblasts were arrested with aphidicolin. Following final removal of inhibitor, ~85% of cells were synchronized to enter S-phase, which was also marked by a stimulation (30–50-fold) in the rate of incorporation of $^3$H-thymidine into DNA. This efficiency is comparable to that reported for these cells with aphidicolin and alternative protocols, such as serum starvation and double thymidine block (Tobey et al. (1988) Expt. Cell Res. 179400–416). Mitosis was initiated at 16–20 h and was essentially complete by 24 h. Over this period the total FC content of the cells doubled as expected. Less expectedly, this change occurred after S-phase, but prior to the G2/M interface. That is, in these cells, FC accumulation preceded mitosis, and during a period of 8–12 h of approximately linear increase. This result implied an imbalance between FC efflux, and the sum of FC influx (by all pathways) and new synthesis, and a rate of FC accumulation of 100 ng/h/μg cell FC.

Contributors to this imbalance were identified by quantifying rates of FC influx, efflux and synthesis over the entire mitotic cycle. FC synthesis in arrested cells contributed only a small fraction of the total increase observable in cellular FC. FC synthesis rate was unchanged during the cell cycle, indicating that upregulation of the HMGCoA reductase pathway from acetate did not occur under these conditions. The uptake and degradation of LDL protein, while detectable in dividing fibroblasts, likewise was of a magnitude to contributed little to the observed increase in FC. This rate, reflecting the sum of receptor-mediated and "nonspecific" endocytosis (Brown et al. (1986) Science 232:32–47) was also unchanged during the cell cycle. The selective uptake of HDL cholesteryl ester, a major source of FC for cells utilizing cholesterol for bile acid and steroid hormone synthesis (Acton et al. (1996) Science, 271: 518–520), was undetectable, under conditions where a 1% contribution to total FC flux would have been identified. In contrast, significant changes during the cell cycle were detected in the rates of selective uptake of lipoprotein FC, and in FC efflux. These occurred in the period 4–16 h after release from aphidocolin arrest, and each contributed an estimated ~50% to the calculated net increase in cellular FC over the period. These data imply that in normal cell division, FC is acquired not by upregulation of the 'emergency' pathways which appear in peripheral cells transferred to lipoprotein deficient medium, but by an acquired imbalance in the pathways that stabilize the FC content of quiescent cells.

The mechanism by which FC is internalized from LDL is presently not well understood. A major part of this influx shares kinetic properties with a variety of protein ligands internalized via clathrin-coated pits. Uptake was blocked by N-ethyl maleimide and $NO_3^-$ (inhibitors of plasma membrane $H^+$-ATPases)( Fielding et al. (1995) Biochemistry 34:14237–14244) as well as by excess medium $Na^+$ or the absence of $K^+$ (Cupers et al. (1994) J. Cell. Biol., 127: 725–735), conditions believed to favor the dissociation of newly formed clathrin baskets. These properties are shared with the uptake of transferrin via its cell surface receptor, which in human fibroblasts is mediated exclusively by coated pits. Because the recycling of LDL-derived FC within the cell was unaffected by inhibitors of lysosomal function (Fielding et al. (1995) Biochemistry 34:14237–142449), it is possible that FC follows a nondegradative, recycling pathway bypassing the lysosomes, as has been, described for several recycling receptors, notably the transferrin receptor (Ghosh et al. (1994) J. Cell Sci., 107: 2177–2189). Stimulation of FC influx was seen mainly in the later part of the period during which cellular FC mass increased.

In contrast, decrease in FC efflux below initial (arrested) rates contributed mainly during the earlier part of FC accumulation (4–8 h). While the topic remains controversial, considerable evidence now links FC efflux in peripheral cells with the expression of cell surface caveolae. Caveolin antisense DNA proportionately downregulated both caveolin and FC efflux. Both the expression of caveolin and FC efflux were upregulated in parallel in the presence of increased levels of medium LDL (Bist et al. (1997) Proc. Natl. Acad. Sci. USA, 94: 10693–10698). The transfer of both recycling FC derived from LDL, and newly synthesized FC to the caveolae has been traced in pulse-chase experiments (Fielding et al. (1995) Biochemistry 34:14288–14292, Smart et al. (1996) J. Biol. Chem. 271:29427–29435, Brown ET AL. (1986) Science 232:32–47). Finally, the caveolar FC fraction, identified with cholesterol oxidase, was depleted following stimulated FC efflux to 80%/ v/v native plasma (Fielding et al. (1995) Biochemistry 34:14288–14292).

The present study identifies new links between caveolin, the expression of cell-surface caveolae, and the regulation of FC efflux. Caveolin mRNA levels (both in absolute terms and relative to the expression of the 'housekeeping' gene G3PD) were strongly downregulated following release from arrest into S-phase. These rates recovered during the period of FC accumulation so that initial rates had been reestablished by 16 h. A comparable but slightly delayed depression in FC accessible outside the cell was also observed with cholesterol oxidase. These events paralleled the reduction in efflux which contributed to FC accumulation.

A causative association between the expression of caveolin and the regulation of FC efflux was sought using fibroblasts transfected with caveolin cDNA under a viral promoter. If downregulation of FC efflux in late S-phase and early G2 contributed significantly to the FC accumulation which preceded mitosis, then the overexpression of caveolin, if resulting in increased EC efflux, might delay mitosis, at the same time increasing caveolar FC. Data in this study showed an almost complete inhibition of mitosis following caveolin DNA transfection. While baseline levels of caveolar FC, measured with cholesterol oxidase, were increased, the greatest effect was on the recovery of caveolar FC levels following S-phase. In sham-transfected cells, FC was sharply reduced 2 h after release from arrest, and was still below initial levels after 16 h. In cells transfected with caveolin cDNA, levels were restored to baseline within 4 h and rose thereafter. At the same time, the doubling of total cell FC which normally occurred between 4 and 12 h was >70% inhibited, as was mitosis at 32 h. These data appear to provide strong additional evidence linking the expression of caveolin to FC efflux and more importantly, to the regulation of cell division.

Inhibition of inappropriate cell division (40–75%) has been recently achieved by a number of laboratories, using DNA antisense to genes coding for growth factors or proteins of the mitotic cycle in cancer cells (Schwab et al. (1994) *Proc. Natl. Acad. Sci. USA,* 91: 10460–10464, Robinson et al.(1995) *Ann. Thor. Surg.,* 60: 1583–1591). Antisense to cycline kinase mRNAs (Chang et al. (1995) *Science,* 267: 518–522) or overexpression of a genetically engineered phosphorylation-resistant mutant of Rb (Morishita et al. (1994) *J. Clin. Invest.,* 93: 1458–1464) was shown to inhibit (50–85%) the multiplication of vascular smooth muscle cells. The inhibition by caveolin transfection of the rate of human fibroblast division in the present experiments were within a similar range. At the same time, stimulation of the caveolin pathway significantly reduced cell FC content. This research provides evidence that caveolin DNA therapy can have useful potential in cancer biology and atherosclerosis.

Example 5
Intracellular Cholesterol Transport in Synchronized Human Skin Fibroblasts[Ψ]

In this example, normal human skin fibroblasts maintained in serum-containing medium were synchronized with aphidicolin. After removal of inhibitor, free cholesterol (FC) homeostasis was determined at intervals during the following cell cycle. FC mass per cell doubled following S-phase, and reached its maximum well before mitosis. This increase was mainly the result of stimulation of the rate of selective uptake of FC from medium lipoproteins, and reduction of FC efflux. Rates of cholesterol synthesis, endocytosis of intact low density lipoprotein, and HDL receptor (CLA-1) activity were relatively low and little changed during the cell cycle. The expression of caveolin (structural protein of cell surface caveolae) and caveolar FC were decreased along with FC efflux. To test the hypothesis that regulation of caveolin expression could contribute to changes in FC efflux during cell division, cells were transfected with human caveolin cDNA, synchronized with aphidicolin, and then allowed to divide. In the transfected cells, caveolar FC and FC efflux were both increased. FC accumulation and entry into mitosis were markedly inhibited compared to controls. The contribution of transcriptional regulation to caveolin mRNA levels was determined with a 705 bp caveolin 5'-flanking sequence ligated to the pGL2 luciferase expression vector. Expression of the reporter gene was downregulated at S-phase of synchronized cells. Deletion of a hybrid E2F/Sp1-like site between −139 and −150 bp abolished this downregulation. These data are consistent with a role for caveolin in cell cycle kinetics, which may be mediated, at least in part, at the transcriptional level.

Materials and Methods
Cell Culture and Synchronization

Normal human skin fibroblasts and HeLa cells were maintained in 10% fetal bovine serum in Dulbecco's modified Eagles medium (DMEM). For individual experiments, cells were plated into 3.5 cm dishes (1 ml medium) at an initial density of $3-4\times10^4$ cells/dish, or with proportionately increased cell number and medium volume in 6 cm dishes. After 3 days, dishes were incubated with aphidicolin (4 $\mu$g/ml)(CalBiochem, San Diego, Calif.) to inhibit DNA polymerase, leading to cell arrest immediately prior to DNA synthesis (S-phase) (Tobey et al. (1988) *Exptl. Cell Res.* 179: 400–416, Sourlingas and Sekeri-Pataryas (1996) *Anal. Biochem.* 234: 104–107.). After 18 h incubation with aphidicolin, inhibitor was removed for a further 8 h, then restored at 8 $\mu$g/ml for a further 18 h. The second exposure to aphidicolin was previously shown to increase cell synchrony (Sourlingas and Sekeri-Pataryas (1996) *Anal. Biochem.* 234: 104–107). After final removal of the inhibitor, the cells were incubated in 10% serum-DMEM for up to 32 h at 37° C. Cell synchronization was assessed by flow cytometry using the cell permeable stain Hoechst 33342 (Molecular Probes, Eugene, Oreg.)(Haas-Kogan et al. (1995) *EMBO J.* 14: 461–472.). Cell suspensions were incubated at room temperature with 4 ug/ml Hoechst 33342 for 45 minutes. Samples were analysed on a FACStar Plus (Becton Dickinson, San Jose, Calif.). Data was analysed using Lysis II software (Becton Dickinson). 83.9±3.1% of cells were in synchrony at the beginning of S phase consistent with literature values (12–13). DNA formation from [methyl-$^3$H]-thymidine (NEN; 89 Ci mmol$^{-1}$; 10 $\mu$Ci per 3.5 ml dish) was measured as the rate of synthesis of TCA-insoluble label over 30 min at 37° C.

Determination of Cell FC and Protein Mass

Fibroblast monolayers were dissolved in 0.2N NaOH, then extracted with equal volumes of methanol and chloroform. Portions of chloroform phase were dried under $N_2$ then dispersed in 0.5% Triton X-100 in phosphate buffer (pH 7.4). FC mass was first determined with cholesterol oxidase using a fluorimetric assay (Heider and Boyett (1978) *J. Lipid Res.* 19: 514–518). Esterified cholesterol mass was then determined from the fluorescence increment observed after addition of cholesterol esterase to the same solution. Esterified cholesterol was <5% of FC under the conditions of the present experiments. The FC content of undiluted fetal bovine serum was 65–69 $\mu$g ml$_{-1}$. Cell FC at the beginning of each experiment (that is, after final removal of aphidicolin) was 0.5–1.1 $\mu$g per 3.5 cm dish.

In some experiments, the cells were preequilibrated (24 h) with two changes of medium labeled with 1,2-$^3$H-FC (NEN, Boston, Mass.; 55–60 Ci/mmol). Briefly, labeled FC was dried under $N_2$, and dissolved in ethanol. The ethanol solution was injected during stirring into fetal bovine serum maintained at 37° C. in a proportion in most experiments of 5 $\mu$Ci ml$^{-1}$ serum. After equilibration (60 min, 37° C.) the serum was diluted into DMEM and this medium was added to individual dishes of cells. Cellular FC specific activity was determined from FC mass, assayed as described above, and by liquid scintillation spectrometry. Cell and medium specific activity were both determined. These were consistent ±5% in the same experiment, and were 0.2–0.9×10$^5$ dpm $\mu$g$^{-1}$ FC in different experiments.

Assay of FC Efflux and Influx

FC efflux was assayed as the transfer of $^3$H-FC from labeled cells to 10% unlabeled serum-DMEM (Kawano et al. (1993) *Biochem.*, 32: 5025–5028). Fetal bovine or human LDL was isolated by heparin-agarose affinity chromatography and by ultracentrifugation between density limits 1.02 and 1.050 g/ml. Equilibrium-labeled cells were washed (×3) in phosphate-buffered saline (PBS). They were then incubated for 10 min at 37° C. with unlabeled human LDL (50–80 $\mu$g/ml FC) to dissociate any labeled lipoprotein particles still adsorbed to the cell surface, representing <2% of cell cholesterol (<12 ng FC, or <0.15% of LDL FC). This procedure was without effect on FC incorporated into the plasma membrane (Fielding and Fielding (1995) *Biochem.*, 34: 14237–14244). After washing with PBS-human serum albumin (4 mg/ml, pH 7.4)(PBS-HSA) and three times with PBS, prewarmed unlabeled 10% plasma-DMEM was added for 3–5 min at 37° C. Linearity of FC efflux under these conditions was established in preliminary experiments as previously described (Kawano et al. (1993) *Biochem.*, 32: 5025–5028). In subsequent experiments, a 0.7 ml sample was collected, and chilled on ice. The sample was microfuged to pellet any cellular debris. Finally, a 0.5 ml portion of supernatant was taken for analysis of radioactivity. FC efflux was linear over the 5 min assay period. FC efflux was calculated from the rate of appearance of medium label and cell FC specific radioactivity.

FC influx was measured as the rate of uptake of $^3$H-FC from labeled serum-DMEM medium (Fielding and Fielding (1995) *Biochem.*, 34: 14237–14244). Unlabeled cells were washed with PBS-HSA and PBS, then incubated for 5 min at 37° C. with $^3$H-FC labeled medium. Subsequently, the cells were incubated (10 min, 37° C.) with unlabeled LDL to exchange surface LDL, then washed with PBS-HSA and PBS, prior to extraction with CHCl$_3$-methanol. Portions of CHCl$_3$ phase were collected for analysis. From this data, and the specific activity of plasma or LDL FC, the rate of FC influx was calculated. The contribution of changes in influx and efflux rates to the increase in cellular FC observed during the cell cycle was estimated by summing the hourly difference between these rates over 28 h.

Rate of FC Synthesis $^{14}$C-acetate (NEN; 57 mCi mmol$^{-1}$) was incubated with arrested or dividing fibroblasts in 10% fetal bovine serum-DMEM at 37°. To establish conditions in which intracellular acetate pools were fully equilibrated, total FC synthesis rates over 28 h (one cell cycle) were assayed in the presence of 2 or 20 mM acetate (1–5×10$^6$ cpm $\mu$mole$^{-1}$). The cells were dissolved in 0.2N NaOH. Cell lipids extracted into CHCl$_3$ were fractionated by thin-layer chromatography on silica gel plates developed in petroleum ether-diethyl ether-acetic acid 80/20/1 v/v. FC was then determined as previously described (Fielding et al. (1978) *J. Biol. Chem.* 254: 749–755). Since synthesis rates were the same at both concentrations of acetate, subsequent incubations were carried out in 2 mM labeled acetate for 2–4 h at intervals during the cell cycle, using the same protocol.

Rate of LDL Endocytosis

Total endocytosis of LDL (sum of receptor-mediated and nonspecific uptake of intact lipoprotein particles) was estimated as the rate of production of TCA-soluble radioactivity generated from $^{125}$I protein-labeled LDL. LDL protein was labeled with $^{125}$I by the iodine monochloride method (Markwell (1982) *Anal. Biochem.* 125: 427–432) then dialyzed overnight against PBS-0.001M disodium-EDTA, pH 7.4. >99% of label was precipitated with 10% w/v trichloroacetic acid. LDL protein specific radioactivity was 880–940 dpm/$\mu$g. Arrested or synchronized cells were washed three times with PBS, then incubated with $^{125}$I-labeled LDL in PBS-HSA for 1–2 h at 37° C. Following incubation, protein was precipitated from the medium with TCA (final concentration 10% w/v). Supernatant (0.5 ml) was mixed with 5 $\lambda$ of 40% w/v aqueous KI and 20$\lambda$ of 30% w/v H$_2$O$_2$. After extraction of free I with chloroform (1 ml) portions of supernatant aqueous phase were assayed for $^{125}$I-radioactivity (Goldstein and Brown (1974) *J. Biol. Chem.* 249: 5153–5162). The rate of endocytosis of LDL total cholesterol was estimated from TCA-soluble $^{125}$I-protein specific activity, multiplied by 1.33 to correct for the ratio between protein (25.0% w/w), FC (8.6% w/w) and cholesteryl ester (41.9% w/w, equivalent to 25.2% sterol mass) (Fielding and Fielding (1991) in *Biochemistry of Lipids, Lipoproteins and Membranes*, Vance, D. E. and Vance, J., Eds, pp 427–459, Elsevir Press, New York, N.Y.).

Selective Uptake of HDL CE and Cholesterol Oleyl Ether

To determine activity of the HDL receptor CLA-1 fetal bovine or human HDL was isolated by centrifugal flotation between density limits 1.063 and 1.21 g/mL. Following dialysis into PBS-0.001M EDTA, pH 7.4, HDL cholesteryl ester was labeled by exchange for 24 h at 37° C. with $^3$H-cholesteryl oleate (Amersham, Chicago, Ill.) adsorbed to celite (Gwynne and Mahaffee (1989) *J. Biol. Chem.* 264: 8141–8150). More than 98% of cholesteryl ester label was recovered with HDL between the original density limits. Final specific activity was 0.5–2.6×10$^5$ cpm/$\mu$g CE. This HDL (final concentration 20–40 $\mu$g protein/mL in PBS-HSA) was incubated with arrested or dividing cells for 1–2 h at 37° C. Following incubation, surface-bound label was dissociated with unlabeled HDL (10 min, 37° C.) (Gwynne and Mahaffee (1989) *J. Biol. Chem.* 264: 8141–8150). Cell monolayers were washed with PBS-HSA and then three times with PBS. The cells were then assayed for CE label.

Selective uptake from HDL was also determined using the nonhydrolysable labeled CE analog [1$\alpha$,2$\alpha$-$^3$H]cholesteryl oleyl ether (Amersham Life Science, Arlington Heights, Ill., 50.0 Ci/mmol)(Rinniger and Pittman (1987) *J. Lipid Res.* 28: 1313–1325). The cholesteryl ether was incorporated into HDL as described above for cholesteryl oleate. Final specific activity was 3.2×10$^4$–2.7×10$^5$ cpm $\mu$g$^{-1}$ HDL esterified cholesterol. Incubation with cell monolayers was for 2 h at 37° C., followed by incubation with unlabeled HDL for 2 h.

Measurement of Cell Surface FC

Cell FC accessible to cholesterol oxidase was assayed in unfixed fibroblast monolayers which had been prelabeled to equilibrium with $^3$H-FC. Earlier studies by this laboratory (Fielding and Fielding (1995) *Biochem.* 34: 14288–14292; Fielding and Fielding (1996) *Biochem.* 35: 14932–14938) confirmed the original observation (Smart et al. (1994) *J. Cell Biol.* 127: 1185–1197) that the caveolar fraction of plasma membrane FC is specifically modified under these conditions. Specifically, the cells were cooled on ice, then washed with ice-cold PBS-HSA and then three times with PBS. Cholesterol oxidase (Boehringer-Mannheim, Indianapolis, Ind.) was added to a final concentration of 1.0

U/ml. Incubation was carried out on ice for 4 h. Under these conditions, reactivity with cholesterol oxidase reached a maximum (5). No uptake of trypan blue was detected after 4 h incubation with cholesterol oxidase (<1 in $10^4$ cells reactive). Cell permeability was also monitored as the appearance of lactate dehydrogenase (LDH) in the extracellular medium after 4 h with cholesterol oxidase. This was compared to the activity assayed in the same volume of cell lysate prepared with 0.5% sodium deoxycholate (Brasaemle and Attie (1990) *J. Lipid Res.* 31: 103–112). LDH activity was assayed with a Sigma Diagnostics kit (Sigma, St Louis, Mo.). Medium LDH activity was <0.1% that of total cell lysate, indicating negligible leakage of cell contents under the conditions used to measure cell surface FC. There was no difference in medium LDH levels in the presence or absence of cholesterol oxidase.

In individual experiments, cells that had been incubated with cholesterol oxidase were washed with ice-cold PBS, and solubilized overnight with 0.2N NaOH. Following extraction with methanol and chloroform, portions of chloroform phase were fractionated on silica gel layers on plastic sheets developed in petroleum ether-diethyl ether-acetic acid 80/20/1 v/v. FC (Rf 0.3) and its oxidation product cholest-4-en-3-one (Rf 0.45) were identified by their comigration with the corresponding lipid standards (Sigma, St Louis, Mo.). Lipid-containing areas, identified with iodine vapor, were excised and $^3$H-label determined. >98% of total $^3$H-label was recovered in the two fractions described.

Expression of Caveolin and CLA-1

Total RNA was purified with RNeasy kits (Qiagen, Chatsworth, Calif.). For Northern blotting, 4–10 μg of total RNA was applied to 1% agarose/formaldehyde gels. After transfer to nylon membranes, caveolin mRNA was identified using random-primed $^{32}$P-labeled full length caveolin cDNA (Bist et al. (1997) *Proc. Natl. Acad. Sci. USA* 94: 10693–10698) and quantitated from Kodak X-OMAT AR film with a computerized densitometer (Fielding et al. (1997) *Proc. Natl. Acad. Sci USA* 94: 3753–3758).

Caveolin protein was assayed from cell homogenates using 12% polyacrylamide gels. Separated proteins were electrotransferred to nitrocellulose sheets (0.2 μm pore size, S & S, Keene, N.H.). Following incubation with rabbit anti-human caveolin polyclonal antibody, blots were incubated with anti-rabbit IgG conjugated with horseradish peroxidase, and then visualized with SuperSignal CL-HRP substrate (Pierce, Rockford, Ill.). Following autoradiography, caveolin in different lanes was estimated by densitometry as described above.

The human cell-surface HDL receptor CLA-1 is homologous to the rodent receptor SR-BI (Calvo and Vega (1993) *J. Biol. Chem.* 268: 18929–18935). CLA-1 mRNA was probed with the oligonucleotide 5'-CAG AAT AGG CCT GAA TGG CCT CCT TAT CCT-3' (SEQ ID NO: 7) which corresponds to nucleotides 1514–1543 of the human CLA-1 cDNA sequence Liu et al. (1997) *J. Clin. Endocrinol. Metab.* 82: 2522–2527). Glyceraldehyde 3-phosphate dehydrogenase (GAPD) cDNA (pHcGAP, ATCC/NIH Repository, Rockville, Md.) was labeled with $^{32}$P in the same way. The level of mRNA in each lane was estimated with a computerized densitometer as described above. Caveolin and CLA-1 mRNA levels during the cell cycle were expressed relative to GAPD in the same total RNA sample. In view of the low levels of CLA-1 previously detected in fibroblastic cells in published studies (Calvo and Vega (1993) *J. Biol. Chem.* 268: 18929–18935) an equivalent mass of total RNA from unsynchronized HeLa cells, which express ~10-fold higher levels of CLA-1, was assayed simultaneously.

Transfection with Caveolin cDNA

Fibroblasts were plated at a density of $1.7\times10^5$ cells per 6 cm dish. After 24 h, transfection was carried out with 8 μg/dish of wild type caveolin cDNA subcloned into a pCDNA3 vector (InVitrogen, Carlsbad, Calif.). Transfection was carried out using the calcium phosphate coprecipitation method (Profectin; Promega, Madison, Wis.) in 10% fetal bovine serum-DMEM according to the manufacturer's instructions. After incubation for 16 h at 37° C., the medium was changed, and aphidicolin added using the protocol described above. Following removal of the inhibitor, total cell FC, FC reactive with cholesterol oxidase, and cell number were determined. Cells sham-transfected with empty vector were included in these experiments as controls. Transfection efficiency (47–54%) was determined using cells transfected with pSV-galactosidase.

Assay of Caveolin Gene Transcription Rates

A 705 bp BglII promoter fragment (26) was subcloned into the pGL3 luciferase vector (Promega) to generate pGL3-CAV. Human skin fibroblasts were cotransfected with pGL3-CAV, together with pSV-galactosidase to correct for any differences in transfection efficiency. The cells were then synchronized with aphidicolin according to the protocol described above. Immediately prior to the final removal of aphidicolin, and at intervals thereafter, individual dishes of cells were washed with PBS and lysed. Samples of lysate were assayed for luciferase activity with an analytical luminometer (Monolight; Analytical Luminescence Laboratories, San Diego). Galactosidase activity measured with X-Gal (CalBiochem, La Jolla, Calif.) was used as above as an internal control to correct for differences in transfection efficiency.

The caveolin promoter sequence TTGGCGGGCGGC (SEQ ID NO: 8) at –139 to –150 bp contains overlapping E2F- and Sp1-like binding sequences (TTGGCGC, SEQ ID NO: 9, and GGCGGGCGGC, SEQ ID NO: 10). Using the published caveolin gene 5'-flanking sequence (Bist et al. (1997) *Proc. Natl. Acad. Sci. USA* 94: 10693–10698) an oligonucleotide was synthesized of the sequence between –125 bp and –165 bp deleting residues –139 to –150 bp. Synthesis of mutant promoter DNA was cared out with a Stratagene QuickChange sitedirected mutagenesis kit to generate the mutant promoter. Mutant and wild type base sequences were reconfirmed prior to use in individual transfection experiments.

Results

Sources of FC in Dividing Cells

Following removal of aphidicolin, the FC mass of synchronized fibroblast monolayers remained unchanged for 2–4 h. This interval corresponded to the peak of S-phase, determined from the rate of DNA synthesis with $^3$H-thymidine. Total cell FC increased over the next 8–12 h. At the end of this period, FC content per cell had doubled. Over this interval, increase in cell FC was approximately linear with time. FC then remained unchanged for the rest of the cell cycle. No increase in cell number was observed prior to 20–24 h, but it had doubled by 28 h. Following cell division, FC per cell returned to its original value. In cells maintained in aphidicolin over the same period, there was no activation of DNA synthesis, nor did FC increase. These data show that the increase in cellular FC preceded cell division by 10–12 h in dividing human skin fibroblasts.

Those pathways contributing to increased cell FC mass were identified by assaying the rates of FC synthesis, LDL endocytosis, the selective uptake of lipoprotein FC and CE, and FC efflux during the cell cycle. In the arrested cells, rates of influx and efflux were similar as expected (Fielding and Fielding (1995) Biochem., 34: 14237–14244). In contrast, following the removal of aphidicolin, the rate of FC efflux decreased, and was not completely restored to baseline values until 16 h had elapsed. Over a similar period, the selective uptake of FC from LDL increased. By 16 h, FC influx and efflux were once more equivalent.

Total FC synthesis was 22.4±0.6 ng and 22.0±2.2 ng over 28 h in the presence of 2 mM and 20 mM acetate respectively (6 experiments, difference not significant) showing that cell acetate pools had been fully equilibrated. Over the same period, FC mass in the same dishes increased 760±60 ng (6 experiments). These experiments showed that newly synthesized FC contributed about 3% of the total increase in FC mass which occurred during the cell cycle. FC synthesis was also measured in 2.0 mM acetate both in cells arrested with aphidicolin, and at 2–4 h intervals following its removal. The rate of FC synthesis in the arrested cells (1.5±0.6 ng $h^{-1}$)(n=5) was unchanged during the following 28 h. This result indicated that synthesis was not upregulated over the period during which cell FC mass increased.

Endocytosis of $^{125}$I-LDL was determined under the same conditions of arrest and release into cell division as described above, at concentrations of fetal bovine or human LDL (6.5 μg FC $mL^{-1}$) equivalent to those in 10% fetal bovine serum. In fetal bovine serum, like human serum, the major plasma lipoprotein is a FC-rich LDL (Forte et al. (1981) Lipids 16: 240–245; Bauchart et al. (1989) J. Lipid Res. 30: 1499–1514). In arrested cell cultures, the rate of LDL protein degradation was 1.5±0.5 ng $h^{-1}$ (equivalent to 0.5 ng $h^{-1}$ LDL FC). This rate rose slightly (+50%) after 2 h then decreased to its original value at 4 h and for the remainder of the cell cycle. There was no difference in the rates of degradation of fetal bovine and human LDL. Total cholesterol entering the cell by the endocytosis of LDL over 28 h was 30±5 ng, representing about 2.5% of the total increase in cellular FC over the same period.

The contributions of changes in FC influx and PC efflux to the total increase in cell FC mass over the same period were calculated as described above. Total decrease in FC efflux from baseline rates over 16 h after initiation of the experiment averaged 310 ng (0.31±0.07 μg, 4 experiments). Total increase in FC influx from baseline rates under the same conditions was 360 ng (0.36±0.05 μg, 4 experiments) (Table 7). There was no significant difference between influx and efflux rates over the remainder of the cell cycle. These data indicate that decreased FC efflux, and increased selective uptake of FC from LDL, were important mechanisms leading to FC accumulation during the cell cycle.

TABLE 7

Contribution of FC influx and FC efflux to the increment of total cell FC.

| Expt | ΔFC[a] | ΔInflux[a] | ΔInflux (μg FC)$^{-1}$ | ΔEfflux[a] | ΔEfflux (μg FC)$^{-1}$ |
|---|---|---|---|---|---|
| 1 | 1.10 | 0.42 | 0.38 | 0.40 | 0.38 |
| 2 | 0.54 | 0.29 | 0.53 | 0.24 | 0.44 |
| 3 | 0.70 | 0.38 | 0.54 | 0.30 | 0.43 |
| 4 | 0.70 | 0.34 | 0.48 | 0.30 | 0.42 |
| Mean ± SD | 0.76 ± 0.24 | 0.36 ± 0.05 | 0.47 ± 0.06 | 0.31 ± 0.0.07 | 0.42 ± 0.03 |

Individual values are from three 3.5 cm dishes at each point. Increase in FC mass was determined fluorimetrically. Influx was estimated from using $^3$H-FC labeled serum medium over 5 min at 37° C., as described under Experimental Procedures. Efflux was determined as the rate of transfer of $^3$H-FC (5 min, 37° C.) from labeled cells to unlabeled medium as described under Experimental Methods. [a]as μg FC.

Individual values are from three 3.5 cm dishes at each point. Increase in FC mass was determined fluorimetrically. Influx was estimated from using $^3$H-FC labeled serum medium over 5 min at 37° C., as described under Experimental Procedures. Efflux was determined as the rate of transfer of $^3$H-FC (5 min, 37° C.) from labeled cells to unlabeled medium as described under Experimental Methods. [a]as μg FC.

The rate at which CE was internalized from fetal bovine or human $^3$H-CE-labeled HDL was also determined, using a lipoprotein FC concentration of 6.5 μg $ml^{-1}$. CE uptake under these conditions represents the sum of CE internalized by the endocytosis of intact HDL particles, and the selective uptake of HDL-CE. Recovery of label from the incubated cells was undetectable (<0.3 ng FC $h^{-1}$) under the conditions described, both in arrested cells, and following release into cell division.

This finding might be the result either of an effective absence of HDL receptor activity, or of an efficient recycling of internalized CE, after hydrolysis, to the extracellular medium. To address this point, measurements were also made using HDL labeled with $^3$H-cholesteryl oleyl ether, in place of $^3$H-cholesteryl oleate. Using this tracer, uptake of label in quiescent cells was equivalent to 3.0±1.2 ng FC $h^{-1}$ per μg cell FC (4 experiments). Using the correction factor described under Material and Methods, this represented about 6% of the total uptake of cholesterol by aphidicolin-inhibited cells. Uptake of ether label from HDL decreased to <2% of FC influx over the period (4–12 h) during which FC was accumulating in the cells, before returning towards baseline after 16 h.

Regulation of FC Efflux During the Cell Cycle

Figure 19:
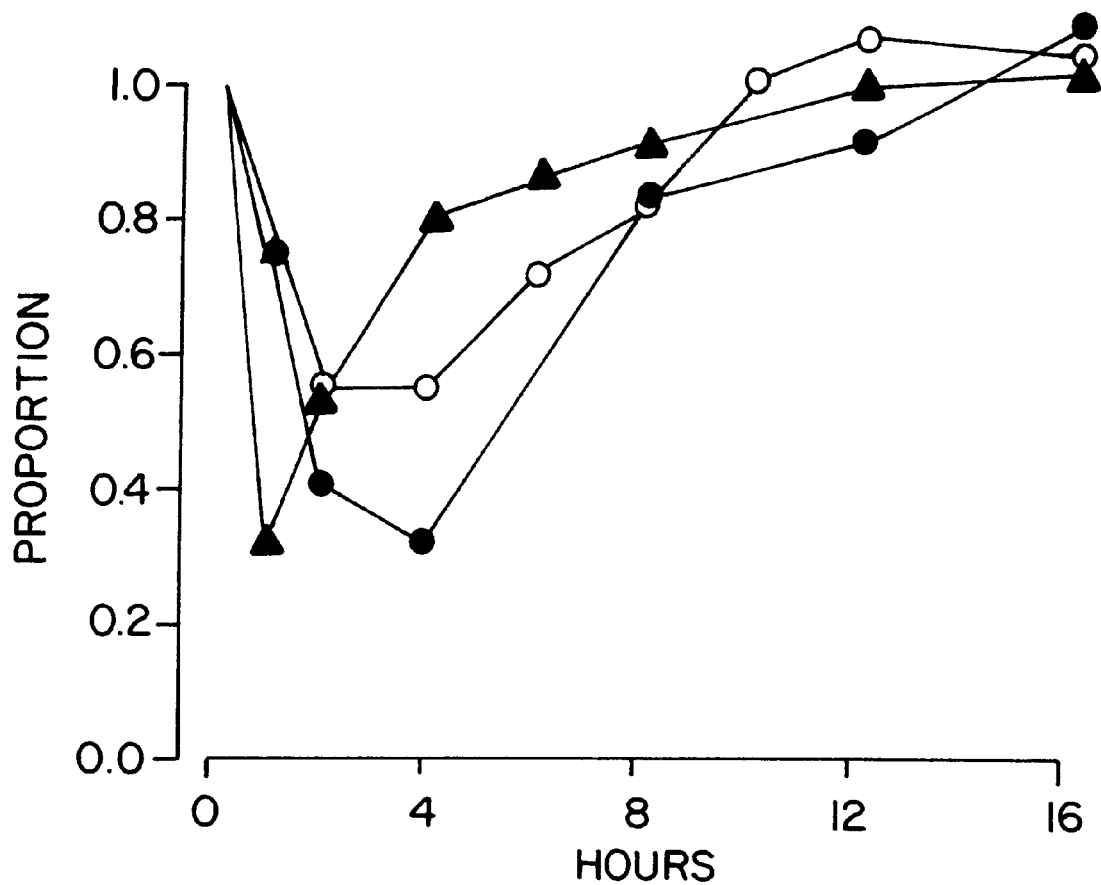
FIG. 19 shows parameters of caveolae expression in dividing human skin fibroblasts. Closed triangles, caveolin mRNA normalized to that of the housekeeping gene GAPD Open circles, caveolin protein assayed with rabbit polyclonal anti-human caveolin antibody. Closed circles, cell surface FC assayed with cholesterol oxidase expressed as a ratio to unmodified cell FC. Values are expressed relative to the same parameters in arrested cells (zero time).

Published studies have indicated that the expression of caveolin is linked to the level of intracellular cholesterol (Fielding et al. (1997) Proc. Natl. Acad. Sci USA 94: 3753–3758; Hailstones et al. (1998) J. Lipid Res. 39: 369–379) and could mediate, at least in part, FC efflux from quiescent cells, by regulating the level of FC in cell surface caveolae (Fielding and Fielding (1995) Biochem. 34: 14288–14292; Fielding and Fielding (1996) Biochem. 35: 14932–14938). The relevance of this mechanism for synchronized dividing skin fibroblasts was determined by comparing caveolin expression and FC efflux over the cell cycle. Following removal of aphidicolin, there was a marked decrease in the expression of caveolin mRNA. Caveolin mRNA levels declined steeply at 1–2 h, then recovered to baseline over the next 8–12 h (FIG. 19). In contrast, CLA-1 mRNA levels, which were low in arrested cells (0.1–0.2 those in HeLa cells) were unchanged over the cell cycle. Caveolin was assayed in extracts from arrested and dividing cells over the same time course. A decrease in caveolin protein similar to that of caveolin mRNA was observed. Caveolar FC was estimated in terms of its selective reactivity with cholesterol oxidase in cells preequilibrated with $^3$H-FC (Fielding and Fielding (1996) Biochem. 35: 14932–14938; Smart et al. (1994) J. Cell Biol. 127: 1185–1197). This parameter, like caveolin mRNA and protein, also decreased sharply at 2–4 h after removal of aphidicolin. It gradually returned to baseline (arrested) levels over the next 8–12 h.

Effects of Caveolin Overexpression on FC Transport and Rate of Mitosis

The preceding experiments confirmed in dividing cells the correlation between FC efflux and caveolin expression reported earlier, but did not establish a causal relationship between these parameters. FC homeostasis was therefore measured in synchronized cells which had been transfected with human caveolin cDNA prior to release from aphidicolin-mediated cytostasis. In $^3$H-FC labeled aphidicolin-arrested cells and at intervals following removal of the inhibitor, total and caveolar FC and FC efflux were measured in transfected and control cultures. Cell number was also measured, at zero time when aphidicolin was first removed, and 32 h after removal of inhibitor. Control assays were carried out simultaneously in cells transfected with empty vector.

Figure 20C:
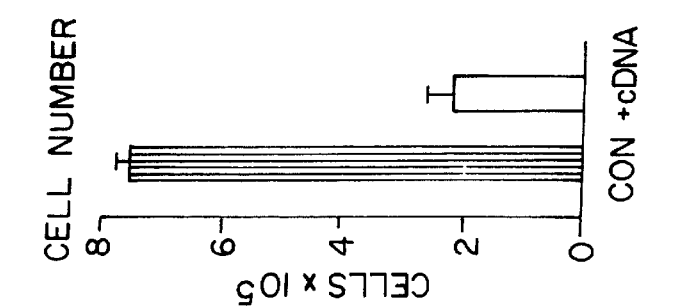
FIGS. 20A, 20B, and 20C. show the effects of transfection with human caveolin cDNA on FC homeostasis and mitosis in human skin fibroblasts.
Figure 20B:
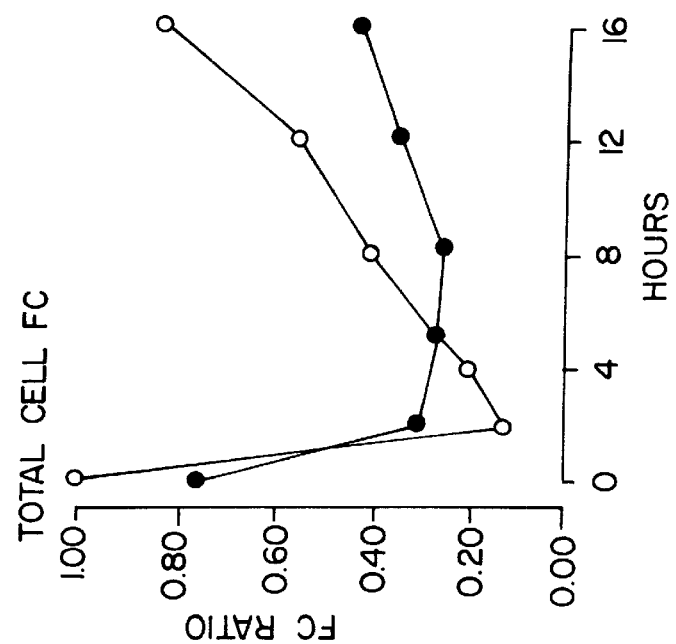
Figure 20A:
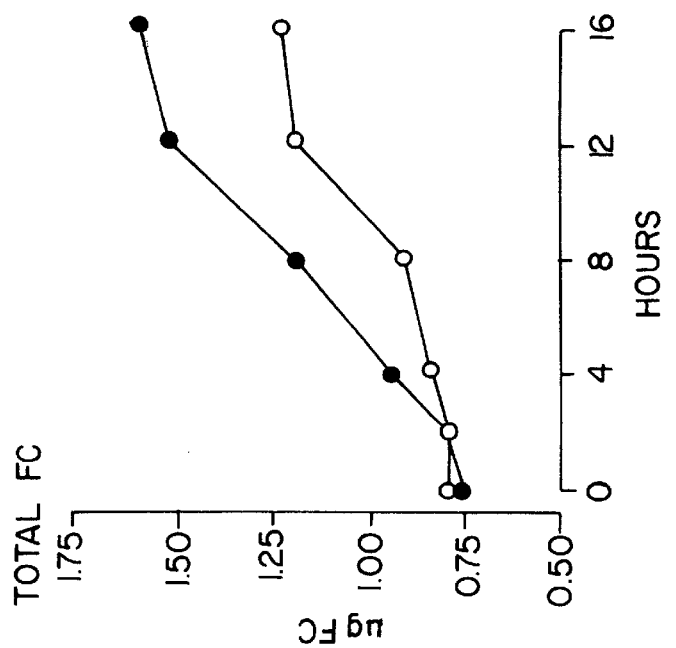

Transfection with caveolin cDNA reduced the accumulation of FC observed when synchronized cells entered the cell cycle. The increase in FC seen in transfected cells 16 h following removal of inhibitor was only 44±4% of that measured in non-transfected cells (FIG. 20A). Under the same conditions, FC efflux was 33–68% greater in transfected than in sham-transfected fibroblast cultures (Table 8). Transfection with empty vector was without effect on FC accumulation relative to nontransfected control cultures. Significant differences were also seen in cell surface FC reactive with cholesterol oxidase in cells transfected with caveolin cDNA, compared to controls. Caveolar FC measured with this assay was about 50% higher in arrested transfected cells compared to controls. Following entry into S-phase, there was a rapid decrease in caveolar FC in both transfected and control cells, but in the cells transfected with caveolin cDNA, recovery towards initial values was much more rapid, and by 24 h caveolar FC was double that measured in sham-transfected cells (FIG. 20B). These data are consistent in indicating a stimulation of FC transport and efflux in transfected cells, particularly in later stages of the cell cycle. Finally, transfection with caveolin cDNA significantly reduced the rate of cell division at 32 h (FIG. 20C). 32 h after removal of aphidicolin, the increase in cell number in the caveolin transfected monolayers was only 15.7±6.5% of the increase observed in control dishes (3 experiments).

TABLE 8

FC efflux from synchronized caveolin cDNA-transfected and control cells.

|  | 0 h | 12 h | 24 h |
| --- | --- | --- | --- |
| Caveolin transfected[a] | 34.8 ± 2.6* | 35.6 ± 17* | 50.8 ± 2.2** |
| Control[b] | 26.0 ± 0.9 | 26.5 ± 0.9 | 30.3 ± 1.7 |

[a]Fibroblast monolayers transfected with caveolin cDNA in correct orientation. [b]Fibroblast monolayers transfected with empty vector. Efflux $\mu g^{-1}$ cell FC is expressed as ng FC $h^{-1}$ transferred from monolayers equilibrium-labeled with $^3$H-FC to serum-DMEM medium at 37° C. Values shown are means ± one SD from three transfections. *p < 0.05; **p < 0.02.

Transcriptional Regulation of Caveolin Expression in Dividing Cells

Figure 21:
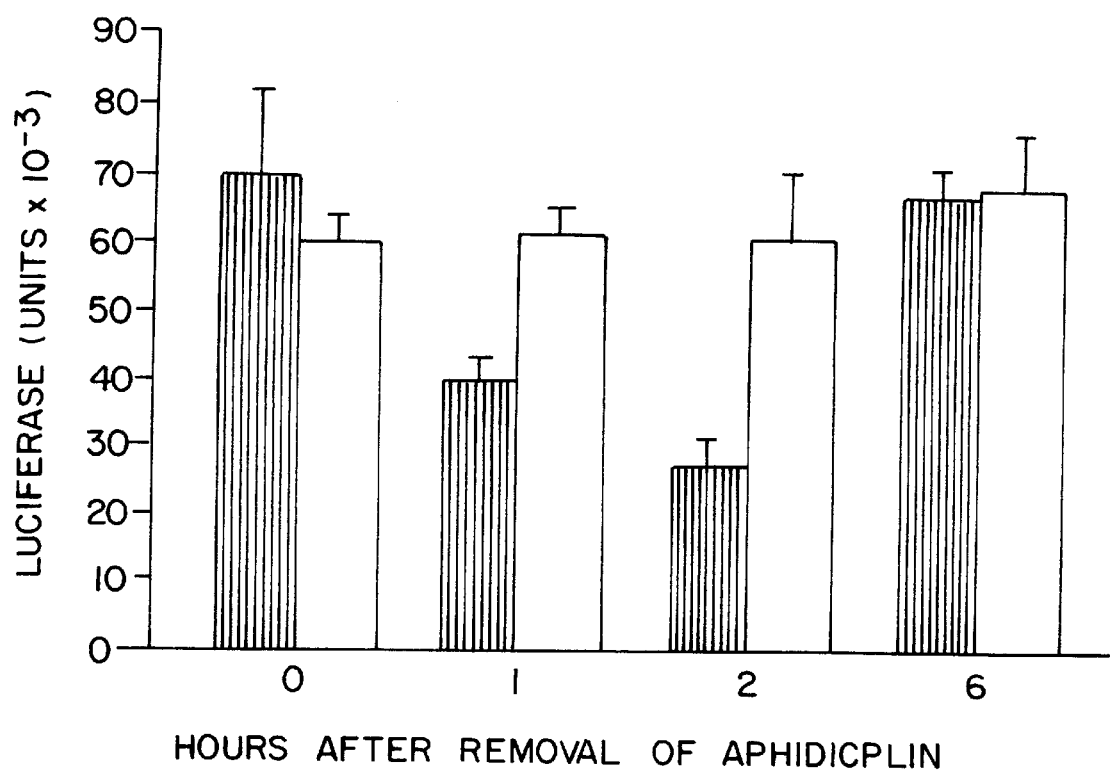
FIG. 21 illustrates the regulation of caveolin gene transcription at S-phase. Cell monolayers were first transfected with pGL3 luciferase vector ligated to either the wild type human caveolin promoter fragment (closed bars) or the mutant fragment from which—139 bp–150 bp had been excised (open bars). The cells were then synchronized with aphidicolin. Immediately before, and at the intervals shown after removal of inhibitor, the luciferase activity of cell lysates was determine d. Values shown represented means + one standard deviation (3 experiments).

The rate of caveolin gene transcription was determined in cells transfected with wild type caveolin promoter ligated to the luciferase expression vector pGL3. The transfected cells were then synchronized using aphidicolin. Following removal of inhibitor, luciferase yield was assayed at intervals during the cell cycle. As shown in FIG. 21, there was a marked decrease in the expression of the reporter gene during S-phase, with complete recovery by 6 h. In contrast, when the same measurements were carried out using the caveolin mutant promoter from which bp spanning −139 to −150 had been deleted, luciferase expression was constant over the cell cycle.

Discussion

When confluent human fibroblasts are maintained as monolayers in serum-containing medium, the need for new FC is low. Nevertheless, under these conditions, FC continues to be selectively internalized from medium lipoproteins, particularly LDL. Homeostasis is maintained by efflux of FC at an equivalent rate to the extracellular medium (Fielding and Fielding (1995) Biochem., 34: 14237–14244). FC influx and efflux were modified in parallel over at least a 10-fold range of extracellular FC concentration. This balance was not the result of increased simple exchange at the cell surface because FC was taken up from LDL mainly via coated pits, while much of FC efflux occurred from the caveolae, mostly to HDL. Additionally, pulse-chase experiments identified intermediate steps in the intracellular transport of LDL-derived $^3$H-FC to caveolae (Fielding and Fielding (1996) Biochem. 35: 14932–14938). In skin fibroblasts, FC homeostasis was mediated, at least in part, by the up- or down-regulation of caveolin, the structural protein of the caveolae which terminated the FC cycle in these cells. Changes in caveolin level were associated with parallel changes in the expression of caveolae at the cell surface (Hailstones et al. (1998) J. Lipid Res. 39: 369–379). The 5'-flanking region of the caveolin gene includes FC-responsive elements that upregulate caveolin mRNA levels in response to an increase in cellular FC (Fielding et al. (1997) Proc. Natl. Acad. Sci USA 94: 3753–3758). These data appear to support the hypothesis (Fielding and Fielding (1997) J. Lipid Res. 38: 1503–1521) that changes in the expression of caveolin might regulate FC efflux by adjusting the number and FC content of cell surface caveolae. In the present research, the mechanisms by which the FC requirements of dividing human fibroblasts in culture are met were investigated.

Mechanisms of FC Accumulation in Dividing Cells

In cultures of exponentially dividing cells, homeostatic mechanisms controlling the FC content of quiescent cell monolayers must be modified to allow the FC content per cell to remain the same as cell number increases. The present study shows that in dividing human skin fibroblasts which had been synchronized with aphidicolin, FC mass increased during a relatively short period (8–12 h) of the 24–28 h cycle. Additionally, this change was complete well before the end of the cell cycle (mitosis). Outside this period, cellular FC remained almost constant. While both cholesterogenesis and the endocytosis of LDL contributed slightly to the rise in cellular FC which was observed, the major contributors were an increase in the selective uptake of FC, and a decrease in FC efflux. That is, in dividing cells, FC accumulated mainly as the result of a temporary imbalance between the influx and efflux pathways that stabilize the FC content of quiescent cells. Quantitative measurements indicated that on average about 97% of the doubling in cellular FC assayed during the cell cycle was contributed by these two pathways under the conditions described.

The significance of the HDL receptor (SR-BI, CLA-1) in the selective uptake of CE from HDL in cells utilizing FC for steroid hormone and bile acid production is now well established (Acton et al. (1996) Science 271: 518–520). In the present study, the activity of the HDL receptor in human skin fibroblasts was very low, consistent with previous measurements in fibroblastic cells (Rinniger and Pittman (1987) J. Lipid Res. 28: 1313–1325). HDL receptor activity assayed with nonhydrolysable cholesterol oleyl ether decreased as the cells entered S-phase, during the period in which cellular FC mass increased. Its expression was low but unchanged over the same period. It is of interest that exogeneous FC loading was previously shown to depress the selective uptake of cholesterol ether (Id.). The parallel changes in SDL receptor activity and caveolin expression, may reflect, at least in part, the localization of the receptor to caveolae, previously reported in CHO cells (Babitt et al. (1997) J. Biol. Chem. 272: 13242–13249). Like cholesterol synthesis and LDL receptor-mediated endocytosis, selective CE uptake appears not to play a major role in FC balance in these cells. While the proportions of FC contributed by different mechanisms are likely to differ in different cell lines, the influx of preformed extracellular FC could be a significant contributor to cellular FC homeostasis in vivo.

Mechanism of Inhibition of FC Efflux During Cell Division

The mechanism by which FC is selectively internalized from plasma lipoproteins is presently not fully understood, although the pathway shares kinetic properties with those of receptor proteins internalized via clathrin-coated pits (Fielding and Fielding (1996) *Biochem.* 35: 14932–14938). FC influx from LDL may be itself receptor-mediated, or the changes observed in FC uptake during cell division could reflect the rate of coated vesicle formation. In contrast, the inhibition of FC efflux observed over the same time period was associated with marked changes in the expression of caveolin, a protein now broadly implicated in intracellular FC transport and efflux (Fielding and Fielding (1995) *Biochem.* 34: 14288–14292; Fielding and Fielding (1996) *Biochem.* 35: 14932–14938; Smart et al. (1996) *J. Biol. Chem.* 271: 29427–29435; Uittenbogaard et al. (1998) *J. Biol. Chem.* 273: 6525–6542). Caveolin antisense DNA downregulated both caveolin and FC efflux. The expression of caveolin and FC efflux were upregulated in parallel in the presence of increased levels of medium LDL and caveolae and caveolin were downregulated as cell FC decreased. The intracellular transport of both recycling and newly synthesized FC to the caveolae has been demonstrated.

The present study identifies new links between these factors. Caveolin mRNA and protein levels were strongly downregulated shortly after entry into the cell cycle. Over a similar period, caveolar FC and FC efflux were decreased. Transfection with caveolin cDNA was associated with increases in caveolar FC and FC efflux, and an inhibition of FC accumulation. Transfection with caveolin cDNA was also associated with a significant lag in cell division. This is consistent with the decreased growth rate in anchorage-dependent, caveolin-transfected cells reported earlier (Engelman et al. (1997) *J. Biol. Chem.* 272: 16374–16381). Taken together, these data provide strong evidence that the mechanism by which FC efflux is downregulated at S-phase depends on a corresponding decrease in the expression of caveolin.

Mechanism of Inhibition of Caveolin Expression During Cell Division

The expression of many genes important in cell cycle regulation is modified via the effects of transcription factors E2F and Sp1. Examples include cyclins and cyclin-dependent kinases, as well as enzymes of DNA synthesis such as polymerase D (Fanham et al. (1993) *Biochim. Biophys. Acta* 1155: 125–131; Zhao and Chang (1997) *J. Biol. Chem.* 272: 4869–4882). The caveolin gene 5'-flanking sequence includes an unusual 'hybrid' site made up of overlapping E2F- and Sp1-like consensus sequences. Caveolin gene transcription was strongly downregulated at S-phase. This effect was absent following deletional mutagenesis of the −139 bp to −150 bp sequence, while 'baseline' (zero time) transcription rates were unaffected. The present study thus identifies a novel, additional mechanism that regulates caveolin transcription.

Transcriptional regulation is unlikely to be the only mechanism by which caveolin levels can be regulated during the cell cycle. The decrease in caveolin mRNA and protein levels observed in this study is greater than would be predicted from the reported $t_{1/2}$ of caveolin protein (Conrad et al. (1995) *J. Cell Biol.* 131: 1421–1433) suggesting additional contributions for accelerated mRNA and protein turnover in the overall regulation of expression. Nevertheless, the identification of a transcriptional mechanism, dependent on the G/C-rich promoter sequence at −139 to −150 bp, suggests integration of the effects of caveolin with other, better-recognized cell cycle proteins.

In summary, the present study provides evidence that among its effects, caveolin can contribute significantly to cell cycle regulation via mechanisms mediated through FC homeostasis and transport.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying an anti-mitotic agent, said method comprising the steps of:

contacting a cell with an agent to be tested for anti-mitotic activity; and detecting of the efflux of free cholesterol from said cell;

wherein an increase in efflux of free cholesterol by said cell when contacted by said agent as compared to said cell under the same conditions lacking said agent indicates antimitotic activity of said agent.

2. The method of claim 1, wherein said free cholesterol is labeled free cholesterol.

3. The method of claim 1, wherein said cell is in the presence of a low density lipoprotein (LDL).

4. The method of claim 2, wherein said labeled cholesterol is [$^3$H]-labeled free cholesterol.

5. The method of claim 1, wherein said cell comprises a reporter gene under the control of a caveolin promoter.

6. The method of claim 5, wherein said reporter gene is selected from the group consisting of a glucuronidase, bacterial chloramphenicol acetyl transferase (CAT), beta-galactosidase (β-gal), a firefly luciferase gene FFlux, and green fluorescent protein.

7. The method of claim 1, wherein said cell is selected from the group consisting of a fibroblast, a vascular smooth muscle cell, a vascular endothelial cell, a macrophage, a hematopoietic cell, a liver cell, a kidney cell, and an intestinal mucosal cell.

8. The method of claim 1, wherein said efflux is detected by detecting the level of caveolin expression wherein increased levels of caveolin expression indicates increased levels of free cholesterol efflux.

9. The method of claim 8, wherein detecting the level of caveolin expression comprises detecting the transcription level of a caveolin mRNA.

* * * * *

SEQUENCE LISTING

```
<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: ATPase ATP
      binding region.

<400> SEQUENCE: 1

Leu Leu Tyr Gly Pro Pro Gly Cys Gly Lys Thr Leu Leu Ala Arg
 1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: ATPase ATP
``` binding region.

<400> SEQUENCE: 2

Leu Phe Tyr Gly Pro Pro Gly Cys Gly Lys Thr Leu Leu Ala Lys
 1               5                   10                  15

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Anchor
      primer
<220> FEATURE:
<221> NAME/KEY: modified_base
<222> LOCATION: (36)..(37)
<223> OTHER INFORMATION: inosine (i)
<220> FEATURE:
<221> NAME/KEY: modified_base
<222> LOCATION: (41)..(42)
<223> OTHER INFORMATION: inosine (i)
<220> FEATURE:
<221> NAME/KEY: modified_base
<222> LOCATION: (46)..(47)
<223> OTHER INFORMATION: inosine (i)

<400> SEQUENCE: 3
cuacuacuac uaggccacgc gtcgactagt acgggnnggg nngggnng                48

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Probe
      cav-287

<400> SEQUENCE: 4
ctgcccaagc accccagcgc gggacaac                                      28

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Probe
      cav395

<400> SEQUENCE: 5
gcgtcggctc cctccacccc tgctgagatg atgcactg                           38

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Probe
      cav-646

<400> SEQUENCE: 6
caaaagtaca ccacaggcac ccacacagat tcctt                              35

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Oligo
      nucleotide probe to CLA-1 mRNA = nucleotides -continued

```
      1514-1543 of human CLA-1 cDNA

<400> SEQUENCE: 7
cagaataggc ctgaatggcc tccttatcct                                    30

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: caveolin
      promoter sequence at -139 to -159 bp.

<400> SEQUENCE: 8
ttggcgggcg gc                                                       12

<210> SEQ ID NO 9
<211> LENGTH: 7
<212> TYPE: DNA
<213> ORGANISM: Artificial Sequence
<220> FEATURE:
<223> OTHER INFORMATION: Description of Artificial Sequence: Sp1-like
      binding sequence.

<400> SEQUENCE: 9 ttggcgc                                                              7

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Sp1-like
      binding sequence.

<400> SEQUENCE: 10
ggcgggcggc                                                          10
```